(12) United States Patent
Hayward et al.

(10) Patent No.: US 6,699,904 B2
(45) Date of Patent: Mar. 2, 2004

(54) PPAR AGONISTS

(75) Inventors: Cheryl M. Hayward, Old Lyme, CT (US); David A. Perry, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/076,740

(22) Filed: Feb. 14, 2002

(65) Prior Publication Data

US 2002/0165282 A1 Nov. 7, 2002

Related U.S. Application Data

(60) Provisional application No. 60/269,058, filed on Feb. 15, 2001.

(51) Int. Cl.[7] .................. A01N 37/12; C07C 229/00; C07C 233/00; C07C 235/00
(52) U.S. Cl. .................. 514/535; 514/539; 514/561; 514/562; 514/564; 514/567; 514/596; 514/618; 514/361; 514/378; 514/381; 562/426; 562/455; 562/451; 564/47; 564/53; 564/54; 564/161; 564/182; 564/84; 564/92; 564/95; 564/184; 564/194; 548/131; 548/245; 548/253; 548/254; 560/37; 560/45; 560/48; 558/404; 558/408
(58) Field of Search ................. 562/451, 426, 562/455; 560/34, 37, 45, 48; 564/47, 53, 54; 548/161, 182, 131, 245, 253, 254; 514/535, 539, 561, 562, 564, 567, 596, 618

(56) References Cited

U.S. PATENT DOCUMENTS

| 4,238,506 A | * | 12/1980 | Stach et al. ................. 424/319 |
| 5,084,466 A | * | 1/1992 | Alig et al. ................... 514/353 |
| 5,658,844 A | * | 8/1997 | Hippel et al. ............... 502/353 |

FOREIGN PATENT DOCUMENTS

| WO | WO9210468 | 6/1992 | ......... C07C/275/34 |
| WO | WO9736579 | 10/1997 | .......... A61K/31/00 |
| WO | WO9805331 | 2/1998 | .......... A61K/31/45 |
| WO | WO0023407 | 4/2000 | ......... C07C/32/300 |

OTHER PUBLICATIONS

J. Med. Chem. 1996, 39, 3897–3907; Bernard Hulin, et al., Hypoglycemic Activity of a Series of a–Alkylthio and a–Alkoxy Carboxylic Acids Related to Ciglitazone.

* cited by examiner

Primary Examiner—Mark L. Berch
Assistant Examiner—Zachary C. Tucker
(74) Attorney, Agent, or Firm—Peter C. Richardson; Gregg C. Benson; Lisa A. Samuels

(57) ABSTRACT

PPAR alpha activators, pharmaceutical compositions containing such compounds and the use of such compounds to elevate certain plasma lipid levels, including high density lipoprotein-cholesterol and to lower certain other plasma lipid levels, such as LDL-cholesterol and triglycerides and accordingly to treat diseases which are exacerbated by low levels of HDL cholesterol and/or high levels of LDL-cholesterol and triglycerides, such as atherosclerosis and cardiovascular diseases, in mammals, including humans.

31 Claims, No Drawings

PPAR AGONISTS

This application claims priority from provisional application U.S. Ser. No. 60/269,058 filed Feb. 15, 2001, the benefit of which is hereby claimed under 37 C.F.R. §1.78 (a)(3).

BACKGROUND OF INVENTION

This invention relates to peroxisome proliferator activator receptor (PPAR) agonists, in particular, PPARα agonists, pharmaceutical compositions containing such agonists and the use of such agonists to treat atherosclerosis, hypercholesterolemia, hypertriglyceridemia, diabetes and obesity in mammals, including humans.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, gives rise to development of the "fibrous plaque," which consists of accumulated intimal smooth muscle cells laden with lipid and surrounded by extra-cellular lipid, collagen, elastin and proteoglycans. These cells plus matrix form a fibrous cap that covers a deeper deposit of cell debris and more extra-cellular lipid. The lipid is primarily free and esterified cholesterol. The fibrous plaque forms slowly, and is likely in time to become calcified and necrotic, advancing to the "complicated lesion," which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Additional independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatment of diabetes could be improved. The use of insulin typically requires multiple daily doses. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral hypoglycemic agents, e.g., thiazolidenediones, and in more severe cases, insulin. However, the clinically available hypoglycemic agents can have side effects that limit their use. In the case of insulin dependent diabetes mellitus (Type I), insulin is usually the primary course of therapy.

U.S. Pat. No. 5,658,944, WO92/10468, WO97/36579, WO98/05331 and WO 00/23407 disclose agents for the treatment of atherosclerosis, obesity and diabetes.

Thus, although there are a variety of anti-atherosclerosis and diabetes therapies, there is a continuing need and a continuing search in this field of art for alternative therapies.

SUMMARY OF THE INVENTION

This invention is directed to compounds of Formula I:

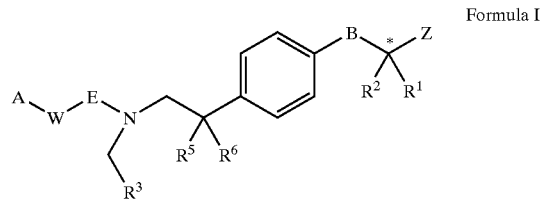

Formula I prodrugs thereof, and pharmaceutically acceptable salt of said compound and of said prodrugs;
wherein
E is carbonyl or sulfonyl;
B is methylene or —N(H)—;
Z is carboxyl, carboxaldehyde, hydroxymethyl, $(C_1–C_4)$ alkoxycarbonyl, cyano, hydroxyaminocarbonyl, tetrazolyl, tetrazolylaminocarbonyl, 4,5-dihydro-5-oxo-1,2,4-oxadiazol-3-yl, 3-oxoisoxazolidin-4-yl-aminocarbonyl, or —C(O)N(H)SO$_2$R$^4$;
where R$^4$ is $(C_1–C_6)$alkyl, amino or mono-N— or di-N,N—$(C_1–C_6)$alkylamino, said $(C_1–C_6)$alkyl substituents are optionally substituted independently with from one to nine fluorines; W is a bond, —N(H)—, —N($(C_1–C_4)$alkyl)—, $(C_1–C_4)$ alkylamino or $(C_1–C_8)$alkylene;
wherein said $(C_1–C_8)$alkylene may optionally be mono- or di-substituted independently with oxo, halo, $(C_1–C_6)$alkoxycarbonyl, $(C_1–C_6)$alkyl, $(C_2–C_6)$alkenyl, $(C_3–C_7)$cycloalkyl, hydroxy, $(C_1–C_6)$alkoxy, $(C_1–C_4)$alkylthio, amino, cyano, nitro, or mono-N— or di-N,N—$(C_1–C_6)$alkylamino or
wherein W is CR$^7$R$^8$ wherein R$^7$ and R$^8$ are linked together to form a three to six membered fully saturated carbocyclic ring;
R$^1$ is H, $(C_1–C_6)$alkyl or $(C_3–C_6)$cycloalkyl;
R$^2$ is H, a $(C_3–C_6)$cycloalkyl or a fully saturated, partially unsaturated or fully unsaturated one to four membered straight or branched carbon chain wherein the carbon(s) may optionally be replaced with one or two heteroatoms selected independently from oxygen and sulfur and wherein said carbon(s) is optionally mono-, di- or tri-substituted independently with halo, said carbon(s) is optionally mono-substituted with hydroxy, said carbon(s) is optionally mono-substituted with oxo, said sulfur is optionally mono- or di-substituted with oxo, and said chain is optionally mono-substituted with Y;
wherein Y is a partially saturated, fully saturated or fully unsaturated three to eight membered ring optionally having one to four heteroatoms selected independently from oxygen, sulfur and nitrogen or a bicyclic ring consisting of two fused partially saturated, fully saturated or fully unsaturated three to six membered rings, taken independently, said bicyclic ring optionally having one to four heteroatoms selected independently from oxygen, sulfur and nitrogen;

wherein said Y ring is optionally mono-, di- or tri-substituted independently with halo, $(C_2-C_6)$ alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; or $R^1$ and $R^2$ are linked together to form a three to six membered fully saturated carbocyclic ring optionally having one heteroatom selected from oxygen, sulfur and nitrogen;

$R^3$ is $(C_1-C_{10})$alkyl, $(C_2-C_{10})$alkenyl or $(C_2-C_{10})$alkynyl, said $(C_1-C_{10})$alkyl, $(C_2-C_{10})$alkenyl or $(C_2-C_{10})$ alkynyl substituents are optionally mono-, di- or tri-substituted independently with halo, hydroxy, $(C_1-C_6)$ alkoxy, $(C_1-C_4)$alkylthio, amino, nitro, cyano, oxo, carboxy, $(C_1-C_6)$alkyloxycarbonyl, mono-N— or di-N, N—$(C_1-C_6)$alkylamino or optionally said $(C_1-C_{10})$alkyl, $(C_2-C_{10})$alkenyl or $(C_2-C_{10})$ alkynyl substituents are mono-substituted with a partially saturated, fully saturated or fully unsaturated five to six membered ring optionally having one to two heteroatoms selected from nitrogen, oxygen and sulfur, or a bicyclic ring consisting of two fused partially saturated, fully saturated or fully unsaturated three to six membered rings, taken independently, said bicyclic ring optionally having one to four heteroatoms selected independently from oxygen, sulfur and nitrogen;

said ring optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$ alkyloxycarbonyl, mono-N— or di-N,N—$(C_1-C_6)$ alkylamino wherein said $(C_1-C_6)$alkyl substituent is optionally mono-, di- or tri-substituted independently with halo, hydroxy, $(C_1-C_6)$alkoxy, $(C_1-C_4)$ alkylthio, amino, nitro, cyano, oxo, carboxy, $(C_1-C_6)$ alkyloxycarbonyl, mono-N— or di-N,N—$(C_1-C_6)$ alkylamino, said $(C_1-C_6)$alkyl substituent is also optionally substituted with from one to nine fluorines;

$R^5$ and $R^6$ are linked together to form a three to six membered fully saturated carbocyclic ring or are each independently H, $(C_1-C_6)$alkyl, $(C_3-C_7)$cycloalkyl or $(C_3-C_7)$cycloalkyl$(C_1-C_6)$alkyl; and A is H, mono-N— or di-N,N—$(C_1-C_6)$alkylamino, $(C_2-C_6)$alkanoylamino, $(C_1-C_6)$alkoxy, or a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, said bicyclic ring optionally having one to four heteroatoms selected independently from oxygen, sulfur and nitrogen; and wherein said A ring is optionally mono-, di- or tri-substituted independently with oxo, carboxy, halo, $(C_1-C_6)$alkoxycarbonyl, $(C_1-C_6)$alkyl, $(C_2-C_6)$ alkenyl, $(C_3-C_7)$cycloalkyl, $(C_3-C_7)$cycloalkyl $(C_1-C_6)$alkyl, hydroxy, $(C_1-C_6)$alkoxy, $(C_1-C_4)$ alkylthio, amino, cyano, nitro, or mono-N— or di-N, N—$(C_1-C_6)$alkylamino wherein said $(C_1-C_6)$alkyl or $(C_1-C_6)$alkoxy substituents are optionally mono-, di- or tri-substituted independently with halo, hydroxy, $(C_1-C_6)$alkoxy, amino, mono-N— or di-N, N—$(C_1-C_6)$alkylamino or from one to nine fluorines, or wherein said A ring is optionally mono-substituted with a partially saturated, fully saturated or fully unsaturated three to eight membered ring optionally having one to four heteroatoms selected independently from oxygen, sulfur and nitrogen.

A preferred group of compounds, designated the A Group, contains those compounds having the Formula I as shown above wherein E is C(O);

B is methylene;

Z is carboxy;

W is a bond, $(C_1-C_4)$alkylene, or —N(H)—;

$R^1$ is H or $(C_1-C_4)$alkyl;

$R^2$ is H, $(C_1-C_4)$alkyl or $(C_1-C_4)$alkoxy;

$R^3$ is $(C_4-C_8)$alkyl;

$R^5$ and $R^6$ are each H; and

A is a five to six membered partially saturated, fully saturated or fully unsaturated ring optionally having one heteroatom selected from oxygen, sulfur and nitrogen, or a bicyclic ring consisting of two fused partially saturated, fully saturated or fully unsaturated five to six membered ring, taken independently, optionally having one to four heteroatoms selected independently from oxygen, sulfur and nitrogen;

wherein said A substituent is optionally mono-, di- or tri-substituted independently with halo, $(C_1-C_6)$ alkyl, hydroxy, $(C_1-C_6)$alkoxy, $(C_1-C_4)$alkylthio, amino, nitro, cyano or mono-N— or di-N,N— $(C_1-C_6)$alkylamino, said $(C_1-C_6)$alkyl or $(C_1-C_6)$ alkoxy substituents are optionally substituted independently with from one to nine fluorines; and the pharmaceutically acceptable salts thereof.

A group of compounds which is preferred among the A Group of compounds, designated the B Group, contains those compounds wherein $R^1$ is H or $(C_1-C_4)$alkyl;

$R^2$ is H, $(C_1-C_4)$alkoxy or $(C_1-C_4)$alkyl; and

A is phenyl, wherein said phenyl substituent is optionally mono-, di- or tri-substituted independently with halo, $(C_1-C_6)$ alkyl, hydroxy, $(C_1-C_6)$alkoxy, $(C_1-C_4)$ alkylthio, amino, nitro, cyano or mono-N— or di-N, N—$(C_1-C_6)$alkylamino, said $(C_1-C_6)$alkyl or $(C_1-C_6)$ alkoxy substituents are optionally substituted independently with from one to nine fluorines; and the pharmaceutically acceptable salts thereof.

A group of compounds which is preferred among the B Group of compounds, designated the C Group, contains those compounds wherein W is N(H)—;

$R^1$ is H or $(C_1-C_4)$alkyl;

$R^2$ is H, $(C_1-C_4)$alkoxy or $(C_1-C_2)$alkyl;

said A phenyl substituent is optionally mono- or di-substituted independently with fluoro, trifluoromethyl, trifluoromethoxy, chloro, $(C_1-C_4)$alkyl, hydroxy, cyano, $(C_1-C_2)$alkoxy, amino or mono-N— or di-N,N—$(C_1-C_2)$alkylamino; and $R^3$ is $(C_6-C_8)$alkyl; and the pharmaceutically acceptable salts thereof.

Especially preferred compounds of Formula I are the compounds (R)-3-(4-{2-[3-(2,4-dimethoxy-phenyl)-1-heptyl-ureido]-ethyl}-phenyl)-2-ethoxy-propionic acid;

(S)-3-(4-{2-[3-(2,4-dimethoxy-phenyl)-1-heptyl-ureido]-ethyl}-phenyl)-2-ethoxy-propionic acid;

(R)-2-ethoxy-3-(4-{2-[1-heptyl-3-(4-isopropyl-phenyl)-ureido]-ethyl}-phenyl)-propionic acid;

(S)-2-ethoxy-3-(4-{2-[1-heptyl-3-(4-isopropyl-phenyl)-ureido]-ethyl}-phenyl)-propionic acid;

(R)-3-(4-{2-[3-(2,3-dichloro-phenyl)-1-heptyl-ureido]-ethyl}-phenyl)-2-ethoxy-propionic acid;

(S)-3-(4-{2-[3-(2,3-dichloro-phenyl)-1-heptyl-ureido]-ethyl}-phenyl)-2-ethoxy-propionic acid;

(R)-2-ethoxy-3-(4-{2-[1-heptyl-3-(4-trifluoromethoxy-phenyl)-ureido]-ethyl}-phenyl)-propionic acid;

(S)-2-ethoxy-3-(4-{2-[1-heptyl-3-(4-trifluoromethoxy-phenyl)-ureido]-ethyl}-phenyl)-propionic acid;

(R)-3-(4-{2-[3-(2,4-dimethyl-phenyl)-1-heptyl-ureido]-ethyl}-phenyl)-2-ethoxy-propionic acid;

(S)-3-(4-{2-[3-(2,4-dimethyl-phenyl)-1-heptyl-ureido]-ethyl}-phenyl)-2-ethoxy-propionic acid;

(R)-3-(4-{2-[3-(4-tert-butyl-phenyl)-1-heptyl-ureido]-ethyl}-phenyl)-2-ethoxy-propionic acid;

(S)-3-(4-{2-[3-(4-tert-butyl-phenyl)-1-heptyl-ureido]-ethyl}-phenyl)-2-ethoxy-propionic acid;

and the pharmaceutically acceptable salts of said compounds.

Especially preferred compounds within the C Group of compounds are compounds wherein a. $R^1$ is hydrogen;
$R^2$ is ethoxy;
$R^3$ is heptyl; and
A is 2,4-dimethoxyphenyl;

b. $R^1$ is hydrogen;
$R^2$ is ethoxy;
$R^3$ is heptyl; and
A is 4-isopropylphenyl;

c. $R^1$ is hydrogen;
$R^2$ is ethoxy;
$R^3$ is heptyl; and
A is 2,3-dichlorophenyl;

d. $R^1$ is hydrogen;
$R^2$ is ethoxy;
$R^3$ is heptyl; and
A is 4-trifluoromethoxyphenyl;

e. $R^1$ is hydrogen;
$R^2$ is ethoxy;
$R^3$ is heptyl; and
A is 2,4-dimethylphenyl;

f. $R^1$ is hydrogen;
$R^2$ is ethoxy;
$R^3$ is heptyl; and
A is 4-tertbutylphenyl;

and the pharmaceutically acceptable salts of said compounds.

A group of compounds which is preferred among the B Group of compounds, designated the D Group, contains those compounds wherein W is methylene;

$R^1$ is H or $(C_1-C_4)$alkyl;

$R^2$ is H, $(C_1-C_4)$alkoxy or $(C_1-C_2)$alkyl;

said A phenyl substituent is optionally mono- or di-substituted independently with fluoro, trifluoromethyl, trifluoromethoxy, chloro, $(C_1-C_3)$alkyl, hydroxy, $(C_1-C_2)$alkoxy, amino or mono-N— or di-N,N—$(C_1-C_2)$alkylamino; and $R^3$ is $(C_4-C_8)$alkyl; and the pharmaceutically acceptable salts thereof.

Especially preferred compounds of Formula I are the compounds (R)-3-[4-(2-{[(2,4-difluoro-phenyl)-acetyl]-heptyl-amino}-ethyl)phenyl]-2-ethoxy-propionic acid;

(S)-3-[4-(2-{[(2,4-difluoro-phenyl)-acetyl]-heptyl-amino}-ethyl)-phenyl]-2-ethoxy-propionic acid;

(R)-2-ethoxy-3-{4-[2-(heptyl-p-tolylacetyl-amino)-ethyl]-phenyl}-propionic acid;

(S)-2-ethoxy-3-{4-[2-(heptyl-p-tolylacetyl-amino)-ethyl]-phenyl}-propionic acid;

and the pharmaceutically acceptable salts of said compounds.

Especially preferred compounds within the D Group of compounds are compounds wherein a. $R^1$ is hydrogen;
$R^2$ is ethoxy;
$R^3$ is heptyl;
A is 2,4-difluorophenyl;

b. $R^1$ is hydrogen;
$R^2$ is ethoxy;
$R^3$ is heptyl; and
A is 4-methylphenyl;

and the pharmaceutically acceptable salts of said compounds.

A preferred group of compounds, designated the E Group, contains those compounds having the Formula I as shown above wherein E is C(O);

B is $CH_2$;

Z is carboxy;

W is a bond, $(C_1-C_4)$alkylene or —N(H)—;

$R^1$ is H, $(C_1-C_4)$alkyl or $(C_3-C_6)$cycloalkyl;

$R^2$ is H, $(C_1-C_4)$alkyl, $(C_1-C_4)$alkoxy, $(C_1-C_4)$alkylthio, phenoxy, benzyloxy, phenylthio, benzylthio, or $(C_3-C_6)$cycloalkyl, said phenyl moieties optionally mono-or di-substituted independently with cyano, fluoro, trifluoromethyl, trifluoromethoxy, chloro, $(C_1-C_3)$alkyl, hydroxy, $(C_1-C_2)$alkoxy, amino or mono-N-or di-N,N—$(C_1-C_2)$alkylamino;

$R^3$ is $(C_4-C_8)$alkyl;

$R^5$ and $R^6$ are each H; and

A is a five to six membered partially saturated, fully saturated or fully unsaturated ring optionally having one heteroatom selected from oxygen, sulfur and nitrogen, or a bicyclic ring consisting of two fused partially saturated, fully saturated or fully unsaturated five to six membered rings, taken independently, optionally having one to four heteroatoms selected independently from oxygen, sulfur and nitrogen;

wherein said A substituent is optionally mono-, di- or tri-substituted independently with halo, $(C_1-C_6)$ alkyl, hydroxy, $(C_1-C_6)$alkoxy, $(C_1-C_4)$alkylthio, amino, nitro, cyano, or mono-N— or di-N,N—$(C_1-C_6)$alkylamino, said $(C_1-C_6)$alkyl or $(C_1-C_6)$ alkoxy substituents are optionally substituted independently with from one to nine fluorines; and the pharmaceutically acceptable salts thereof.

A group of compounds which is preferred among the E Group of compounds, designated the F Group, contains those compounds wherein W is N(H)—;

$R^1$ is H, $(C_1-C_4)$alkyl, or $(C_3-C_6)$cycloalkyl;

$R^2$ is H, $(C_1-C_4)$alkyl, $(C_1-C_4)$alkoxy, phenoxy, benzyloxy, or $(C_3-C_6)$cycloalkyl, said phenyl moieties optionally mono-or di-substituted independently with cyano, fluoro, trifluoromethyl, trifluoromethoxy, chloro, $(C_1-C_3)$alkyl, hydroxy, $(C_1-C_2)$alkoxy, amino or mono-N— or di-N,N—$((C_1-C_2)$alkylamino;

$R^3$ is $(C_6-C_8)$alkyl;

$R^5$ and $R^6$ are each H; and

A is phenyl, wherein said phenyl substituent is optionally mono-, di- or tri-substituted independently with halo, $(C_1-C_6)$ alkyl, hydroxy, $(C_1-C_6)$alkoxy, $(C_1-C_4)$ alkylthio, amino, nitro, cyano or mono-N— or di-N, N—$(C_1-C_6)$alkylamino, said $(C_1-C_6)$alkyl or $(C_1-C_6)$ alkoxy substituents are optionally substituted independently with from one to nine fluorines; and the pharmaceutically acceptable salts thereof.

A group of compounds which is preferred among the F Group of compounds, designated the G Group, contains those compounds wherein $R^1$ is H;

said A phenyl substituent is optionally mono- or di-substituted independently with fluoro, trifluoromethyl, trifluoromethoxy, chloro, $(C_1-C_3)$alkyl, hydroxy, $(C_1-C_2)$alkoxy, amino or mono-N— or di-N,N—$(C_1-C_2)$alkylamino;

and the pharmaceutically salts thereof.

Especially preferred compounds of Formula I are the compounds (R)-2-benzyloxy-3-(4-{2-[1-heptyl-3-(4-isopropyl-phenyl)-ureido]-ethyl}-phenyl)-propionic acid;

(S)-2-benzyloxy-3-(4-{2-[1-heptyl-3-(4-isopropyl-phenyl)-ureido]-ethyl}-phenyl)-propionic acid;

(R)-3-(4-{2-[1-heptyl-3-(4-isopropyl-phenyl)-ureido]-ethyl}-phenyl)-2-phenoxy-propionic acid;

(S)-3-(4-{2-[1-heptyl-3-(4-isopropyl-phenyl)-ureido]-ethyl}-phenyl)-2-phenoxy-propionic acid;

(R)-2-benzyloxy-3-(4-{2-[3-(2,4-dimethoxy-phenyl)-1-heptyl-ureido]-ethyl}-phenyl)-propionic acid;

(S)-2-benzyloxy-3-(4-{2-[3-(2,4-dimethoxy-phenyl)-1-heptyl-ureido]-ethyl}-phenyl)-propionic acid;

and the pharmaceutically acceptable salts of said compounds.

Especially preferred compounds within the G Group of compounds are compounds wherein a. $R^2$ is benzyloxy;
   $R^3$ is heptyl; and
   A is 4-isopropylphenyl;

b. $R^2$ is phenoxy;
   $R^3$ is heptyl; and
   A is 4-isopropylphenyl;

c. $R^2$ is benzyloxy;

$R^3$ is heptyl; and
A is 2,4-methoxyphenyl;

and the pharmaceutically acceptable salts of said compounds.

A group of compounds which is preferred among the E Group of compounds, designated the H Group, contains those compounds wherein W is N(H)—;

$R^1$ is H, $(C_1-C_4)$alkyl or $(C_1-C_4)$cycloalkyl;

$R^2$ is H, $(C_1-C_4)$alkylthio, phenylthio or phenylmethylthio, said phenyl moieties optionally mono-or di-substituted independently with cyano, fluoro, trifluoromethyl, trifluoromethoxy, chloro, $(C_1-C_3)$alkyl, hydroxy, $(C_1-C_2)$alkoxy, amino or mono-N— or di-N,N—$((C_1-C_2)$alkylamino;

$R^3$ is $(C_6-C_8)$alkyl;

$R^5$ and $R^6$ are each H; and

A is phenyl, wherein said phenyl substituent is optionally mono-, di- or tri-substituted independently with halo, $(C_1-C_6)$ alkyl, hydroxy, $(C_1-C_6)$alkoxy, $(C_1-C_4)$ alkylthio, amino, nitro, cyano or mono-N— or di-N, N—$(C_1-C_6)$alkylamino, said $(C_1-C_6)$alkyl or $(C_1-C_6)$ alkoxy substituents are optionally substituted independently with from one to nine fluorines and the pharmaceutically acceptable salts thereof.

A group of compounds which is preferred among the H Group of compounds, designated the I Group, contains those compounds wherein $R^1$ is H;

said A phenyl substituent is optionally mono- or di-substituted independently with fluoro, trifluoromethyl, trifluoromethoxy, chloro, $(C_1-C_3)$ alkyl, hydroxy, $(C_1-C_2)$alkoxy, amino or mono-N— or di-N,N—$(C_1-C_2)$alkylamino;

and the pharmaceutically acceptable salts thereof.

Especially preferred compounds of Formula I are the compounds (R)-3-(4-{2-[1-heptyl-3-(4-isopropyl-phenyl)-ureido]-ethyl}-phenyl)-2-isopropylsulfanyl-propionic acid;

(S)-3-(4-{2-[1-heptyl-3-(4-isopropyl-phenyl)-ureido]-ethyl}-phenyl)-2-isopropylsulfanyl-propionic acid;

(R)-2-benzylsulfanyl-3-(4-{2-[1-heptyl-3-(4-isopropyl-phenyl)-ureido]-ethyl}-phenyl)-propionic acid;

(S)-2-benzylsulfanyl-3-(4-{2-[1-heptyl-3-(4-isopropyl-phenyl)-ureido]-ethyl}-phenyl)-propionic acid;

(R)-2-ethylsulfanyl-3-(4-{2-[1-heptyl-3-(4-isopropyl-phenyl)-ureido]-ethyl}-phenyl)-propionic acid;

(S)-2-ethylsulfanyl-3-(4-{2-[1-heptyl-3-(4-isopropyl-phenyl)-ureido]-ethyl}-phenyl)-propionic acid;

(R)-3-(4{-2-[1-heptyl-3-(4-isopropyl-phenyl)-ureido]-ethyl}-phenyl)-2-phenylsulfanyl-propionic acid;

(S)-3-(4-{2-[1-heptyl-3-(4-isopropyl-phenyl)-ureido]-ethyl}-phenyl)-2-phenylsulfanyl-propionic acid;

and the pharmaceutically acceptable salts of said compounds.

Especially preferred compounds among the I Group of compounds are a. $R^2$ is isopropylthio;
   $R^3$ is heptyl; and
   A is 4-isopropylphenyl;

b. $R^2$ is benzylthio;
   $R^3$ is heptyl; and
   A is 4-isopropylphenyl;

c. $R^2$ is ethylthio;

$R^3$ is heptyl; and
A is 4-isopropylphenyl;
d. $R^2$ is phenylthio;
$R^3$ is heptyl; and
A is 4-isopropylphenyl;
and the pharmaceutically acceptable salts of said compounds.

Especially preferred compounds of Formula I are the compounds
E is C(O);
B is $CH_2$;
Z is carboxy;
W is a bond or $(C_1-C_4)$alkylene;
$R^1$ is H, $(C_1-C_4)$alkyl, or $(C_3-C_6)$cycloalkyl;
$R^2$ is H, $(C_1-C_4)$alkyl, $(C_1-C_4)$alkoxy, $(C_1-C_4)$alkylthio, phenoxy, benzyloxy, phenylthio, benzylthio, or $(C_1-C_4)$cycloalkyl, said phenyl moieties optionally mono-or di-substituted independently with cyano, fluoro, trifluoromethyl, trifluoromethoxy, chloro, $(C_1-C_3)$alkyl, hydroxy, $(C_1-C_2)$alkoxy, amino or mono-N— or di-N,N—$(C_1-C_2)$alkylamino;
$R^3$ is $(C_4-C_8)$alkyl;
$R^5$ and $R^6$ are each H; and
A is a five to six membered partially saturated, fully saturated or fully unsaturated ring optionally having one heteroatom selected from oxygen, sulfur and nitrogen, or a bicyclic ring consisting of two fused partially saturated, fully saturated or fully unsaturated five to six membered rings, taken independently, optionally having one to four heteroatoms selected independently from oxygen, sulfur and nitrogen;
wherein said A substituent is optionally mono-, di- or tri-substituted independently with halo, $(C_1-C_6)$ alkyl, hydroxy, $(C_1-C_6)$alkoxy, $(C_1-C_4)$alkylthio, amino, nitro, cyano, or mono-N— or di-N,N—$(C_1-C_6)$alkylamino, said $(C_1-C_6)$alkyl or $(C_1-C_6)$ alkoxy substituents are optionally substituted independently with from one to nine fluorines; and the pharmaceutically acceptable salts thereof.

Another aspect of this invention is directed to methods of treating obesity, overweight condition, hypertriglyceridemia, hyperlipidemia, hypoalphalipoproteinemia, Syndrome X, diabetes mellitus (especially Type II), hyperinsulinemia, impaired glucose tolerance, insulin resistance, a diabetic complication, atherosclerosis, hypertension, coronary heart disease, hypercholesterolemia, inflammation, thrombosis or congestive heart failure in a mammal (including a human being) which comprise administering to said mammal a therapeutically effective amount of a compound of Formula I, a prodrug of said compound, or a pharmaceutically acceptable salt of said compound or prodrug.

Yet another aspect of this invention is directed to methods for treating obesity in a mammal (including a human being) by administering to a mammal in need of such treatment an obesity treating amount of a Formula I compound, a prodrug thereof, or a pharmaceutically acceptable salt of said compound or of said prodrug.

Yet another aspect of this invention is directed to methods for inducing weight loss in a mammal (including a human being) by administering to a mammal a therapeutically effective amount of a Formula I compound, a prodrug of thereof, or a pharmaceutically acceptable salt of said compound or of said prodrug.

Yet another aspect of this invention is directed to methods for treating an overweight condition in a mammal (including a human being) by administering to a mammal in need of such treatment an overweight condition treating amount of a Formula I compound, a prodrug thereof, or a pharmaceutically acceptable salt of said compound or of said prodrug.

Yet another aspect of this invention is directed to methods for treating hypertriglyceridemia in a mammal (including a human being) by administering to a mammal in need of such treatment a hypertriglyceridemia treating amount of a Formula I compound, a prodrug thereof, or a pharmaceutically acceptable salt of said compound or of said prodrug.

Yet another aspect of this invention is directed to methods for treating hyperlipidemia in a mammal (including a human being) by administering to a mammal in need of such treatment a hyperlipidemia treating amount of a Formula I compound, a prodrug thereof, or a pharmaceutically acceptable salt of said compound or of said prodrug.

Yet another aspect of this invention is directed to methods for treating hypoalphalipoproteinemia in a mammal (including a human being) by administering to a mammal in need of such treatment a hypoalphalipoproteinemia treating amount of a Formula I compound, a prodrug thereof, or a pharmaceutically acceptable salt of said compound or of said prodrug.

Yet another aspect of this invention is directed to methods for treating Syndrome X in a mammal (including a human being) by administering to a mammal in need of such treatment a Syndrome X treating amount of a Formula I compound, a prodrug thereof, or a pharmaceutically acceptable salt of said compound or of said prodrug.

Yet another aspect of this invention is directed to methods for treating diabetes mellitus (especially Type II) in a mammal (including a human being) by administering to a mammal in need of such treatment a diabetes mellitus treating amount of a Formula I compound, a prodrug thereof, or a pharmaceutically acceptable salt of said compound or of said prodrug.

Yet another aspect of this invention is directed to methods for treating hyperinsulinemia in a mammal (including a human being) by administering to a mammal in need of such treatment a hyperinsulinemia treating amount of a Formula I compound, a prodrug thereof, or a pharmaceutically acceptable salt of said compound or of said prodrug.

Yet another aspect of this invention is directed to methods for treating impaired glucose tolerance in a mammal (including a human being) by administering to a mammal in need of such treatment an impaired glucose tolerance disease treating amount of a Formula I compound, a prodrug thereof, or a pharmaceutically acceptable salt of said compound or of said prodrug.

Yet another aspect of this invention is directed to methods for treating insulin resistance in a mammal (including a human being) by administering to a mammal in need of such treatment an insulin resistance treating amount of a Formula I compound, a prodrug thereof, or a pharmaceutically acceptable salt of said compound or of said prodrug.

Yet another aspect of this invention is directed to methods for treating a diabetic complication (e.g., neuropathy, nephropathy, retinopathy or cataracts) in a mammal (including a human being) by administering to a mammal in need of such treatment a diabetic complication treating amount of a Formula I compound, a prodrug thereof, or a pharmaceutically acceptable salt of said compound or of said prodrug.

Yet another aspect of this invention is directed to methods for treating atherosclerosis in a mammal (including a human being) by administering to a mammal in need of such treatment an atherosclerotic treating amount of a Formula I compound, a prodrug thereof, or a pharmaceutically acceptable salt of said compound or of said prodrug.

Yet another aspect of this invention is directed to methods for treating hypertension in a mammal (including a human being) by administering to a mammal in need of such treatment a hypertension treating amount of a Formula I compound, a prodrug thereof, or a pharmaceutically acceptable salt of said compound or of said prodrug.

Yet another aspect of this invention is directed to methods for treating coronary heart disease in a mammal (including a human being) by administering to a mammal in need of such treatment a coronary heart disease treating amount of a Formula I compound, a prodrug thereof, or a pharmaceutically acceptable salt of said compound or of said prodrug.

Yet another aspect of this invention is directed to methods for treating hypercholesterolemia in a mammal (including a human being) by administering to a mammal in need of such treatment a hypercholesterolemia treating amount of a Formula I compound, a prodrug thereof, or a pharmaceutically acceptable salt of said compound or of said prodrug.

Yet another aspect of this invention is directed to methods for treating inflammation in a mammal (including a human being) by administering to a mammal in need of such treatment an inflammation treating amount of a Formula I compound, a prodrug thereof, or a pharmaceutically acceptable salt of said compound or of said prodrug.

Yet another aspect of this invention is directed to methods for treating congestive heart failure in a mammal (including a human being) by administering to a mammal in need of such treatment a congestive heart failure treating amount of a Formula I compound, a prodrug thereof, or a pharmaceutically acceptable salt of said compound or of said prodrug.

A preferred dosage is about 0.001 to about 100 mg/kg/day of a Formula I compound, a prodrug thereof, or a pharmaceutically acceptable salt of said compound or of said prodrug. An especially preferred dosage is about 0.01 to about 10 mg/kg/day of a Formula I compound, a prodrug thereof, or a pharmaceutically acceptable salt of said compound or of said prodrug.

This invention is also directed to pharmaceutical compositions which comprise a compound of Formula I, a prodrug thereof, or a pharmaceutically acceptable salt of said compound or of said prodrug and a pharmaceutically acceptable vehicle, carrier or diluent. Preferably the composition comprises a therapeutically effective amount of the Formula I compound.

This invention is also directed to pharmaceutical compositions for the treatment of obesity, an overweight condition, hypertriglyceridemia, hyperlipidemia, hypoalphalipoproteinemia, Syndrome X, diabetes mellitus (especially Type II), hyperinsulinemia, impaired glucose tolerance, insulin resistance, a diabetic complication, atherosclerosis, hypertension, coronary heart disease, hypercholesterolemia, inflammation, or congestive heart failure in a mammal (including a human being) which comprise a therapeutically effective amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of obesity in a mammal (including a human being) which comprise an obesity treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of an overweight condition in a mammal (including a human being) which comprise an overweight condition treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of hypertriglyceridemia in a mammal (including a human being) which comprise a hypertriglyceridemia treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of hyperlipidemia in a mammal (including a human being) which comprise a hyperlipidemia treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of hypoalphalipoproteinemia in a mammal (including a human being) which comprise a hypoalphalipoproteinemia treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of Syndrome X in a mammal (including a human being) which comprise a Syndrome X treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of diabetes mellitus (especially Type II) in a mammal (including a human being) which comprise a diabetes mellitus treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of hyperinsulinemia in a mammal (including a human being) which comprise a hyperinsulinemia treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of impaired glucose tolerance in a mammal (including a human being) which comprise an impaired glucose tolerance treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of insulin resistance in a mammal (including a human being) which comprise an insulin resistance treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of a diabetic complication (e.g., neuropathy, nephropathy, retinopathy or cataracts) in a mammal (including a human being) which comprise a diabetic complication treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of atherosclerosis in a mammal (including a human being) which comprise an atherosclerosis treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of hypertension in a mammal (including a human being) which comprise a hypertension treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of coronary heart disease in a mammal (including a human being) which comprise a coronary heart disease treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of hypercholesterolemia in a mammal (including a human being) which comprise a hypercholesterolemia treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of inflammation in a mammal (including a human being) which comprise an inflammation treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical compositions for the treatment of congestive heart failure in a mammal (including a human being) which comprise a congestive heart failure treating amount of a compound of Formula I, a prodrug thereof, or a pharmaceutically acceptable salt of said compound or of said prodrug and a pharmaceutically acceptable vehicle, diluent or carrier.

This invention is also directed to pharmaceutical combination composition comprising: a therapeutically effective amount of a composition comprising a first compound, said first compound being a Formula I compound, a prodrug thereof, or a pharmaceutically acceptable salt of said compound or of said prodrug;

a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, a microsomal triglyceride transfer protein (MTP)/Apo B secretion inhibitor, a cholesterol ester transfer protein (CETP) inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/ squalene cyclase inhbitior, a fibrate, niacin, an ion-exchange resin, an antioxidant, an acyl-CoA:cholesterol acyl transferase (ACAT) inhibitor or a bile acid sequestrant; and/or optionally a pharmaceutically acceptable vehicle, diluent or carrier.

Preferred among the second compounds are an HMG-CoA reductase inhibitor and a CETP inhibitor.

A particularly preferred HMG-CoA reductase inhibitor is lovastatin, rosuvastatin, itavastatin, simvastatin, pravastatin, fluvastatin, atorvastatin or rivastatin or a pharmaceutically acceptable salt thereof.

Another aspect of this invention is methods for treating atherosclerosis in a mammal comprising administering to a mammal suffering from atherosclerosis a first compound, said first compound being a Formula I compound, a prodrug thereof, or a pharmaceutically acceptable salt of said compound or of said prodrug; and a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, a MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, an ion-exchange resin, an antioxidant, an ACAT inhibitor or a bile acid sequestrant wherein the amounts of the first and second compounds result in a therapeutic effect.

A preferred aspect of the above methods is wherein the second compound is an HMG-CoA reductase inhibitor or a CETP inhibitor.

A particularly preferred aspect of the above method is wherein the HMG-CoA reductase inhibitor is lovastatin, rosuvastatin, itavastatin, simvastatin, pravastatin, fluvastatin, atorvastatin or rivastatin or a pharmaceutically acceptable salt thereof.

Yet another aspect of this invention is kits comprising:

a. a first compound, said first compound being a Formula I compound, a prodrug thereof, or a pharmaceutically acceptable salt of said compound or of said prodrug and a pharmaceutically acceptable carrier, vehicle or diluent in a first unit dosage form;

b. a second compound, said second compound being a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/ squalene cyclase inhibitor, a fibrate, niacin, an ion-exchange resin, an antioxidant, an ACAT inhibitor or a bile acid sequestrant and a pharmaceutically acceptable carrier, vehicle or diluent in a second unit dosage form; and c. means for containing said first and second dosage forms wherein the amounts of the first and second compounds result in a therapeutic effect.

A preferred second compound is an HMG-CoA reductase inhibitor or a CETP inhibitor.

A particularly preferred HMG-CoA reductase inhibitor is lovastatin, rosuvastatin, itavastatin, simvastatin, pravastatin, fluvastatin, atorvastatin or rivastatin or pharmaceutically acceptable salts thereof.

This invention is also directed to pharmaceutical combination compositions comprising: a therapeutically effective amount of a composition comprising a first compound, said first compound being a Formula I compound, a prodrug thereof, or a pharmaceutically acceptable salt of said compound or of said prodrug;

a second compound, said second compound being a diabetic treating agent selected from aldose reductase inhibitors, glucocorticoid receptor antagonists, glycogenolysis inhibitors, glycogen phosphorylase inhibitors, sorbitol dehydrogenase inhibitors, insulin, insulin analogs, insulinotropin, sulfonylureas, sulfonylurea analogs, biguanides, imidazolines, insulin secretagogues, linogliride, glitazones, glucosidase inhibitors, acarbose, miglitol, emiglitate, voglibose, camiglibose, β-agonists, phosphodiesterase inhibitors, vanadate, vanadium complexes (e.g. Naglivan®), peroxovanadium complexes, amylin antagonists, glucagon antagonists, gluconeogenesis inhibitors, somatostatin analogs, antilipolytic agents, nicotinic acid, acipimox, pramlintide (Symlin™), and nateglinide; and/or optionally a pharmaceutical vehicle, diluent or carrier.

Preferred among the second compounds are chlorpropamide, glibenclamide, tolbutamide, tolazamide, acetohexamide, Glypizide®, glimepiride, repaglinide, meglitinide, mefformin, phenformin, buformin, midaglizole, isaglidole, deriglidole, idazoxan, efaroxan, fluparoxan, ciglitazone, pioglitazone, englitazone, darglitazone, clomoxir, etomoxir.

Particularly preferred second compounds are glibenclamide, Glypizide®, glimepiride, repaglinide, metformin, and pioglitazone.

Another aspect of this invention is methods for treating diabetes in a mammal comprising administering to a mammal suffering from diabetes a first compound, said first compound being a Formula I compound a prodrug thereof, or a pharmaceutically acceptable salt of said compound or of said prodrug; and a second compound, said second compound being a diabetic treating agent selected from aldose reductase inhibitors, glucocorticoid receptor antagonists, glycogenolysis inhibitors, glycogen phosphorylase inhibitors, sorbitol dehydrogenase inhibitors, insulin, insulin analogs, insulinotropin, sulfonylurea, sulfonylurea analogs, biguanides, imidazolines, insulin secretagogues, linogliride, glitazones, α-glucosidase inhibitors, acarbose, miglitol, emiglitate, voglibose, camiglibose, β-agonists, phosphodiesterase inhibitors, vanadate, vanadium complexes (e.g. Naglivan®), peroxovanadium complexes, amylin antagonists, glucagon antagonists, gluconeogenesis inhibitors, somatostatin analogs, antilipolytic agents, nicotinic acid, acipimox, pramlintide (Symlin™), and nateglinide wherein the amounts of the first and second compounds result in a therapeutic effect.

A preferred aspect of the above methods is wherein the second compound is chlorpropamide, glibenclamide, tolbutamide, tolazamide, acetohexamide, Glypizide®, glimepiride, repaglinide, meglitinide, metformin, phenformin, buformin, midaglizole, isaglidole, deriglidole, idazoxan, efaroxan, fluparoxan, ciglitazone, pioglitazone, englitazone, darglitazone, clomoxir or etomoxir.

A particularly preferred aspect of the above methods is wherein the second compound is glibenclamide, Glypizide®, glimepiride, repaglinide, metformin, or pioglitazone.

Yet another aspect of this invention is kits comprising:

a. a first compound, said first compound being a Formula I compound, a prodrug thereof, or a pharmaceutically acceptable salt of said compound or of said prodrug and a pharmaceutically acceptable vehicle, diluent or carrier in a first unit dosage form;

b. a second compound, said second compound being a diabetic treating agent selected from aldose reductase inhibitors, glucocorticoid receptor antagonists, glycogenolysis inhibitors, glycogen phosphorylase inhibitors, sorbitol dehydrogenase inhibitors, insulin, insulin analogs, insulinotropin, sulfonylureas and analogs, biguanides, imidazolines, insulin secretagogues, linogliride, glitazones, glucosidase inhibitors, acarbose, miglitol, emiglitate, voglibose, camiglibose, β-agonists, phosphodiesterase inhibitors, vanadate, vanadium complexes (e.g. Naglivan®), peroxovanadium complexes, amylin antagonists, glucagon antagonists, gluconeogenesis inhibitors, somatostatin analogs, antilipolytic agents, nicotinic acid, acipimox, pramlintide (Symlin™), and nateglinide and a pharmaceutically acceptable vehicle, diluent or carrier in a second unit dosage form; and c. means for containing said first and second dosage forms wherein the amounts of the first and second compounds result in a therapeutic effect.

A preferred second compound is chlorpropamide, glibenclamide, tolbutamide, tolazamide, acetohexamide, Glypizide®, glimepiride, repaglinide, meglitinide, metformin, phenformin, buformin, midaglizole, isaglidole, deriglidole, idazoxan, efaroxan, fluparoxan, ciglitazone, pioglitazone, englitazone, darglitazone, clomoxir or etomoxir.

A particularly preferred second compound is glibenclamide, Glypizide®, glimepiride, repaglinide, mefformin, or pioglitazone.

This invention is also directed to pharmaceutical combination compositions comprising: a therapeutically effective amount of a composition comprising a first compound, said first compound being a Formula I compound, a prodrug thereof, or a pharmaceutically acceptable salt of said compound or of said prodrug;

a second compound, said second compound being phenylpropanolamine, ephedrine, pseudoephedrine, phentermine, a neuropeptide Y antagonist, a β₃-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, the OB protein, a leptin analog, a leptin receptor agonist, a galanin antagonist, a lipase inhibitor, a bombesin agonist, a neuropeptide-Y antagonist, thyroxine, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, or a ciliary neurotrophic factor; and/or optionally a pharmaceutical vehicle, diluent or carrier.

Preferred among the second compounds are orlistat, sibutramine, or bromocriptine.

Another aspect of this invention is methods for treating obesity in a mammal comprising administering to a mammal suffering from obesity a first compound, said first compound being a Formula I compound a prodrug thereof, or a pharmaceutically acceptable salt of said compound or of said prodrug; and a second compound, said second compound being phenylpropanolamine, ephedrine, pseudoephedrine, phentermine, a neuropeptide Y antagonist, a $\beta_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, the OB protein, a leptin analog, a leptin receptor agonist, a galanin antagonist, a lipase inhibitor, a bombesin agonist, a neuropeptide-Y antagonist, thyroxine, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, or a ciliary neurotrophic factor wherein the amounts of the first and second compounds result in a therapeutic effect.

A preferred aspect of the above methods is wherein the second compound is orlistat, sibutramine or bromocriptine.

Yet another aspect of this invention is kits comprising:
a. a first compound, said first compound being a Formula I compound, a prodrug thereof, or a pharmaceutically acceptable salt of said compound or of said prodrug and a pharmaceutically acceptable carrier, vehicle or diluent in a first unit dosage form;
b. a second compound, said second compound being phenylpropanolamine, ephedrine, pseudoephedrine, phentermine, a neuropeptide Y antagonist, a $\beta_3$-adrenergic receptor agonist, a cholecystokinin-A agonist, a monoamine reuptake inhibitor, a sympathomimetic agent, a serotoninergic agent, a dopamine agonist, a melanocyte-stimulating hormone receptor agonist or mimetic, a melanocyte-stimulating hormone receptor analog, a cannabinoid receptor antagonist, a melanin concentrating hormone antagonist, leptin, the OB protein, a leptin analog, a leptin receptor agonist, a galanin antagonist, a lipase inhibitor, a bombesin agonist, a neuropeptide-Y antagonist, thyroxine, a thyromimetic agent, dehydroepiandrosterone or an analog thereof, a glucocorticoid receptor modulator, an orexin receptor antagonist, a urocortin binding protein antagonist, a glucagon-like peptide-1 receptor agonist, and a ciliary neurotrophic factor or a pharmaceutically acceptable vehicle, diluent or carrier in a second unit dosage form; and
c. a container for said first and second dosage forms wherein the amounts of the first and second compounds result in a therapeutic effect.

A preferred second compound is orlistat, sibutramine or bromocriptine.

This invention is also directed to pharmaceutical combination compositions comprising: a therapeutically effective amount of a composition comprising
a first compound, said first compound being a Formula I compound, a prodrug thereof, or a pharmaceutically acceptable salt of said compound or of said prodrug;
a second compound, said second compound being an anti-hypertensive agent; and/or optionally
a pharmaceutical vehicle, diluent or carrier.

Preferred anti-hypertensive agents are a calcium channel blocker, an angiotensin converting enzyme (ACE) inhibitor or a diuretic.

Another aspect of this invention is methods for treating hypertension in a mammal comprising administering to a mammal suffering from hypertension a first compound, said first compound being a Formula I compound a prodrug thereof, or a pharmaceutically acceptable salt of said compound or of said prodrug; and
a second compound, said second compound being an antihypertensive agent wherein the amounts of the first and second compounds result in a therapeutic effect.

Preferred anti-hypertensive agents are a calcium channel blocker, an angiotensin converting enzyme (ACE) inhibitor or a diuretic.

Yet another aspect of this invention is kits comprising:
a. a first compound, said first compound being a Formula I compound, a prodrug thereof, or a pharmaceutically acceptable salt of said compound or of said prodrug and a pharmaceutically acceptable carrier, vehicle or diluent in a first unit dosage form;
b. a second compound, said second compound being an anti-hypertensive agent and a pharmaceutically acceptable vehicle, diluent or carrier in a second unit dosage form; and
c. means for containing said first and second dosage forms wherein the amounts of the first and second compounds result in a therapeutic effect.

Preferred anti-hypertensive agents are a calcium channel blocker, an angiotensin converting enzyme (ACE) inhibitor or a diuretic.

The term "treating", "treat" or "treatment" as used herein includes preventative (e.g., prophylactic) and palliative treatment.

By "pharmaceutically acceptable" is meant the carrier, diluent, excipients, and/or salt must be compatible with the other ingredients of the formulation, and not deleterious to the recipient thereof.

Syndrome X refers to a common clinical disorder that is defined as the presence of increased insulin concentrations in association with other disorders including viceral obesity, hyperlipidemia, dyslipidemia, hyperglycemia, hypertension, and potentially hyperuricemis and renal dysfunction.

The expression "prodrug" refers to compounds that are drug precursors which, following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the Formula I compounds include but are not limited to those having a carboxyl moiety wherein the free hydrogen is replaced by $(C_1-C_4)$alkyl, $(C_2-C_7)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$ alkyl (such as β-dimethylaminoethyl), carbamoyl-$(C_1-C_2)$ alkyl, N,N-di$(C_1-C_2)$alkylcarbamoyl-$(C_1-C_2)$alkyl and piperidino-, pyrrolidino- or morpholino$(C_2-C_3)$alkyl.

The following paragraphs describe exemplary ring(s) for the generic ring descriptions contained herein.

Exemplary five to six membered aromatic rings optionally having one or two heteroatoms selected independently from oxygen, nitrogen and sulfur include phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl and pyrazinyl.

Exemplary partially saturated, fully saturated or fully unsaturated five to eight membered rings optionally having one to four heteroatoms selected independently from oxygen, sulfur and nitrogen include cyclopentyl, cyclohexyl, cycloheptyl, cyclooctyl and phenyl. Further exemplary five membered rings include 2H-pyrrolyl, 3H-pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 1,3,4-thiadiazolyl, 1,2,3,4-oxatriazolyl, 1,2,3,5-oxatriazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Further exemplary six membered rings include 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl.

Further exemplary seven membered rings include azepinyl, oxepinyl, and thiepinyl.

Further exemplary eight membered rings include cyclooctyl, cyclooctenyl and cyclooctadienyl.

Exemplary bicyclic rings consisting of two fused partially saturated, fully saturated or fully unsaturated five or six membered rings, taken independently, optionally having one to four heteroatoms selected independently from nitrogen, sulfur and oxygen include indolizinyl, indolyl, isoindolyl, 3H-indolyl, 1H-isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, 7-bicyclo[4.2.0]octa-1,3,5 trienyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

By alkylene is meant saturated hydrocarbon (straight chain or branched) wherein a hydrogen atom is removed from each of the terminal carbons. Exemplary of such groups (assuming the designated length encompasses the particular example) are methylene, ethylene, propylene, butylene, pentylene, hexylene, heptylene).

By halo is meant chloro, bromo, iodo, or fluoro.

By alkyl is meant straight chain saturated hydrocarbon or branched chain saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By alkoxy is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

As used herein the term mono-N— or di-N,N—$(C_1-C_x)$alkyl . . . refers to the $(C_1-C_x)$alkyl moiety taken independently when it is di-N,N—$(C_1-C_x)$alkyl . . . (x refers to integers).

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

References (e.g., claim 1) to "said carbon" in the phrase "said carbon is optionally mono-, di- or tri-substituted independently with halo, said carbon is optionally mono-substituted with hydroxy, said carbon is optionally mono-substituted with oxo" refers to each of the carbons in the carbon chain including the connecting carbon.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluene-sulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

As used herein, the expressions "reaction-inert solvent" and "inert solvent" refers to a solvent or a mixture thereof which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates and solvates of the compounds of this invention are also included.

The subject invention also includes isotopically-labeled compounds, which are structurally identical to those disclosed herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

All patents and patent applications referred to herein are hereby incorporated by reference.

DTT means dithiothreitol. DMSO means dimethyl sulfoxide. EDTA means ethylenediamine tetraacetic acid.

Other features and advantages of this invention will be apparent from this description and the appendant claims which describe the invention.

DETAILED DESCRIPTION OF THE INVENTION

In general the compounds of this invention can be made by processes which include processes analogous to those known in the chemical arts, particularly in light of the description contained herein. Certain processes for the manufacture of the compounds of this invention are provided as further features of the invention and are illustrated by the following reaction schemes. Other processes are described in the experimental section.

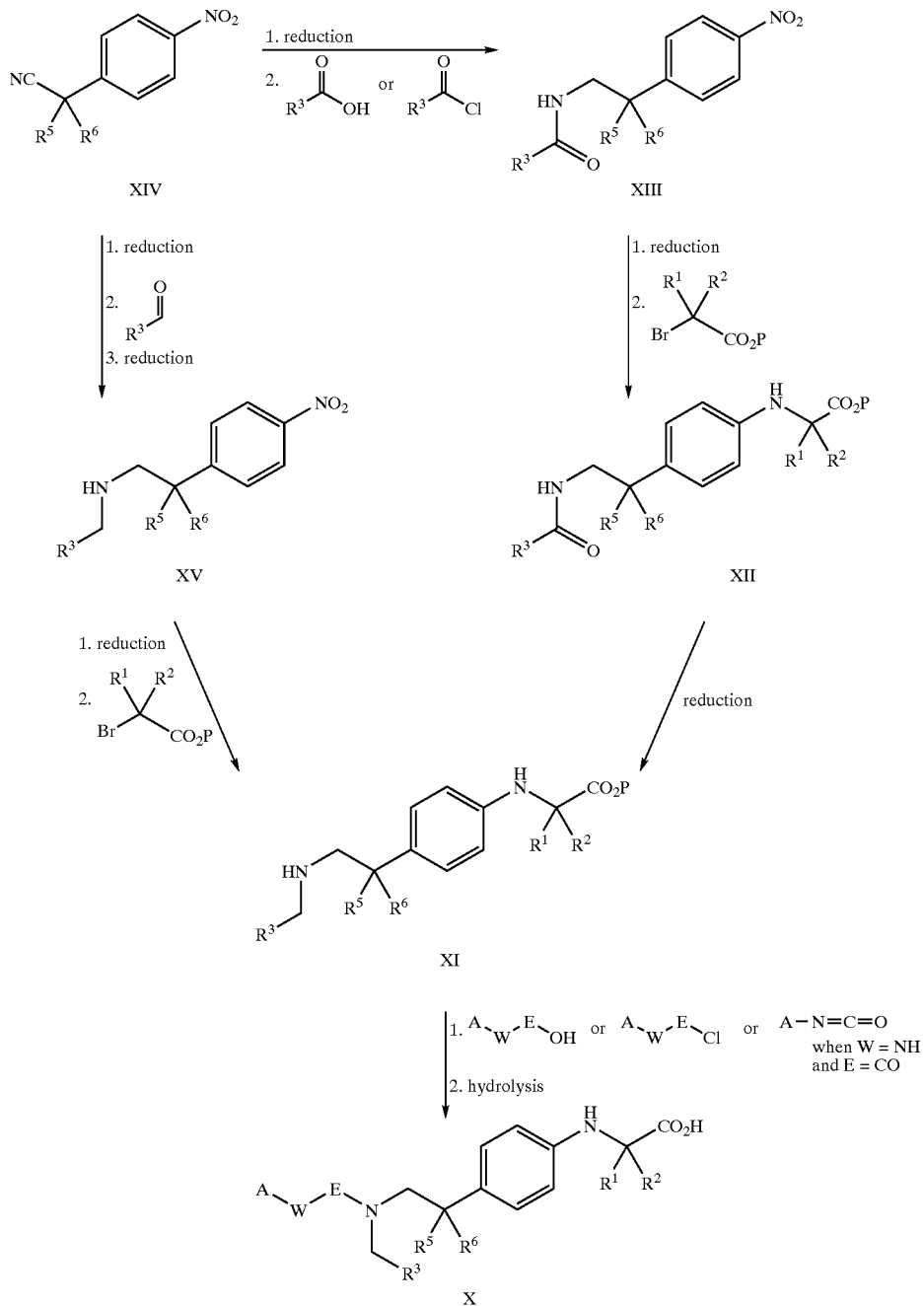

SCHEME I

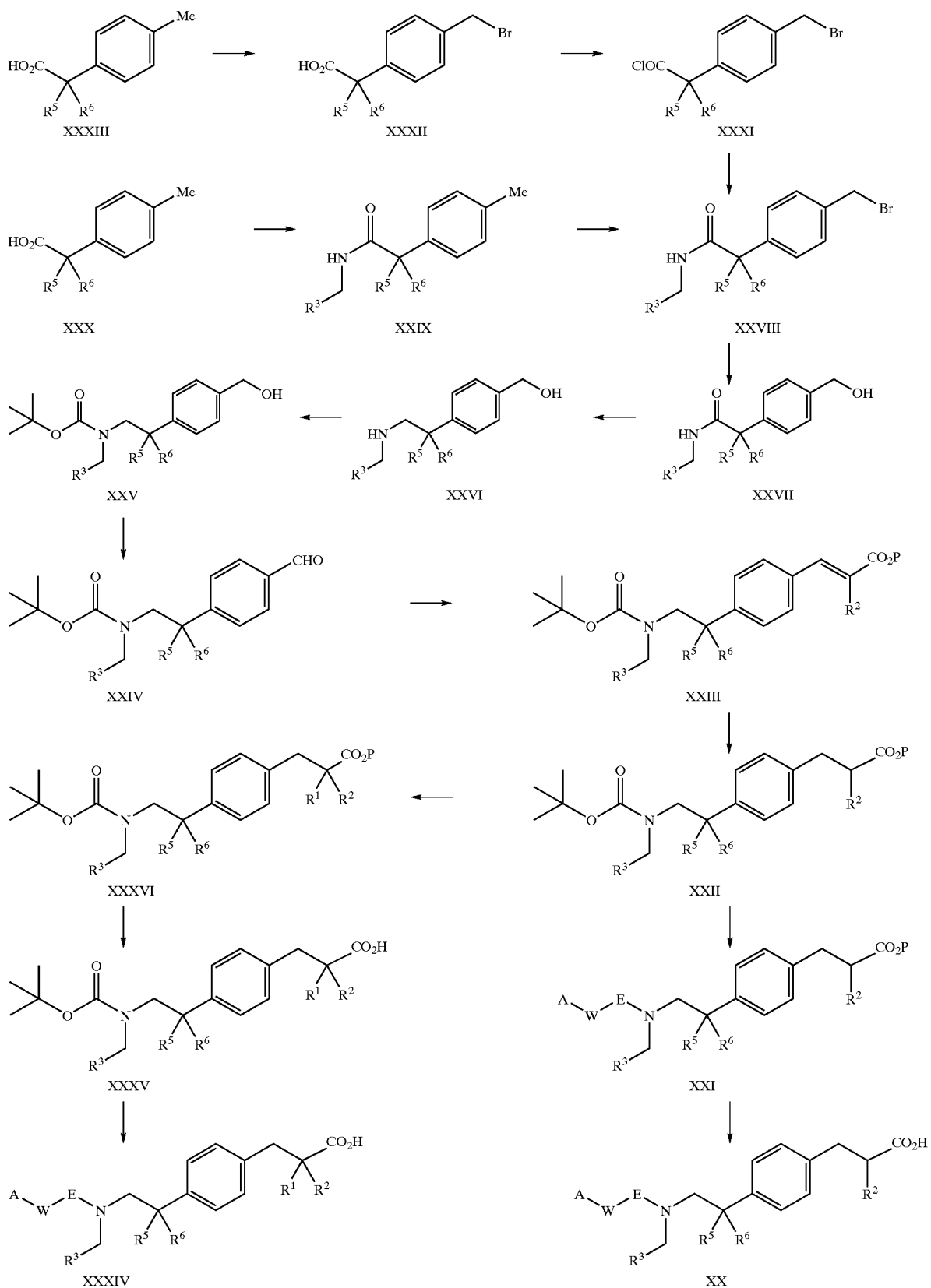
SCHEME II

SCHEME III
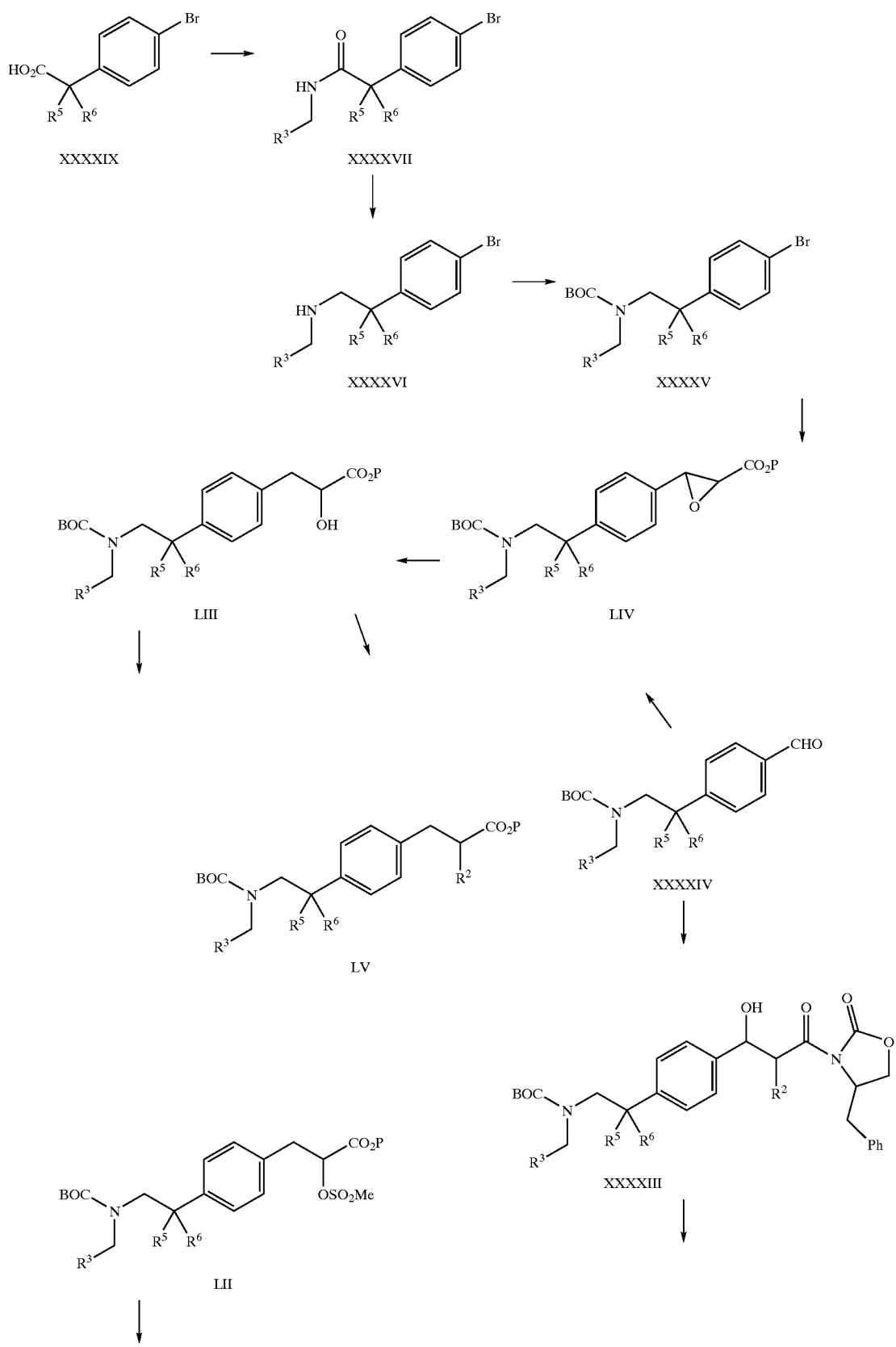

-continued
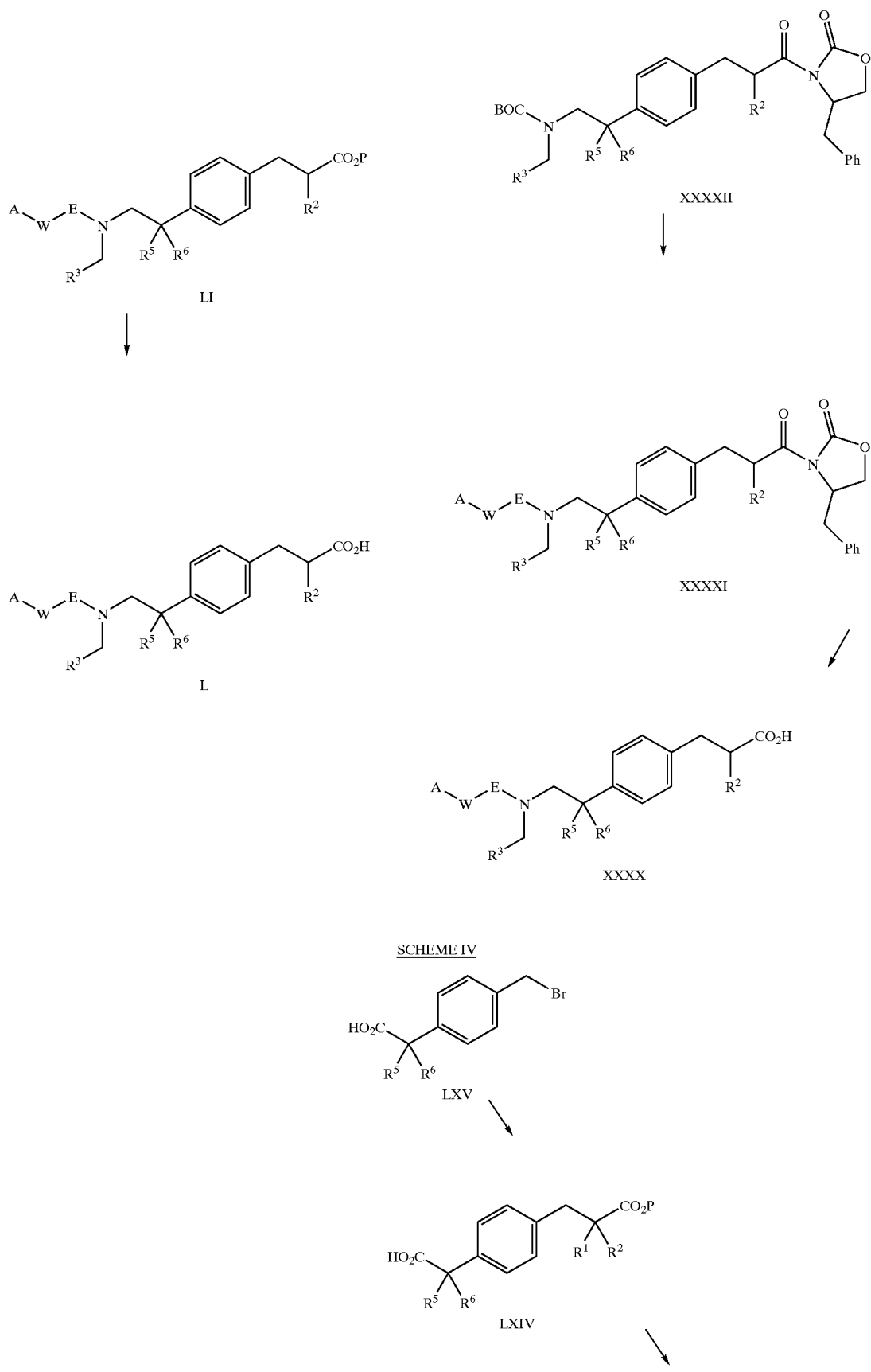
SCHEME IV

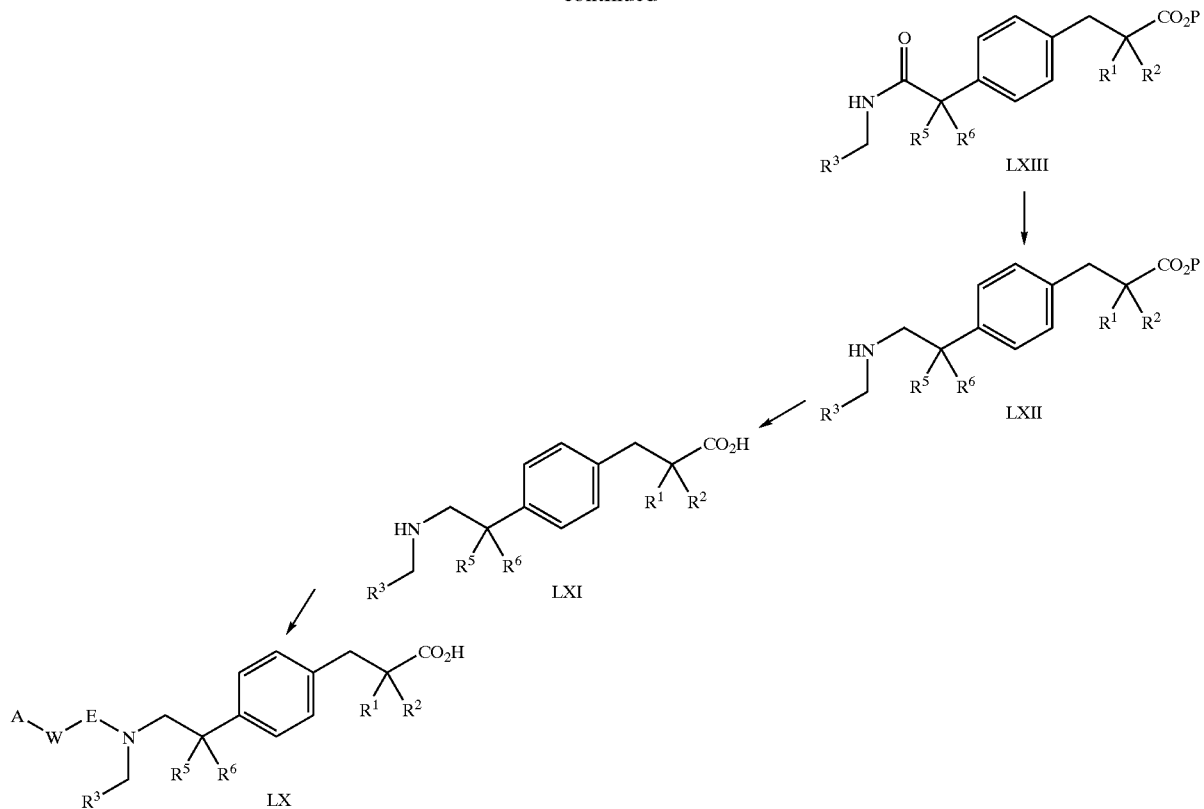

As an initial note, in the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, in Reaction Schemes I and II certain Formula I compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl, benzyloxycarbonyl, and 9-fluorenylmethylenoxycarbonyl for amines and lower alkyl or benzyl esters for carboxylic acids) which are generally not chemically reactive under the reaction conditions described and can typically be removed without chemically altering other functionality in the Formula I compound.

According to reaction Scheme I the desired Formula I compounds wherein $R^1$, $R^2$, $R^3$, $R^5$, $R^6$, A, W and E are as described above, B is NH, and and Z is carboxyl (depicted as Formula X compounds) may be prepared by acylating the corresponding Formula XI with an acyl chloride, sulfonyl chloride, isocyanate or carboxylic acid, followed by optional hydrolysis of the resulting compound to remove the carboxyl protecting group P (T. W. Greene, *Protective Groups in Organic Synthesis*) to produce the corresponding carboxylic acid. Alternatively, the hydrolysis may be omitted when the ester is a suitable prodrug for the carboxylic acid.

Generally, the desired Formula XI compounds may be acylated with the appropriate acyl chloride or the appropriate sulfonyl chloride in a reaction-inert solvent such as methylene chloride in the presence of an amine base such as triethylamine at a temperature of about 10° C. to about 50° C., typically ambient for about 6 to about 18 hours; with the appropriate isocyanate in a reaction-inert solvent such as toluene in the presence of a tertiary amine base such as Hunig's base at a temperature of about 10° C. to about 110° C., typically ambient for about 6 to about 18 hours; or with the appropriate carboxylic acid in a reaction-inert solvent such as methylene chloride in the presence of a carbodiimide (e.g., 1-(3-dimethylaminopropyl)-3-ethylcarbodiimide hydrochloride) at a temperature of about 100° C. to about 50° C., typically ambient for about 6 to about 24 hours. The ester moiety can then be hydrolyzed in an aqueous alcoholic solvent such as methanol/water with a base such as potassium carbonate at a temperature of about 40° C. to about 80° C., preferably at reflux, for about 2 hours to about 18 hours to provide the Formula X compounds wherein Z is carboxyl. Alternatively, the protecting group P in some instances can be removed by hydrogenation (or transfer hydrogenation) preferably at atmospheric pressure over a catalyst such as 10% palladium on carbon in a polar solvent such as methanol at ambient temperature for a period of about 1 hour to about 24 hours.

The desired Formula XI compounds wherein $R^1$, $R^2$, $R^3$, $R^5$ and $R^6$ are as described above, and P is a known carboxyl protecting group may be prepared by reduction of the corresponding Formula XII compounds. Generally, the Formula XII compound is combined with a reducing agent such as borane-tetrahydrofuran complex in a polar solvent such as tetrahydrofuran at a temperature of about 100° C. to about 100° C., typically ambient, for about 6 to about 18 hours.

The desired Formula XII compounds wherein $R^1$, $R^2$, $R^3$, $R^5$ and $R^6$ are as described above, and P is a known carboxyl protecting group may be prepared by reduction of the corresponding Formula XII compounds, followed by alkylation of the resulting aniline moiety. Generally, the Formula XIII compound is combined with a reducing agent such as hydrogen and a catalyst such as 10% palladium on carbon preferably under atmospheric pressure in a polar solvent such as methanol at ambient temperature for a period of about 1 hour to about 8 hours. The resulting aniline is then combined with the appropriate alkyl haloalkylcarboxylate in the presence of a base such as cesium carbonate in a polar solvent such as dimethylformamide at a temperature of about 100° C. to about 100° C., typically ambient, for about 2 to about 18 hours.

The desired Formula XII compounds wherein $R^3$, $R^5$ and $R^6$ are as described above may be prepared from the corresponding Formula XIV compounds by reduction followed by acylation. Generally, the Formula XIV compound is combined with a reducing agent such as borane-tetrahydrofuran complex in a polar solvent such as tetrahydrofuran at a temperature of about 10° C. to about 100° C., typically ambient, for about 6 to about 24 hours. The resulting amine is then combined with the appropriate acyl chloride in a reaction-inert solvent such as methylene chloride in the presence of an amine base such as triethylamine at a temperature of about 10° C. to about 50° C., typically ambient for about 6 to about 18 hours, or with the appropriate carboxylic acid in a reaction-inert solvent such as methylene chloride in the presence of a carbodiimide (e.g., 1-(3-dimethylaminopropyl)-3-ethylcarbodiimide hydrochloride) at a temperature of about 10° C. to about 50° C., typically ambient for about 6 to about 24 hours.

Alternatively, the desired Formula XI compounds wherein $R^1$, $R^2$, $R^3$, $R^5$ and $R^6$ are as described above, and P is a known carboxyl protecting group may be prepared by reduction of the corresponding Formula XV compounds, followed by alkylation of the resulting aniline moiety, as described above for preparation of the Formula XII compounds.

The desired Formula XV compounds wherein $R^3$, $R^5$ and $R^6$ are as described above may be prepared from the corresponding Formula XIV compounds by reduction of the nitrile functionality followed by reductive amination on the resulting amine. Generally, the Formula XIV compound is combined with a reducing agent such as borane-tetrahydrofuran complex in a polar solvent such as tetrahydrofuran at a temperature of about 10° C. to about 100° C., typically ambient, for about 6 to about 24 hours. The resulting amine is then combined with the appropriate aldehyde in a polar solvent such as ethanol in the presence of a Lewis acid such as titanium isopropoxide at a temperature of about 10° C. to about 50° C., typically ambient for about 6 to about 18 hours. A reducing agent such as sodium borohydride is then added to the resulting imine and the resulting reaction mixture stirred at a temperature of about 10° C. to about 50° C., typically ambient for about 6 to about 24 hours.

According to reaction Scheme II the desired Formula I compounds wherein $R^3$, $R^5$, $R^6$, A, W and E are as described above, B is $CH_2$, $R^1$ is H and $R^2$ is as described above where the first carbon atom of the chain is replaced with an oxygen atom and Z is carboxyl (depicted as Formula XX compounds) may be prepared by deprotection of the compound of Formula XXI by treatment with a suitable base such as potassium carbonate or lithium hydroxide typically in a mixture of water and an organic cosolvent such as tetrahydrofuran or dioxane at a temperature of about 25° C. to 80° C. for a period of about 1 to about 7 days. If the protecting group P is benzyl, this may alternatively be removed by hydrogenation in a reaction inert solvent with a catalyst such as palladium on carbon, or by transfer hydrogenation using ammonium formate in refluxing methanol in the presence of a catalyst such as palladium on carbon in a reaction inert solvent such as methanol or ethanol at a temperature between about 0° C. to about 80° C., typically 25° C. to 50° C. If the protecting group P is t-butyl, this may be removed by treatment with trifluoroacetic acid in a solvent such as methylene chloride at a temperature between about 0° C. to about 80° C., typically ambient. This acid may subsequently be converted into a salt with a strong base as described below. Optionally the hydrolysis may be omitted when the ester is a suitable prodrug for the carboxylic acid.

The desired Formula XXI compounds wherein $R^3$, $R^5$, $R^6$, A, W and E are as described above, and $R^2$ is as described in the preceding paragraph may be prepared from the corresponding Formula XXII compounds by removal of the t-butylcarbamate protecting group. A suitable method of deprotection is treatment with trifluoroacetic acid, either neat or diluted in an inert solvent at a temperature of about 0° C. to about 25° C. for a period of about 10 minutes to 3 hours. Alternatively the t-butylcarbamate group may be removed by treatment with anhydrous hydrogen chloride in an inert solvent such as ethyl acetate at a temperature of about −78° C. to about 25° C. The amine or its salt is combined with the appropriate acyl chloride, sulfonyl chloride, carbamoyl chloride or isocyanate in a suitable inert solvent such as methylene chloride or chloroform containing a suitable base such as triethylamine or diisopropylethylamine at a temperature between about 0° C. and about 50° C. typically 25° C. for a period of about 1 to about 18 hours or with the appropriate carboxylic acid in a reaction-inert solvent such as methylene chloride in the presence of a carbodiimide (e.g., 1-(3-dimethylaminopropyl)-3-ethylcarbodiimide hydrochloride) at a temperature of about 10° C. to about 50° C., typically ambient for about 6 to about 24 hours.

The desired Formula XXII compounds wherein $R^3$, $R^5$, and $R^6$ are as described above, and $R^2$ is as described for the Formula XX compound, may be prepared from the corresponding Formula XXIII compounds by reduction. This may be achieved by hydrogenation in the presence of a suitable catalyst such as palladium supported on carbon 5–10% w/w under a hydrogen pressure equal to 15–50 p.s.i. for a period of about 2 to about 24 hours. Alternatively the reduction may be carried out in a suitable alcohol solvent, preferably methanol in the presence of magnesium metal which dissolves in the course of the reaction. Under these conditions the reduction may be accompanied by a transesterification with the alcohol solvent. The outcome of the subsequent reactions is typically unaffected by this change.

The desired Formula XXIII compounds wherein $R^3$, $R^5$, and $R^6$ are as described above, and $R^2$ is as described for the Formula XX compound, may be prepared from the corresponding Formula XXIV compounds by a Wittig-Horner reaction. The Wittig-Horner reagent required is a 2-diphenylphosphinoyl-2-alkoxyacetic acid ester prepared by heating a mixture of the dialkoxyacetic acid ester and chlorodiphenylphosphine. A mixture of this reagent with a compound of Formula XXIV in a reaction inert solvent such as tetrahydrofuran is treated with a base such as sodium hydride at a temperature between about −78° C. and room temperature and the mixture brought to reflux if necessary for a period of about 10–60 minutes to complete the reaction.

The desired aldehyde of Formula XXIV wherein $R^3$, $R^5$, and $R^6$ are as described above may be prepared from the benzyl alcohol of Formula XXV by treatment with an appropriate oxidizing agent such as manganese dioxide in a suitable inert solvent such as ether for a period of about 1 to 12 hours at room temperature or with a combination of oxalyl chloride and dimethylsulfoxide under typical Swern oxidation conditions as described by M. Marx and T. T. Tidwell in J. Org. Chem., 1984, 49, 788.

The desired compound of Formula XXV wherein $R^3$, $R^5$, and $R^6$ are as described above may be prepared from the compound of Formula XXVI by treatment with a t-butylcarbonylating agent such as di-t-butyl dicarbonate in a suitable solvent such as tetrahydrofuran or dioxane in the presence of aqueous sodium hydrogen carbonate and controlling the pH of the mixture to about pH 8 to 9 by addition of aqueous sodium hydroxide solution during the course of the reaction.

The desired compound of Formula XXVI wherein $R^3$, $R^5$, and $R^6$ are as described above may be prepared from the compound of Formula XXVII by treatment with a reducing agent such as lithium aluminum hydride or diborane in tetrahydrofuran. The diborane may be obtained commercially in solution or conveniently prepared in situ by mixing a suspension of sodium borohydride in THF with boron trifluoride etherate at about 0° C. The reduction is accomplished by heating the mixture under reflux for a period of about 1–24 hours and then decomposing the boron complex by treatment with a mineral acid such as hydrochloric acid.

The desired compound of Formula XXVII wherein $R^3$, $R^5$, and $R^6$ are as described above may be prepared from the compound of Formula XXVIII by treatment with a water-dioxane mixture in the presence of a mild base such as calcium carbonate under reflux for a period of about 1–10 hours.

The desired compound of Formula XXVIII wherein $R^3$, $R^5$, and $R^6$ are as described above may be prepared from the compound of Formula XXXII by treatment with thionyl chloride to produce the acid chloride of Formula XXXI and subsequent treatment with the appropriate primary amine $R^3CH_2NH_2$ wherein $R^3$ is as described above in the presence of a suitable base such as triethylamine in a suitable inert solvent at a temperature between about 0° C. and about 50° C. typically 25° C. for a period of about 1 to 12 hours.

The desired compound of Formula XXXII wherein $R^5$ and $R^6$ are as described above may be prepared from the compound of Formula XXXIII by treatment with a brominating agent such as N-bromosuccinimide or bromine in an inert solvent such as tetrachloromethane in the presence of a light source which is also used to maintain the reaction mixture at reflux.

In another aspect of Scheme II the desired compounds of Formula I wherein $R^1$ is as described above (except for H), A, W, E, $R^3$, $R^5$ and $R^6$ are as described above, B is $CH_2$, and $R^2$ is as described above where the first carbon atom of the chain is replaced with an oxygen atom and Z is carboxyl (depicted as Formula XXXIV compounds) may be prepared from the corresponding compound of Formula XXXV by removal of the t-butylcarbamate group followed by acylation with an acyl chloride, carbamoyl chloride, isocyanate or sulfonyl chloride in the presence of an organic base as described above. A suitable method of deprotection is treatment with trifluoroacetic acid, either neat or diluted in an inert solvent at a temperature of about 0° C. to about 25° C. for a period of about 10 minutes to about 3 hours. Alternatively the t-butylcarbamate group may be removed by treatment with anhydrous hydrogen chloride in a suitable inert solvent such as ethyl acetate at a temperature of about −78° C. to about 25° C. The amine or its salt is combined with the appropriate acyl chloride, sulfonyl chloride, carbamoyl chloride or isocyanate in a suitable inert solvent such as methylene chloride or chloroform containing a suitable base such as triethylamine or diisopropylethylamine to provide the desired product of Formula XXXIV.

The desired compounds of Formula XXXV wherein $R^1$ is alkyl or aralkyl, $R^3$, $R^5$, and $R^6$ are as described above, and $R^2$ is as described for the Formula XXXIV compound may be prepared by deprotection of the compound of Formula XXXVI by treatment with a base such as lithium hydroxide typically in a mixture of water and an organic cosolvent such as tetrahydrofuran or dioxane at a temperature of about 25° C. to about 80° C. for a period of about 1 to about 7 days. The hydrolysis step typically requires longer than with the less hindered Formula XXI compounds. If the protecting group P is benzyl, this may alternatively be removed by hydrogenation in a reaction inert solvent with a catalyst such as palladium on carbon, or by transfer hydrogenation using ammonium formate in refluxing methanol in the presence of a catalyst such as palladium on carbon in a reaction inert solvent such as methanol or ethanol at a temperature between about 0° C. to about 80° C., typically about 25° C. to about 50° C. If the protecting group P is t-butyl, this may be removed by treatment with trifluoroacetic acid in a solvent such as methylene chloride at a temperature between about 0° C. to about 80° C., typically ambient. This acid may subsequently be converted into a salt with a strong base as described above. This hydrolysis may be omitted when the ester is a suitable prodrug for the carboxylic acid as appropriate.

Desired compounds of Formula XXXVI wherein $R^1$ is alkyl or aralkyl, $R^3$, $R^5$, and $R^6$ are as described above and $R^2$ is described for the Formula XXXIV compound may be prepared from the corresponding compound of Formula XXII by treatment with a strong base such as lithium hexamethyldisilazide in an inert solvent such as tetrahydrofuran preferably at about −78° C. for a period of about 30 minutes to 24 hours. The appropriate alkylating agent such as an alkyl bromide or iodide is then added and the reaction allowed to proceed for about 1–24 hours at a temperature of about −78° C. to 25° C.

In another aspect of Scheme II the desired compounds of Formula XXVIII may be prepared from the compound of Formula XXIX by treatment with a brominating agent such as N-bromosuccinimide or bromine in an inert solvent such as tetrachloromethane in the presence of a light source which is also used to maintain the reaction mixture at reflux.

The desired compound of Formula XXIX wherein $R^3$, $R^5$ and $R^6$ are as described above may be prepared from the compound of Formula XXX by treatment with thionyl chloride and subsequent treatment with the appropriate primary amine $R^3CH_2NH_2$ wherein $R^3$ is as described above in the presence of a suitable base such as triethylamine in a suitable inert solvent for a period of about 1 to 12 hours at room temperature.

According to reaction Scheme III an alternative method to prepare the desired Formula I compounds wherein $R^3$, $R^5$, $R^6$, A, W and E are as described above, B is $CH_2$, $R^1$ is H and $R^2$ is as described above for Formula XXXIV compounds where the first carbon atom of the chain is replaced with an oxygen atom and Z is carboxyl (depicted as Formula XXXX compounds), involves hydrolysis of the amide XXXXI to produce the corresponding carboxylic acid, as described above. Optionally, the hydrolysis may be omitted when the amide is a suitable prodrug for the carboxylic acid.

The desired Formula XXXXI compounds wherein $R^3$, $R^5$, $R^6$, A, W and E are as described above and $R^2$ is as described for the Formula XXXX compound may be prepared from the corresponding Formula XXXXII compounds by removal of the secondary amine protecting group followed by acylation with an acyl chloride, carbamoyl chloride, isocyanate or sulfonyl chloride in the presence of an organic base as described above. When t-butylcarbamate protection is used, as illustrated in Scheme III, a suitable method of deprotection is treatment with trifluoroacetic acid, either neat or diluted in an inert solvent at a temperature of about 0° C. to about 25° C. for a period of 10 minutes to 3 hours. Alternatively the t-butylcarbamate group may be removed by treatment with anhydrous hydrogen chloride in a suitable inert solvent such as ethyl acetate at a temperature of about −78° C. to about 25° C. The amine or its salt is combined with the appropriate acyl chloride, sulfonyl chloride, carbamoyl chloride or isocyanate in a suitable inert solvent such as methylene chloride or chloroform containing a suitable base such as triethylamine or diisopropylethylamine to provide the desired product of Formula XXXXI.

The desired Formula XXXXII compounds wherein $R^3$, $R^5$, and $R^6$ are as described above and $R^2$ is as described for the Formula XXXX compound may be prepared from the corresponding compound of Formula XXXXIII by reduction of the hydroxyl group by acylation, for example with acetic anhydride in the presence of a base such as pyridine, followed by hydrogenation in a reaction inert solvent with a catalyst such as palladium on carbon, or by transfer hydrogenation using ammonium formate in refluxing methanol in the presence of a catalyst such as palladium on carbon in a reaction inert solvent such as methanol or ethanol at a temperature between about 0° C. to about 80° C., typically about 25° C. to about 50° C. Alternatively a thionocarbonate may be prepared using an aryl chlorothionoformate in the presence of a base such as pyridine followed by reduction with tri-n-butyltin hydride in a reaction inert solvent such as toluene in the presence of a radical initiator such as azobisisobutyronitrile at an elevated temperature typically about 80° C. to about 110° C. to provide the desired product of Formula XXXXII.

The desired Formula XXXXIII compounds wherein $R^3$, $R^5$, and $R^6$ are as described above and $R^2$ is as described for the Formula XXXX compound are prepared from the corresponding aldehyde of Formula XXXXIV by treatment with the desired 4-benzyl-3-alkoxyacetyl-oxazolidin-2-one in the presence of di-n-butylboron triflate under conditions described by Hulin et. al (J. Med. Chem., 1996, 39, 3897). With the appropriate choice of enantiomerically pure chiral auxiliary the absolute configuration of the two new chiral centers may be controlled.

The desired Formula XXXXIV compounds wherein $R^3$, $R^5$, and $R^6$ are as described above are prepared from the corresponding aryl bromide of Formula XXXXV by treatment with an alkyllithium such as sec-butyllithium in a reaction-inert solvent such as tetrahydrofuran or diethyl ether at a temperature typically about −78° C. followed by treatment with dimethylformamide at a temperature between about −78° C. to 25° C.

The desired Formula XXXXV compounds wherein $R^3$, $R^5$, and $R^6$ are as described above are prepared from a 3-bromophenylacetic acid of Formula XXXXIX by a series of reactions analogous to those described for Scheme II.

In another aspect of Scheme III the desired Formula I compounds wherein $R^3$, $R^5$, $R^6$, A, W and E are as described above, B is $CH_2$, $R^1$ is H and $R^2$ is as described above wherein the first carbon atom of the chain is replaced with a sulfur atom and Z is carboxyl (depicted as Formula L compounds) may be prepared by deprotection of the compound of Formula LI by treatment with a suitable base such as potassium carbonate or lithium hydroxide typically in a mixture of water and an organic cosolvent such as tetrahydrofuran or dioxane at a temperature of about 25° C. to about 80° C. for a period of about 1 to about 7 days. If the protecting group P is t-butyl, this may be removed by treatment with trifluoroacetic acid in a solvent such as methylene chloride at a temperature between about 0° C. to about 80° C., typically ambient. This acid may subsequently be converted into a salt with a strong base as described above. In some cases this hydrolysis may be omitted when the ester is a suitable prodrug for the carboxylic acid.

The desired Formula LI compounds wherein $R^3$, $R^5$, and $R^6$, A, W and E are as described above and R2 is as described for the Formula L compounds, may be prepared from the corresponding Formula LII compounds by substitution of the mesyloxy group with the appropriate thiolate anion, for example by reaction with an alkyl or aryl mercaptan in the presence of a suitable base such as potassium hydroxide or t-butoxide in a reaction inert solvent such as tetrahydrofuran or dimethylformamide at a temperature typically about 0° C. to about 50° C., typically about 25° C. Following this, the secondary amine protecting group is removed followed by acylation with an acyl chloride, carbamoyl chloride isocyanate or sulfonyl chloride in the presence of an organic base by procedures analogous to those described for Scheme II to produce the desired Formula LI compounds.

The desired mesylate of Formula LII wherein $R^3$, $R^5$ and $R^6$ are as described above is prepared from the corresponding compound of Formula LIII by reaction with a suitable mesylating agent such as methanesulfonic anhydride or methanesulfonyl chloride in the presence of a suitable base such as pyridine in a reaction inert solvent such as pyridine, tetrahydrofuran or dimethylformamide at a temperature between about 0° C. to about 50° C., typically about 25° C.

The desired compound of Formula LII wherein $R^3$, $R^5$ and $R^6$ are as described above may be prepared by reduction of the corresponding epoxide of Formula LIV typically by hydrogenation in a reaction inert solvent with a catalyst such as palladium on carbon, or by transfer hydrogenation using ammonium formate in refluxing methanol in the presence of a catalyst such as palladium on carbon in a reaction inert solvent such as methanol or ethanol at a temperature between about 0° C. to about 80° C., typically 25° C. to 50° C.

The desired compound of Formula LIV wherein $R^3$, $R^5$ and $R^6$ are as described above is prepared from the corresponding aldehyde of Formula XXXXIV by a Darzens condensation using a suitable α-haloester such as ethyl-2-chloroacetate in the presence of a suitable base such as sodium hydride in a reaction inert solvent such as tetrahydrofuran at a temperature between about 25° C. to about 80° C., typically at reflux.

In another aspect of Scheme III the desired compounds of Formula LIII wherein $R^3$, $R^5$, and $R^6$ are as described above may be converted to the Formula LV compounds by alkylation with an alkyl or aralkyl bromide or iodide in the presence of cesium hydroxide or cesium carbonate, tetrabutylammonium iodide and molecular sieves as described by Dueno et. al (Tetrahedron Letters 1999, 40, 1843).

According to reaction Scheme IV the desired Formula I compounds wherein $R^1$ and $R^2$ are independently H, alkyl, cycloalkylalkyl or aralkyl as defined above, $R^3$, $R^5$, $R^6$, A, W and E are as described above, B is $CH_2$ and Z is carboxyl (depicted as Formula LX compounds) may be prepared from the corresponding Formula LXI compounds by combining with the appropriate acyl chloride, sulfonyl chloride, carbamoyl chloride or isocyanate in a reaction inert solvent such as methylene chloride or chloroform containing a suitable base such as triethylamine or diisopropylethylamine at a temperature between about 0° C. and about 50° C. typically 25° C. for a period of about 1 to about 18 hours to provide the desired product of Formula LX.

The desired Formula LXI compounds wherein $R^1$, $R^2$, $R^3$, $R^5$ and $R^6$ are as described above may be prepared from the corresponding Formula LXII compounds by treatment with boron tribromide in methylene chloride at a temperature between about −78° C. and about 25° C. for a period of about 1 to about 3 hours. This hydrolysis may be omitted when the ester is a suitable prodrug for the carboxylic add as appropriate.

The desired Formula LXII compounds wherein $R^1$, $R^2$, $R^3$, $R^5$ and $R^6$ are as described above may be prepared from the compound of Formula LXIII by treatment with a reducing agent such as diborane in tetrahydrofuran. The diborane may be obtained commercially in solution or conveniently prepared in situ by mixing a suspension of sodium borohydride in THF with boron trifluoride etherate at 0° C. The reduction is accomplished at a temperature between about 0° C. and about 80° C. typically at reflux for a period of about 1 to about 18 hours and then decomposing the boron complex by treatment with a mineral acid such as hydrochloric acid.

The desired Formula LXIII compounds wherein $R^1$, $R^2$, $R^3$, $R^5$ and $R^6$ are as described above may be prepared from the corresponding compound of Formula LXIV by treatment with thionyl chloride and subsequent treatment with the appropriate primary amine $R^3CH_2NH_2$ wherein $R^3$ is as described above in the presence of a suitable base such as triethylamine in a suitable inert solvent at a temperature between about 0° C. and about 50° C. typically 25° C. for a period of about 1 to about 12 hours. Alternatively the acid may be combined with the amine $R^3CH_2NH_2$ in a reaction-inert solvent such as methylene chloride in the presence of an amine base such as triethylamine at a temperature of about 10° C. to about 50° C., typically ambient for about 6 to about 18 hours in the presence of a carbodiimide (e.g., 1-(3-dimethylaminopropyl)-3-ethylcarbodiimide hydrochloride).

The desired Formula LXIV compounds wherein $R^1$, $R^2$, $R^5$ and $R^6$ are as described above may be prepared from the compound of Formula LXV by reaction with at least two equivalents of the lithium enolate derived from the ester $R_1R_2CHCO_2P$ in a suitable inert solvent such as tetrahydrofuran at a temperature between about −78° C. and about 25° C. for a period of about 1 to about 24 hours. The lithium enolate is prepared from the corresponding ester by treatment with a suitable base such as lithium hexamethyldisilazide in tetrahydrofuran at about −78° C. for a period of about 1 to about 3 hours.

The desired Formula I compound wherein Z is tetrazol-5-yl may be prepared from the corresponding Formula I compound wherein Z is carboxyl by converting the carboxyl group to a carboxamide group (Z=$CONH_2$), dehydrating the carboxamide to the nitrile (Z=CN) and reacting the nitrile with an appropriate azide to form the tetrazole group.

Generally, the acid is converted to the imidazolide by reaction with carbonyl diimidazole in an aprotic solvent such as methylene chloride at a temperature of about 150° C. to about 40° C. for about 30 minutes to about 4 hours, conveniently at room temperature for about 1 hour. The resulting imidazolide is converted to the corresponding amide by bubbling ammonia gas into the reaction mixture at a temperature of about 10° C. to about 40° C. for about 3 minutes to about 30 minutes, preferably at room temperature for about 5 minutes or until the reaction is complete by TLC analysis. The amide is converted to the nitrile by treatment with trifluoroacetic anhydride and triethylamine in an inert solvent such as methylene chloride at about 0° C. for about 25 minutes to about 2 hours, preferably 30 minutes. Treatment of the nitrile with sodium azide and ammonium chloride in dimethylformamide at a temperature of about 90° C. to about 130° C. for about 7 hours to about 60 hours, preferably at a temperature of 120° C. for 24 hours, yields the desired tetrazole.

The desired Formula I compound wherein Z is 4,5-dihydro-5-oxo-1,2,4-oxadiazol-3-yl may be prepared from the corresponding Formula I compound wherein Z is CN by converting the nitrile to the amide oxime and reacting the amide oxime with a carbonylating agent to form the corresponding 4,5-dihydro-5-oxo-1,2,4-oxadiazole derivative.

Generally, the nitrile is converted to the amide oxime by reaction with hydroxylamine hydrochloride in the presence of a base such as potassium carbonate in an alcoholic solvent at a temperature of about 60° C. to about 110° C. for about 5 hours to about 24 hours, preferably in refluxing ethanol for about 18 hours. The amide oxime is converted to the corresponding 4,5-dihydro-5-oxo-1,2,4-oxadiazole derivative by reaction with carbonyldiimidazole and triethylamine in refluxing ethyl acetate for about 24 hours.

Prodrugs of the compounds of Formula I may be prepared according to methods analogous to those known to those skilled in the art. Exemplary processes are described below.

Prodrugs of this invention where a carboxyl group in a carboxylic acid of Formula I is replaced by an ester may be prepared by combining the carboxylic acid with the appropriate alkyl halide in the presence of a base such as potassium carbonate in an inert solvent such as dimethylformamide at a temperature of about 0° C. to about 100° C. for about 1 to about 24 hours. Alternatively, the acid is combined with an appropriate alcohol as solvent in the presence of a catalytic amount of acid such as concentrated sulfuric acid at a temperature of about 20° C. to about 100° C., preferably at a reflux, for about 1 hour to about 24 hours. Another method is the reaction of the acid with a stoichiometric amount of the alcohol in the presence of a catalytic amount of acid in an inert solvent such as toluene or tetrahydrofuran, with concomitant removal of the water being produced by physical (e.g., Dean-Stark trap) or chemical (e.g., molecular sieves) means.

Prodrugs of this invention where an alcohol function has been derivatized as an ether may be prepared by combining the alcohol with the appropriate alkyl bromide or iodide in the presence of a base such as potassium carbonate in an inert solvent such as dimethylformamide at a temperature of about 0° C. to about 100° C. for about 1 to about 24 hours. Alkanoylaminomethyl ethers may be obtained by reaction of the alcohol with a bis-(alkanoylamino)methane in the presence of a catalytic amount of acid in an inert solvent such as tetrahydrofuran, according to a method described in U.S. Pat. No. 4,997,984. Alternatively, these compounds may be prepared by the methods described by Hoffman et al. in J. Org. Chem. 1994, 59, 3530.

Glycosides are prepared by reaction of the alcohol and a carbohydrate in an inert solvent such as toluene in the presence of acid. Typically the water formed in the reaction is removed as it is being formed as described above. An alternate procedure is the reaction of the alcohol with a suitably protected glycosyl halide in the presence of base followed by deprotection.

N-(1-Hydroxyalkyl) amides and N-(1-hydroxy-1-(alkoxycarbonyl)methyl) amides may be prepared by the reaction of the parent amide with the appropriate aldehyde under neutral or basic conditions (e.g., sodium ethoxide in ethanol) at temperatures between about 25° C. and about 70° C. N-Alkoxymethyl or N-1-(alkoxy)alkyl derivatives can be obtained by reaction of the N-unsubstituted compound with the necessary alkyl halide in the presence of a base in an inert solvent.

The compounds of this invention may also be used in conjunction with other pharmaceutical agents for the treatment of the diseases/conditions described herein, as described hereinabove and below.

In combination therapy treatment, both the compounds of this invention and the other drug therapies are administered to mammals (e.g., humans, male or female) by conventional methods. The compounds of the present invention may also be administered in combination with naturally occurring compounds that act to lower plasma cholesterol levels. These naturally occurring compounds are commonly called nutraceuticals and include, for example, garlic extract and niacin.

Any cholesterol absorption inhibitor may be used as the second compound in the combination aspect of this invention. The term cholesterol absorption inhibition refers to the ability of a compound to prevent cholesterol contained within the lumen of the intestine from entering into the intestinal cells and/or passing from within the intestinal cells into the blood stream. Such cholesterol absorption inhibition activity is readily determined by those skilled in the art according to standard assays (e.g., J. Lipid Res. (1993) 34: 377–395). Cholesterol absorption inhibitors are known to those skilled in the art and are described, for example, in PCT WO 94/00480.

Any HMG-CoA reductase inhibitor may be used as the second compound in the combination aspect of this invention. The term HMG-CoA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol. 1981; 71:455–509 and references cited therein). A variety of these compounds are described and referenced below, however other HMG-CoA reductase inhibitors will be known to those skilled in the art. U.S. Pat. No. 4,231,938 discloses certain compounds isolated after cultivation of a microorganism belonging to the genus Aspergillus, such as lovastatin. Also, U.S. Pat. No. 4,444,784 discloses synthetic derivatives of the aforementioned compounds, such as simvastatin. Also, U.S. Pat. No. 4,739,073 discloses certain substituted indoles, such as fluvastatin. Also, U.S. Pat. No. 4,346,227 discloses ML-236B derivatives, such as pravastatin. Also, EP-491226A discloses certain pyridyidihydroxyheptenoic acids, such as rivastatin. In addition, U.S. Pat. No. 5,273,995 discloses certain 6-[2-(substituted-pyrrol-1-yl)alkyl]pyran-2-ones such as atorvastatin and the hemicalcium salt thereof (Lipitor®). Additional HMG-CoA reductase inhibitors include rosuvastatin and itavostatin.

Any MTP/Apo B secretion (microsomal triglyceride transfer protein and/or apolipoprotein B secretion) inhibitor may be used as the second compound in the combination aspect of this invention. The term MTP/Apo B secretion inhibitor refers to compounds which inhibit the secretion of triglycerides, cholesteryl ester, and phospholipids. Such inhibition is readily determined by those skilled in the art according to standard assays (e.g., Wetterau, J. R. 1992; Science 258:999). A variety of these compounds are known to those skilled in the art, including those disclosed in WO 96/40640 and WO 98/23593.

Any HMG-CoA synthase inhibitor may be used as the second compound in the combination aspect of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (e.g., Meth Enzymol. 1975; 35:155–160: Meth. Enzymol. 1985; 110:19–26 and references cited therein). A variety of these compounds are described and referenced below, however other HMG-CoA synthase inhibitors will be known to those skilled in the art. U.S. Pat. No. 5,120,729 discloses certain beta-lactam derivatives. U.S. Pat. No. 5,064,856 discloses certain spiro-lactone derivatives prepared by culturing a microorganism (MF5253). U.S. Pat. No. 4,847,271 discloses certain oxetane compounds such as 11-(3-hydroxymethyl-4-oxo-2-oxetayl)-3,5,7-trimethyl-2,4-undeca-dienoic acid derivatives.

Any compound that decreases HMG-CoA reductase gene expression may be used as the second compound in the combination aspect of this invention. These agents may be HMG-CoA reductase transcription inhibitors that block or decrease the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such regulation is readily determined by those skilled in the art according to standard assays (e.g., Meth. Enzymol. 1985; 110:9–19). Inhibitors of HMG-CoA reductase gene expression will be known to those skilled in the art; for example, U.S. Pat. No. 5,041,432 discloses certain 15-substituted lanosterol derivatives. Other oxygenated sterols that suppress synthesis of HMG-CoA reductase are discussed by E. I. Mercer (Prog.Lip. Res. 1993;32:357–416).

Any compound having activity as a CETP inhibitor can serve as the second compound in the combination aspect of the instant invention. The term CETP inhibitor refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). A variety of CETP inhibitors will be known to those skilled in the art, for example, those disclosed in commonly assigned U.S. Pat. No. 6,140,343 and commonly assigned, allowed, U.S. application Ser. No. 09/391,152.

U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.*, 49(8): 815–816 (1996), and *Bioorg. Med. Chem. Lett.*; 6:1951–1954 (1996), respectively.

Any squalene synthetase inhibitor may be used as the second compound of the combination aspect of this invention. The term squalene synthetase inhibitor refers to compounds which inhibit the condensation of 2 molecules of farnesylpyrophosphate to form squalene, catalyzed by the enzyme squalene synthetase. Such inhibition is readily determined by those skilled in the art according to standard assays (e.g., Meth. Enzymol. 1969; 15: 393–454 and Meth. Enzymol. 1985; 110:359–373 and references contained therein). A variety of these compounds are known to those skilled in the art; for example, U.S. Pat. No. 5,026,554 discloses fermentation products of the microorganism MF5465 (ATCC 74011) including zaragozic acid. A summary of other squalene synthetase inhibitors has been compiled (Curr. Op. Ther. Patents (1993) 861–4).

Any squalene epoxidase inhibitor may be used as the second compound in the combination aspect of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (e.g., Biochim. Biophys. Acta 1984; 794:466–471). A variety of these compounds are known to those skilled in the art, for example, U.S. Pat. Nos. 5,011,859 and 5,064,864 disclose certain fluoro analogs of squalene. EP publication 395,768 A discloses certain substituted allylamine derivatives. PCT publication WO 9312069 A discloses certain amino alcohol derivatives. U.S. Pat. No. 5,051,534 discloses certain cyclopropyloxy-squalene derivatives.

Any squalene cyclase inhibitor may be used as the second component in the combination aspect of this invention. The term squalene cyclase inhibitor refers to compounds which inhibit the bioconversion of squalene-2,3-epoxide to lanosterol, catalyzed by the enzyme squalene cyclase. Such inhibition is readily determined by those skilled in the art according to standard assays (e.g., FEBS Lett. 1989;244:347–350). Squalene cyclase inhibitors are known to those skilled in the art. For example, PCT publication WO9410150 and French patent publication 2697250 disclose squalene cyclase inhibitors.

Any combined squalene epoxidase/squalene cyclase inhibitor may be used as the second component in the combination aspect of this invention. The term combined squalene epoxidase/squalene cyclase inhibitor refers to compounds that inhibit the bioconversion of squalene to lanosterol via a squalene-2,3-epoxide intermediate. In some assays it is not possible to distinguish between squalene epoxidase inhibitors and squalene cyclase inhibitors. However, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of squalene epoxidase/squalene cyclase inhibitors are known to those skilled in the art. U.S. Pat. Nos. 5,084, 461 and 5,278,171 disclose certain azadecalin derivatives. EP publication 468,434 discloses certain piperidyl ether and thio-ether derivatives such as 2-(1-piperidyl)pentyl isopentyl sulfoxide and 2-(1-piperidyl)ethyl ethyl sulfide. PCT publication WO 9401404 discloses certain acyl-piperidines such as 1-(1-oxopentyl-5-phenylthio)-4-(2-hydroxy-1-methyl)-ethyl)piperidine. U.S. Pat. No. 5,102,915 discloses certain cyclopropyloxy-squalene derivatives.

Any ACAT inhibitor can serve as the second compound in the combination aspect of this invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research.*, 24:1127 (1983). A variety of these compounds are known to those skilled in the art; for example, U.S. Pat. No. 5,510,379 discloses certain carboxysulfonates, while WO 96/26948 and WO 96/10559 both disclose urea derivatives having ACAT inhibitory activity.

A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays (e.g., Methods Enzymol. 286:190–231).

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions. Such pancreatic lipase inhibition activity is readily determined by those skilled in the art according to standard assays (e.g., Methods Enzymol. 286: 190–231).

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology*, 92, 125 (1987). Such gastric lipase inhibition activity is readily determined by those skilled in the art according to standard assays (e.g., Methods Enzymol. 286:190–231).

A variety of gastric and/or pancreatic lipase inhibitors are known to one of ordinary skill in the art. Preferred lipase inhibitors are those inhibitors that are selected from the group consisting of lipstatin, tetrahydrolipstatin (orlistat), valilactone, esterastin, ebelactone A, and ebelactone B. The compound tetrahydrolipstatin is especially preferred. The lipase inhibitor, N-3-trifluoromethylphenyl-N'-3-chloro4'- trifluoromethylphenylurea, and the various urea derivatives related thereto, are disclosed in U.S. Pat. No. 4,405,644. The lipase inhibitor, esteracin, is disclosed in U.S. Pat. Nos. 4,189,438 and 4,242,453. The lipase inhibitor, cyclo-O,O'-[(1,6-hexanediyl)-bis-(iminocarbonyl)]dioxime, and the various bis(iminocarbonyl)dioximes related thereto may be prepared as described in Petersen et al., Liebig's Annalen, 562, 205–229 (1949).

A variety of pancreatic lipase inhibitors are described herein below. The pancreatic lipase inhibitors lipstatin, (2S, 3S, 5S, 7Z, 10 Z)-5-[(S)-2-formamido-4-methyl-valeryloxy]-2-hexyl-3-hydroxy-7,10-hexadecanoic acid lactone, and tetrahydrolipstatin (orlistat), (2S, 3S, 5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed in U.S. Pat. No. 4,598,089. For example, tetrahydrolipstatin is prepared as described in, e.g., U.S. Pat. Nos. 5,274,143; 5,420,305; 5,540,917; and 5,643,874. The pancreatic lipase inhibitor, FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813. The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151. The pancreatic lipase inhibitor, valilactone, and a process for the preparation thereof by the microbial cultivation of Actinomycetes strain MG147-CF2, are disclosed in Kitahara, et al., J. Antibiotics, 40 (11), 1647–1650 (1987). The pancreatic lipase inhibitors, ebelactone A and ebelactone B, and a process for the preparation thereof by the microbial cultivation of Actinomycetes strain MG7-G1, are disclosed in Umezawa, et al., J. Antibiotics, 33, 1594–1596 (1980). The use of ebelactones A and B in the suppression of monoglyceride formation is disclosed in Japanese Kokai 08-143457, published Jun. 4, 1996.

Other compounds that are marketed for hyperlipidemia, including hypercholesterolemia and which are intended to help prevent or treat atherosclerosis include bile acid sequestrants, such as Welchol®, Colestid®, LoCholest® and Questran®; and fibric acid derivatives, such as Atromid®, Lopid® and Tricor®.

Diabetes can be treated by administering to a patient having diabetes (especially Type II), insulin resistance, impaired glucose tolerance, or the like, or any of the diabetic complications such as neuropathy, nephropathy, retinopathy or cataracts, a therapeutically effective amount of a Formula I compound in combination with other agents (e.g., insulin) that can be used to treat diabetes. This includes the classes of anti-diabetic agents (and specific agents) described above in the Summary of the Invention.

Any glycogen phosphorylase inhibitor may be used as the second agent in combination with a Formula I compound. The term glycogen phosphorylase inhibitor refers to compounds that inhibit the bioconversion of glycogen to glucose-1-phosphate which is catalyzed by the enzyme glycogen phosphorylase. Such glycogen phosphorylase inhibition activity is readily determined by those skilled in the art according to standard assays (e.g., J. Med. Chem. 41 (1998) 2934–2938). A variety of glycogen phosphorylase inhibitors are known to those skilled in the art including those described in WO 96/39384 and WO 96/39385.

Any aldose reductase inhibitor may be used in a combination with a Formula I compound. The term aldose reductase inhibitor refers to compounds that inhibit the bioconversion of glucose to sorbitol, which is catalyzed by the enzyme aldose reductase. Aldose reductase inhibition is readily determined by those skilled in the art according to standard assays (e.g., J. Malone, Diabetes, 29:861–864 (1980). "Red Cell Sorbitol, an Indicator of Diabetic Control"). A variety of aldose reductase inhibitors are known to those skilled in the art.

Any sorbitol dehydrogenase inhibitor may be used in combination with a Formula I compound. The term sorbitol dehydrogenase inhibitor refers to compounds that inhibit the bioconversion of sorbitol to fructose which is catalyzed by the enzyme sorbitol dehydrogenase. Such sorbitol dehydrogenase inhibitor activity is readily determined by those skilled in the art according to standard assays (e.g., Analyt. Biochem (2000) 280: 329–331). A variety of sorbitol dehydrogenase inhibitors are known; for example, U.S. Pat. No. 5,728,704 and 5,866,578 disclose compounds and a method for treating or preventing diabetic complications by inhibiting the enzyme sorbitol dehydrogenase.

Any glucosidase inhibitor may be used in combination with a Formula I compound. A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., Biochemistry (1969) 8: 4214).

A generally preferred glucosidase inhibitor comprises an amylase inhibitor. An amylase inhibitor is a glucosidase inhibitor that inhibits the enzymatic degradation of starch or glycogen into maltose. Such amylase inhibition activity is readily determined by those skilled in the art according to standard assays (e.g., Methods Enzymol. (1955) 1: 149). The inhibition of such enzymatic degradation is beneficial in reducing amounts of bioavailable sugars, including glucose and maltose, and the concomitant deleterious conditions resulting therefrom.

A variety of glucosidase inhibitors are known to one of ordinary skill in the art and examples are provided below. Preferred glucosidase inhibitors are those inhibitors that are selected from the group consisting of acarbose, adiposine, voglibose, miglitol, emiglitate, camiglibose, tendamistate, trestatin, pradimicin-Q and salbostatin. The glucosidase inhibitor, acarbose, and the various amino sugar derivatives related thereto are disclosed in U.S. Pat. Nos. 4,062,950 and 4,174,439 respectively. The glucosidase inhibitor, adiposine, is disclosed in U.S. Pat. No. 4,254,256. The glucosidase inhibitor, voglibose, 3,4-dideoxy-4-[[2-hydroxy-1-

(hydroxymethyl)ethyl]amino]-2-C-(hydroxymethyl)-D-epi-inositol, and the various N-substituted pseudo-aminosugars related thereto, are disclosed in U.S. Pat. No. 4,701,559. The glucosidase inhibitor, miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436. The glucosidase inhibitor, emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772. The glucosidase inhibitor, MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765. The glucosidase inhibitor, camiglibose, methyl 6-deoxy-6-[(2R,3R,4R,5S)-3,4,5-trihydroxy-2-(hydroxymethyl)piperidino]-α-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078. The glycosidase inhibitor, salbostatin and the various pseudosaccharides related thereto, are disclosed in U.S. Pat. No. 5,091,524.

A variety of amylase inhibitors are known to one of ordinary skill in the art. The amylase inhibitor, tendamistat and the various cyclic peptides related thereto, are disclosed in U.S. Pat. No. 4,451,455. The amylase inhibitor AI-3688 and the various cyclic polypeptides related thereto are disclosed in U.S. Pat. No. 4,623,714. The amylase inhibitor, trestatin, consisting of a mixture of trestatin A, trestatin B and trestatin C and the various trehalose-containing amino-sugars related thereto are disclosed in U.S. Pat. No. 4,273,765.

The Formula I compounds can be used in combination with other anti-obesity agents. Any anti-obesity agent may be used as the second agent in such combinations and examples are provided below and in the Summary of the Invention. Such anti-obesity activity is readily determined by those skilled in the art according to standard assays (e.g., as outlined below).

Any thyromimetic may be used as the second agent in combination with a Formula I compound. Such thyromimetic activity is readily determined by those skilled in the art according to standard assays (e.g., Atherosclerosis (1996) 126: 53–63). A variety of thyromimetic agents are known to those skilled in the art, for example those disclosed in U.S. Pat. Nos. 4,766,121; 4,826,876; 4,910,305; 5,061,798; 5,284,971; 5,401,772; 5,654,468; and 5,569,674. Other anti-obesity agents include sibutramine which can be prepared as described in U.S. Pat. No. 4,929,629. and bromocriptine which can be prepared as described in U.S. Pat. Nos. 3,752,814 and 3,752,888.

The Formula I compounds can also be used in combination with other antihypertensive agents. Any antihypertensive agent may be used as the second agent in such combinations and examples are provided in the Summary of the Invention. Such antihypertensive activity is readily determined by those skilled in the art according to standard assays (e.g., blood pressure measurements).

Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendil®; angiotensin converting enzyme (ACE) inhibitors, such as Accupril®, Altace®, Captopril®, Lotensin®, Mavik®, Monopril®, Prinivil®, Univasc®, Vasotec® and Zestril®.

The starting materials and reagents for the above described Formula I compounds and combination agents, are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

Some of the Formula I compounds of this invention or intermediates in their synthesis have asymmetric carbon atoms and therefore are enantiomers or diastereomers. Diastereomeric mixtures can be separated into their individual diastereomers on the basis of their physical chemical differences by methods known per se., for example, by chromatography and/or fractional crystallization. Enantiomers can be separated by, for example, chiral HPLC methods or converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, an enantiomeric mixture of a Formula I compound or an intermediate in its synthesis which contains an acidic or basic moiety may be separated into its corresponding pure enantiomers by forming a diastereomeric salt with an optically pure chiral base or acid (e.g., 1-phenyl-ethyl amine or tartaric acid) and separating the diasteromers by fractional crystallization followed by neutralization to break the salt, thus providing the corresponding pure enantiomers. All such isomers, including diastereomers, enantiomers and mixtures thereof are considered as part of this invention. Also, some of the compounds of this invention are atropisomers (e.g., substituted biaryls) and are considered as part of this invention.

More specifically, the Formula I compounds of this invention may be obtained in enantiomerically enriched form by resolving the racemate of the final compound or an intermediate in its synthesis (preferably the final compound) employing chromatography (preferably high pressure liquid chromatography [HPLC]) on an asymmetric resin (preferably Chiralcel™ AD or OD [obtained from Chiral Technologies, Exton, Pa.]) with a mobile phase consisting of a hydrocarbon (preferably heptane or hexane) containing between 0 and 50% isopropanol (preferably between 2 and 20%) and between 0 and 5% of an alkyl amine (preferably 0.1% of diethylamine). Concentration of the product containing fractions affords the desired materials.

Some of the Formula I compounds of this invention are acidic and they form a salt with a pharmaceutically acceptable cation. Some of the Formula I compounds of this invention are basic and they form a salt with a pharmaceutically acceptable anion. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds can be obtained in crystalline form by dissolution in an appropriate solvent(s) such as ethanol, hexanes or water/ethanol mixtures.

Those skilled in the art will recognize that some of the compounds herein can exist in several tautomeric forms. All such tautomeric forms are considered as part of this invention. For example all enol-keto forms of the compounds of Formula I are included in this invention.

In addition, when the Formula I compounds of this invention form hydrates or solvates they are also within the scope of the invention.

The Formula I compounds of this invention, their prodrugs and the salts of such compounds and prodrugs are all adapted to therapeutic use as agents that activate peroxisome proliferator activator receptor (PPAR) activity in mammals, particularly humans. Thus, it is believed the compounds of this invention, by activating the PPAR receptor, stimulate transcription of key genes involved in fatty acid oxidation and also those involved in high density lioprotein (HDL) assembly (for example apolipoprotein $A_1$ gene transcription), accordingly reducing whole body fat and increasing HDL cholesterol. By virtue of their activity, these agents also reduce plasma levels of triglycerides, VLDL cholesterol, LDL cholesterol and their associated components in mammals, particularly humans, as well as increasing HDL cholesterol and apolipoprotein AI. Hence, these compounds are useful for the treatment and correction of the various dyslipidemias observed to be associated with the development and incidence of atherosclerosis and cardiovascular disease, including hypoalphalipoproteinemia and hypertriglyceridemia.

Given the positive correlation between triglycerides, LDL cholesterol, and their associated apolipoproteins in blood with the development of cardiovascular, cerebral vascular and peripheral vascular diseases, the Formula I compounds of this invention, their prodrugs and the salts of such compounds and prodrugs, by virtue of their pharmacologic action, are useful for the prevention, arrestment and/or regression of atherosclerosis and its associated disease states. These include cardiovascular disorders (e.g., angina, cardiac ischemia and myocardial infarction) and complications due to cardiovascular disease.

Thus, given the ability of the Formula I compounds of this invention, their prodrugs and the salts of such compounds and prodrugs to reduce plasma triglycerides and total plasma cholesterol, and increase plasma HDL cholesterol, they are of use in the treatment of diabetes. The described agents are useful in the treatment of obesity given the ability of the Formula I compounds of this invention, their prodrugs and the salts of such compounds and prodrugs to increase hepatic fatty acid oxidation.

The utility of the Formula I compounds of the invention, their prodrugs and the salts of such compounds and prodrugs as medical agents in the treatment of the above described disease/conditions in mammals (e.g., humans) is demonstrated by the activity of the compounds of this invention in conventional assays and the in vivo assays described below. The in vivo assays (with appropriate modifications within the skill in the art) may be used to determine the activity of other lipid or triglyceride controlling agents as well as the compounds of this invention. The combination protocol described below is useful for demonstrating the utility of the combinations of the agents (i.e., the compounds of this invention) described herein. Such assays also provide a means whereby the activities of the Formula I compounds of this invention, their prodrugs and the salts of such compounds and prodrugs (or the other agents described herein) can be compared to each other and with the activities of other known compounds. The results of these comparisons are useful for determining dosage levels in mammals, including humans, for the treatment of such diseases.

The following protocols can of course be varied by those skilled in the art.

PPAR FRET Assay

Measurement of coactivator recruitment by a nuclear receptor after receptor-ligand association is a method for evaluating the ability of a ligand to produce a functional response through anuclear receptor. The PPAR FRET (Fluorescence Resonance Energy Transfer) assay measures the ligand-dependent interaction between nuclear receptor and coactivator. GST/PPAR ($\alpha$, $\beta$, and $\gamma$) ligand binding domain (LBD) is labeled with a europium-tagged anti-GST antibody, while an SRC-1 (Sterol Receptor Coactivator-1) synthetic peptide containing an amino terminus long chain biotin molecule is labeled with streptavidin-linked allophycocyanin (APC). Binding of ligand to the PPAR LBD causes a conformational change that allows SRC-1 to bind. Upon SRC-binding, the donor FRET molecule (europium) comes in close proximity to the acceptor molecule (APC), resulting in fluorescence energy transfer between donor (337 nm excitation and 620 nm emission) and acceptor (620 nm excitation and 665 nm emission). Increases in the ratio of 665nm emission to 620 nm emission is a measure of the ability of the ligand-PPAR LBD to recruit SRC-1 synthetic peptide and therefore a measure of the ability of a ligand to produce a functional response through the PPAR receptor.

[1] GST/PPAR LBD Expression. The human PPARα LBD (amino acids 235–507) is fused to the carboxy terminus of glutathione S-transferase (GST) in pGEX-6P-1 (Pharmacia, Piscataway, N.J.). The GST/PPARα LBD fusion protein is expressed in BL21[DE3]pLysS cells using a 50 uM IPTG induction at room temperature for 16 hr (cells induced at an $A_{600}$ of ~0.6). Fusion protein is purified on glutathione sepharose 4B beads, eluted in 10 mM reduced glutathione, and dialyzed against 1× PBS at 4° C. Fusion protein is quantitated by Bradford assay (M. M. Bradford, Analst. Biochem. 72:248–254; 1976), and stored at −20° C. in 1× PBS containing 40% glycerol and 5 mM DTT.

[2] FRET Assay. The FRET assay reaction mix consists of 1× FRET buffer (50 mM Tris-Cl pH 8.0, 50 mM KCl, 0.1 mg/ml BSA, 1 mM EDTA, and 2 mM DTT) containing 20 nM GST/PPARα LBD, 40 nM of SRC-1 peptide (amino acids 676–700, 5'-long chain biotin-CPSSHSSLTERHKILHRLLQEGSPS—$NH_2$, purchased from American Peptide Co., Sunnyvale, Calif.), 2 nM of europium-conjugated anti-GST antibody (Wallac, Gaithersburg, Md.), 40 nM of streptavidin-conjugated APC (Wallac), and control and test compounds. The final volume is brought to 100 $\mu$l with water and transferred to a black 96-well plate (Microfuor B, Dynex (Chantilly, Va.)). The reaction mixes are incubated for 1 hr at 4° C. and fluorescence is read in Victor 2 plate reader (Wallac). Data is presented as a ratio of the emission at 665 nm to the emission at 615 nm.

Assessment of Lipid-modulating Activity in Mice

[1] Triglyceride Lowering. The hypolipidemic treating activity of the compounds of this invention may be demonstrated by methods based on standard procedures. For example, the in vivo activity of these compounds in decreasing plasma triglyceride levels may be determined in transgenic mice expressing human apolipoprotein AI (ApoAI), apolipoprotein CIII (apoCIII) and cholesterol ester transport protein (CETP) transgenes (HuAICIIICETPTg mice). The transgenic mice for use in this study are described in Walsh et al., J. Lipid Res. 1993, 34: 617–623, Agellon et al., J. Biol. Chem. 1991, 266: 10796–10801. Mice expressing the human apoA-I, apoCIII and CETP transgenes are obtained by mating transgenic mice expressing the human apoAI and apoCIII transgenes (HuAICIIITg) with mice carrying the human CETP transgene (HuCETPTg).

Male HuAICIIICETPTg mice (8–11 weeks old) are housed 4–5/cage and maintained in a 12 hr light/12 hr dark cycle. Animals have ad lib. access to Purina rodent chow and water. The animals are dosed daily (9 AM) by oral gavage with vehicle (water or 5% sodium bicarbonate) or with vehicle containing test compound at the desired concentration. Plasma triglycerides levels are determined initially (day 0) and 24 hours after the administration of the last dose (day 3) from blood collected retro-orbitally with heparinized hematocrit tubes. Triglyceride determinations are performed using a commercially available Triglyceride E kit from Wako (Osaka, Japan).

[2] HDL Cholesterol Elevation. The activity of the compounds of this invention for raising the plasma level of high density lipoprotein (HDL) in a mammal can be demonstrated in transgenic mice expressing the human apoAI and CETP transgenes (HuAICETPTg). The transgenic mice for use in this study are described previously in Walsh et al., J. Lipid Res. 1993, 34: 617–623, Agellon et al., J. Biol. Chem. 1991, 266: 10796–10801. Mice expressing the human apoAI and CETP transgenes are obtained by mating transgenic mice expressing the human apoAI transgene (HuAITg) with CETP mice (HuCETPTg).

Male HuAICETPTg mice (8–11 weeks old) are grouped according to their human apo AI levels and have free access to Purina rodent chow and water. Animals are dosed daily by oral gavage with vehicle (water or 5% sodium bicarbonate) or with vehicle containing test compound at the desired dose for 5 days. HDL-cholesterol, murine apoAI and human apoAI are determined initially (day 0) and 90 minutes post dose (day 5) using methods based on standard procedures. Mouse HDL is separated from apoB-containing lipoproteins by dextran sulfate precipitation as described elsewhere (Francone et al., 1997, 38:813–822). Cholesterol is measured enzymatically using a commercially available cholesterol/HP Reagent kit (Boehringer MannHeim, Indianapolis, Ind.) and spectrophotometrically quantitated on a microplate reader. Murine and human apoAI are measured by a sandwich enzyme-linked immunosorbent assay as previously described (Francone et al., 1997, 38:813–822, Atger et al., J. Clin. Invest. 1995, 96:2613–2622).

Measurement of Glucose Lowering in the ob/ob Mouse

The hypoglycemic activity of the compounds of this invention can be determined by the amount of test compound that reduces glucose levels relative to a vehicle without test compound in male ob/ob mice. The test also allows the determination of an approximate minimal effective dose (MED) value for the in vivo reduction of plasma glucose concentration in such mice for such test compounds.

Five to eight week old male C57BL/6J-ob/ob mice (obtained from Jackson Laboratory, Bar Harbor, Me.) are housed five per cage under standard animal care practices. After a one week acclimation period, the animals are weighed and 25 microliters of blood are collected from the retro-orbital sinus prior to any treatment. The blood sample is immediately diluted 1:5 with saline containing 0.025% sodium heparin, and held on ice for metabolite analysis. Animals are assigned to treatment groups so that each group has a similar mean for plasma glucose concentration. After group assignment, animals are dosed orally each day for four days with the vehicle consisting of either: (1) 0.25% w/v methyl cellulose in water without pH adjustment; or (2) 0.1% Pluronic® P105 Block Copolymer Surfactant (BASF Corporation, Parsippany, N.J.) in 0.1% saline without pH adjustment. On day 5, the animals are weighed again and then dosed orally with a test compound or the vehicle alone. All compounds are administered in vehicle consisting of either: (1) 0.25% w/v methyl cellulose in water; (2) 10% DMSO/0.1% Pluronic® in 0.1% saline without pH adjustment; or 3) neat PEG 400 without pH adjustment. The animals are then bled from the retro-orbital sinus three hours later for determination of blood metabolite levels. The freshly collected samples are centrifuged for two minutes at 10,000× g at room temperature. The supernatant is analyzed for glucose, for example, by the Abbott VP™ (Abbott Laboratories, Diagnostics Division, Irving, Tex.) and VP Super System® Autoanalyzer (Abbott Laboratories, Irving, Tex.), or by the Abbott Spectrum CCX™ (Abbott Laboratories, Irving, Tex.) using the A-Gent™ Glucose-UV Test reagent system (Abbott Laboratories, Irving, Tex.) (a modification of the method of Richterich and Dauwalder, *Schweizerische Medizinische Wochenschrift*, 101: 860 (1971)) (hexokinase method) using a 100 mg/dl standard. Plasma glucose is then calculated by the equation: plasma glucose (mg/dl)=sample value×8.14 where 8.14 is the dilution factor, adjusted for plasma hematocrit (assuming the hematocrit is 44%).

The animals dosed with vehicle maintain substantially unchanged hyperglycemic glucose levels (e.g., greater than or equal to 250 mg/dl), animals treated with compounds having hypoglycemic activity at suitable doses have significantly depressed glucose levels. Hypoglycemic activity of the test compounds is determined by statistical analysis (unpaired t-test) of the mean plasma glucose concentration between the test compound group and vehicle-treated group on day 5. The above assay carried out with a range of doses of a test compound allows the determination of an approximate minimal effective dose (MED) value for the in vivo reduction of plasma glucose concentration.

Measurement of Insulin, Triglyceride, and Cholesterol Levels in the ob/ob Mouse

The compounds of the present invention are readily adapted to clinical use as hyperinsulinemia reversing agents, triglyceride lowering agents and hypocholesterolemic agents. Such activity can be determined by the amount of test compound that reduces insulin, triglycerides or cholesterol levels relative to a control vehicle without test compound in male ob/ob mice.

Since the concentration of cholesterol in blood is closely related to the development of cardiovascular, cerebral vascular or peripheral vascular disorders, the compounds of this invention, by virtue of their hypocholesterolemic action, prevent, arrest and/or regress atherosclerosis.

Since the concentration of insulin in blood is related to the promotion of vascular cell growth and increased renal sodium retention, (in addition to the other actions, e.g., promotion of glucose utilization) and these functions are known causes of hypertension, the compounds of this invention, by virtue of their hypoinsulinemic action, prevent, arrest and/or regress hypertension.

Since the concentration of triglycerides in blood contributes to the overall levels of blood lipids, the compounds of this invention, by virtue of their triglyceride lowering and/or free fatty acid lowering activity prevent, arrest and/or regress hyperlipidemia.

Free fatty acids contribute to the overall level of blood lipids and independently have been negatively correlated with insulin sensitivity in a variety of physiologic and pathologic states.

Five to eight week old male C57BL/6J-ob/ob mice (obtained from Jackson Laboratory, Bar Harbor, Me.) are housed five per cage under standard animal care practices and fed standard rodent diet ad libitum. After a one week acclimation period, the animals are weighed and 25 microliters of blood are collected from the retro-orbital sinus prior to any treatment. The blood sample is immediately diluted 1:5 with saline containing 0.025% sodium heparin, and held on ice for plasma glucose analysis. Animals are assigned to treatment groups so that each group has a similar mean for plasma glucose concentration. The compound to be tested is administered by oral gavage as an about 0.02% to 2.0% solution (weigh/volume (w/v)) in either (1) 10% DMSO/ 0.1% Pluronic® P105 Block Copolymer Surfactant (BASF Corporation, Parsippany, N.J.) in 0.1% saline without pH adjustment or (2) 0.25% w/v methylcellulose in water without pH adjustment. Alternatively, the compound to be tested can be administered by oral gavage dissolved in or in suspension in neat PEG 400. Single daily dosing (s.i.d.) or twice daily dosing (b.i.d.) is maintained for 1 to, for example, 15 days. Control mice receive the 10% DMSO/ 0.1% Pluronic® P105 in 0.1% saline without pH adjustment or the 0.25% w/v methylcellulose in water without pH adjustment, or the neat PEG 400 without pH adjustment.

Three hours after the last dose is administered, the animals are sacrificed by decapitation and trunk blood is collected into 0.5 ml serum separator tubes containing 3.6 mg of a 1:1 weight/weight sodium fluoride: potassium oxalate mixture. The freshly collected samples are centrifuged for two minutes at 10,000× g at room temperature, and the serum supernatant is transferred and diluted 1:1 volume/ volume with a 1TIU/ml aprotinin solution in 0.1% saline without pH adjustment.

The diluted serum samples are then stored at −80° C. until analysis. The thawed, diluted serum samples are analyzed for insulin, triglycerides, free fatty acids and cholesterol levels. Serum insulin concentration is determined using Equate® RIA INSULIN kits (double antibody method; as specified by the manufacturer) available from Binax, South Portland, Me. The inter assay coefficient of variation is ≦10%. Serum triglycerides are determined using the Abbott VP™ and VP Super System® Autoanalyzer (Abbott Laboratories, Irving, Tex.), or the Abbott Spectrum CCX™ (Abbott Laboratories, Irving, Tex.) using the A-Gen™ Triglycerides Test reagent system (Abbott Laboratories, Diagnostics Division,Irving, Tex.) (lipase-coupled enzyme method; a modification of the method of Sampson, et al., *Clinical Chemistry* 21: 1983 (1975)). Serum total cholesterol levels are determined using the Abbott VP™ and VP Super System® Autoanalyzer (Abbott Laboratories, Irving, Tex.), and A-Gent™ Cholesterol Test reagent system (cholesterol esterase-coupled enzyme method; a modification of the method of Allain, et al. *Clinical Chemistry* 20: 470 (1974)) using 100 and 300 mg/dl standards. Serum free fatty acid concentration is determined utilizing a kit from WAKO (Osaka, Japan), as adapted for use with the Abbott VP™ and VP Super System® Autoanalyzer (Abbott Laboratories, Irving, Tex.), or the Abbott Spectrum CCX™ (Abbott Laboratories, Irving, Tex.). Serum insulin, triglycerides, free fatty acids and total cholesterol levels are then calculated by the equations: serum insulin ($\mu$U/ml)= sample value×2; serum triglycerides (mg/dl)=sample value× 2; serum total cholesterol (mg/dl)=sample value×2; serum free fatty acid ($\mu$Eq/l)=sample value×2; where 2 is the dilution factor.

The animals dosed with vehicle maintain substantially unchanged, elevated serum insulin (e.g., 275 $\mu$U/ml), serum triglycerides (e.g., 235 mg/dl), serum free fatty acid (1500 mEq/ml) and serum total cholesterol (e.g., 190 mg/dl) levels. The serum insulin, triglycerides, free fatty acid and total cholesterol lowering activity of the test compounds are determined by statistical analysis (unpaired t-test) of the mean serum insulin, triglycerides, and total cholesterol concentration between the test compound group and the vehicle-treated control group.

Measurement of Energy Expenditure in Rats

As would be appreciated by those skilled in the relevant art, during increased energy expenditure, animals generally consume more oxygen. In addition, metabolic fuels such as, for example, glucose and fatty acids, are oxidized to $CO_2$ and $H_2O$ with the concomitant evolution of heat, commonly referred to in the art as thermogenesis. Thus, the measurement of oxygen consumption in animals, including humans and companion animals, is an indirect measure of thermogenesis. Indirect calorimetry is commonly used in animals, e.g., humans, by those skilled in the relevant art to measure such energy expenditures.

Those skilled in the art understand that increased energy expenditure and the concomitant burning of metabolic fuels resulting in the production of heat may be efficacious with respect to the treatment of, e.g., obesity.

The ability of the Formula I compounds to generate a thermogenic response may be demonstrated according to the following protocol: This in vivo screen is designed to evaluate the efficacy of compounds that are PPAR agonists, using as an efficacy endpoint measurement of whole body oxygen consumption. The protocol involves: (a) dosing fatty Zucker rats for about 6 days, and (b) measuring oxygen consumption. Male fatty Zucker rats having a body weight range of from about 400 g to about 500 g are housed for from about 3 to about 7 days in individual cages under standard laboratory conditions prior to the initiation of the study. A compound of this invention and a vehicle is administered by oral gavage as a single daily dose given between about 3 p.m. to about 6 p.m. for about 6 days. A compound of this invention is dissolved in vehicle containing about 0.25% of methyl cellulose. The dosing volume is about 1 ml.

About 1 day after the last dose of the compound is administered, oxygen consumption is measured using an open circuit, indirect calorimeter (Oxymax, Columbus Instruments, Columbus, Ohio 43204). The Oxymax gas sensors are calibrated with $N_2$ gas and a gas mixture (about 0.5% of $CO_2$, about 20.5% of $O_2$, about 79% of $N_2$) before each experiment. The subject rats are removed from their home cages and their body weights recorded. The rats are placed into the sealed chambers (43×43×10 cm) of the Oxymax, the chambers are placed in the activity monitors, and the air flow rate through the chambers is then set at from about 1.6 L/min to about 1.7 L/min. The Oxymax software then calculates the oxygen consumption (mL/kg/h) by the rats based on the flow rate of air through the chambers and the difference in oxygen content at the inlet and output ports. The activity monitors have 15 infrared light beams spaced about one inch apart on each axis, and ambulatory activity is recorded when two consecutive beams are broken, and the results are recorded as counts.

Oxygen consumption and ambulatory activity are measured about every 10 min for from about 5 h to about 6.5 h. Resting oxygen consumption is calculated on individual rats by averaging the values excluding the first 5 values and the values obtained during time periods where ambulatory activity exceeds about 100 counts.

In Vivo Atherosclerosis Assay

Anti-atherosclerotic effects of the compounds can be determined by the amount of compound required to reduce the lipid deposition in rabbit aorta. Male New Zealand White rabbits are fed a diet containing 0.2% cholesterol and 10% coconut oil for 4 days (meal-fed once per day). Rabbits are bled from the marginal ear vein and total plasma cholesterol values are determined from these samples. The rabbits are then assigned to treatment groups so that each group has a similar mean ±SD for total plasma cholesterol concentration, HDL cholesterol concentration and triglyceride concentration. After group assignment, rabbits are dosed daily with compound given as a dietary admix or on a small piece of gelatin based confection. Control rabbits receive only the dosing vehicle, be it the food or the gelatin confection. The cholesterol/coconut oil diet is continued along with the compound administration throughout the study. Plasma cholesterol, HDL-cholesterol, LDL cholesterol and triglyceride values can be determined at any point during the study by obtaining blood from the marginal ear vein. After 3–5 months, the rabbits are sacrificed and the aortae are removed from the thoracic arch to the branch of the iliac arteries. The aortae are cleaned of adventitia, opened longitudinally and then stained with Sudan IV as described by Holman et. al. (Lab. Invest. 1958, 7, 42–47). The percent of the surface area stained is quantitated by densitometry using an Optimas Image Analyzing System (Image Processing Solutions; North Reading, Mass.). Reduced lipid deposition is indicated by a reduction in the percent surface area stained in the compound-receiving group in comparison with the control rabbits.

Administration of the compounds of this invention can be via any method which delivers a compound of this invention systemically and/or locally. These methods include oral routes, parenteral, intraduodenal routes, etc. Generally, the compounds of this invention are administered orally, but parenteral administration (e.g., intravenous, intramuscular, subcutaneous or intramedullary) may be utilized, for example, where oral administration is inappropriate or where the patient is unable to ingest the drug.

In general an amount of a compound of this invention is used that is sufficient to achieve the therapeutic effect desired (e.g., lipid lowering).

In general an effective dosage for the Formula I compounds of this invention, their prodrugs and the salts of such compounds and prodrugs is in the range of about 0.001 to about 100 mg/kg/day, preferably about 0.01 to about 10 mg/kg/day.

A dosage of the combination pharmaceutical agents to be used in conduction with the PPAR agonists is used that is effective for the indication being treated. Such dosages can be determined by standard assays such as those referenced above and provided herein. The combination agents may be administered simultaneously or sequentially in any order.

For example, typically an effective dosage for HMG-CoA reductase inhibitors is in the range of about 0.01 to about 100 mg/kg/day.

The compounds of the present invention are generally administered in the form of a pharmaceutical composition comprising at least one of the compounds of this invention together with a pharmaceutically acceptable vehicle, diluent or carrier. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. A preferred formulation is a solution or suspension in an oil, for example olive oil, Miglyol™ or Capmul™, in a soft gelatin capsule. Antioxidants may be added to prevent long term degradation as appropriate. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 19th Edition (1995).

Pharmaceutical compositions according to this invention may contain 0.1%–95% of the compound(s) of this invention, preferably 1%–70%. In any event, the composition or formulation to be administered will contain a quantity of a compound(s) according to this invention in an amount effective to treat the disease/condition of the subject being treated, e.g., atherosclerosis.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I, a prodrug thereof or a salt of such compound or prodrugs and a second compound as described above. The kit comprises means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of this invention can consist of one tablet or capsule while a daily dose of the second compound can consist of several tablets or capsules or vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of this invention either alone or in combination with each other or other compounds generally will be administered in a convenient formulation. The following formulation examples only are illustrative and are not intended to limit the scope of the present invention.

In the formulations which follow, "active ingredient" means a compound of this invention.

Formulation 1: Gelatin Capsules
Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
| --- | --- |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
|---|---|
| Active ingredient dissolved in ethanol 1% | 20 mg |
| Intralipid ™ emulsion | 1,000 mL |

The solution of the above ingredients is intravenously administered to a patient at a rate of about 1 mL per minute.

Soft gelatin capsules are prepared using the following:

Formulation 8: Soft Gelatin Capsule with Oil Formulation

| Ingredient | Quantity (mg/capsule) |
|---|---|
| Active ingredient | 10–500 |
| Olive Oil or Miglyol ™ Oil | 500–1000 |

The active ingredient above may also be a combination of agents.

GENERAL EXPERIMENTAL PROCEDURES

NMR spectra were recorded on a Varian XL-300 (Varian Co., Palo Alto, Calif.), a Bruker AM-300 spectrometer (Bruker Co., Billerica, Mass.) or a Varian Unity 400 at ambient temperature. Chemical shifts are expressed in parts per million ($\delta$) relative to residual solvent as an internal reference. The peak shapes are denoted as follows: s, singlet; d, doublet; t, triplet; q, quartet; m, multiplet; brs=broad singlet; 2s, two singlets. Atmospheric pressure chemical ionization (APCI) mass spectra in alternating positive and negative ion mode were obtained on a Fisons Platform II Spectrometer, Fisons Instruments Manchester U.K.). Chemical ionization mass spectra were obtained on a Hewlett-Packard 5989 instrument (Hewlett-Packard Co., Palo Alto, Calif.) (ammonia ionization, PBMS). Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. Optical rotations were determined on a Perkin-Elmer 241 polarimeter (Perkin-Elmer Instruments, Norwalk, Conn.) using the sodium D line ($\lambda$=589 nm) at the indicated temperature and are reported as follows $[\alpha]_D^{temp}$, concentration (c=g/100 mL), and solvent.

Column chromatography was performed with either Baker Silica Gel (40 $\mu$m) (J. T. Baker, Phillipsburg, N.J.) or Silica Gel 50 (EM Sciences, Gibbstown, N.J.) in glass columns or in Flash 40 (Biotage, Dyar Corp. Charlottesville, Va.) columns under low nitrogen pressure. Radial Chromatography was performed using a Chromatron (model 7924T, Harrison Research, Palo Alto, Calif.). Unless otherwise specified, reagents were used as obtained from commercial sources. Dimethylformamide, 2-propanol, tetrahydrofuran, toluene and dichloromethane used as reaction solvents were the anhydrous grade supplied by Aldrich Chemical Company (Milwaukee, Wis.). Microanalyses were performed by Schwarzkopf Microanalytical Laboratory, Woodside, N.Y. The terms "concentrated" and "evaporated" refer to removal of solvent at 5–200 mm of mercury pressure on a rotary evaporator with a bath temperature of less than 45° C. Reactions conducted at "0–20° C." or "0–25° C." were conducted with initial cooling of the vessel in an insulated ice bath which was then allowed to warm to room temperature. The abbreviation "min" and "h" stand for "minutes" and "hours" respectively.

EXAMPLE 1

(4-Bromomethyl-phenyl)-acetic acid:

To a stirred solution of p-methylphenylacetic acid (0.175 mol, 27.8 g) in tetrachloromethane (250 mL) under a nitrogen atmosphere in a round bottom flask equipped with a reflux condenser and provision for trapping the released HBr was added bromine (0.175 mol, 27.8 g) dissolved in tetrachloromethane. The red/brown mixture was irradiated and brought to reflux with a 250 watt incandescent light source. Over the course of ten minutes, the color was discharged and a crystalline precipitate was formed. The mixture was allowed to cool to room temperature, and the solid was collected by vacuum filtration, and dried in a stream of nitrogen to give (4-bromomethyl-phenyl)-acetic acid as a white solid containing 6.3% by weight p-methylphenylacetic acid as an impurity. (25.1 g, 63%).

$^1$H NMR $\delta$(CDCl$_3$): 12.34 (br.s., 1H); 7.85 (d, J=8.10 Hz, 2H); 7.21 (d, J=8.30 Hz, 2H); 4.66 (s, 2H); 3.64 (s, 2H)

EXAMPLE 2

N-Heptyl-2-(4-hydroxymethyl-phenyl)-acetamide:

A stirred solution of (4-bromomethyl-phenyl)acetic acid (80.0 mmol, 12.0 g) and thionyl chloride (240 mmol, 17.5 mL) in chloroform (200 mL) under a nitrogen atmosphere was heated under reflux for 16 hours. The solution was cooled to room temperature and concentrated under reduced pressure to a white solid. The solid was dissolved in dichloromethane and added dropwise to a solution of 1-heptylamine (95.9 mmol, 14.2 mL) and N,N-diisopropylethylamine (95.9 mmol, 16.7 mL) in dichloromethane (100 mL) cooled to 0° C. The resulting solution was stirred at room temperature for 25 minutes. The mixture was poured over 1N HCl, and the aqueous layer was extracted with dichloromethane (2x). The organic layers were combined, washed with 2N HCl (2x), brine (1x), dried over anhydrous sodium sulfate and concentrated to give a white solid. A stirred solution of this solid (~24.7 mmol, 7.5 g) and CaCO$_3$(120 mmol, 12.0 g) in a 1:1 H$_2$O/dioxane mixture (150 mL) was brought to reflux for 3 hours. The solution was cooled to room temperature and concentrated to a white residue. Water and dichloromethane were added and the remaining solid was dissolved by the addition of 6N HCl. The aqueous layer was isolated and extracted with dichloromethane (2x). The organic layers were combined, washed with brine (1x), dried over anhydrous sodium sulfate, and concentrated to give a yellow oil. The oil was purified by chromatography on silica gel (Merck silica gel 60, art#9385-3) eluting with 10% CH$_3$OH in dichloromethane to give N-heptyl-2-(4-hydroxymethyl-phenyl)-acetamide as a white solid (1.5 g, 24%).

$^1$H NMR δ(CDCl$_3$): 7.83 (d, J=8.10 Hz, 2H); 7.21 (d, J=8.10 Hz, 2H); 5.46 (br.s, 1H); 4.68 (s, 2H); 3.52 (s, 2H); 3.15 (dt, J=7.17, 6.02 Hz, 2H); 1.38 (quint, J=7.17 Hz, 2H); 1.28–1.13 (m, 8H); 0.83 (t, J=6.96 Hz, 3H)

MS: m/z 264.0 (M+1).

EXAMPLE 3

[4-(2-Heptylamino-ethyl)-phenyl]-methanol:

To a stirred solution of N-heptyl-2-(4-hydroxymethyl-phenyl)-acetamide (5.6 mmol, 1.48 g) dissolved in tetrahydrofuran (15 mL) under a nitrogen atmosphere at 0° C. was added sodium borohydride (16.9 mmol, 639 mg) followed by the dropwise addition of boron trifluoride diethyletherate (22.5 mmol, 2.85 mL). The mixture was allowed to stir at room temperature for 11 hours. The reaction was quenched by the cautious addition of 2N HCl until gas evolution had ceased. The resulting mixture was refluxed for 45 minutes, cooled to room temperature and concentrated to a white solid. The solid was dissolved in water, then brought to pH 14 with 2N NaOH. The aqueous solution was extracted with diethyl ether (3x). The organic layers were combined, washed with brine (1x), dried over anhydrous sodium sulfate and concentrated to give [4-(2-heptylamino-ethyl)-phenyl]-methanol as a clear oil (1.37 g, 98%).

$^1$H NMR δ(CDCl$_3$): 7.27 (d, J=8.09 Hz, 2H); 7.16 (d, J=7.88 Hz, 2H); 4.63 (s, 2H); 2.87–2.72 (m, 4H); 2.56 (t, J=7.37 Hz, 2H); 1.85 (br.s, 2H); 1.42 (quint, J=7.26 Hz, 2H); 1.31–1.15 (m, 8H); 0.85 (t, J=6.95 Hz, 3H)

MS: m/z 250.5 (m+1).

EXAMPLE 4

Heptyl-[2-(4-hydroxymethyl-phenyl)-ethyl]-carbamic acid tert-butyl ester:

To a beaker containing saturated NaHCO$_3$ (20 mL) and [4-(2-heptylamino-ethyl)-phenyl]-methanol (5.5 mmol, 1.2 g) dissolved in tetrahydrofuran (8 mL) was added di-tert-butyl dicarbonate (5.5 mmol, 1.2 g). To the solution was added 2M NaOH to maintain the pH of the solution between 8 and 9. After the pH of the solution became stable, the mixture was extracted with diethyl ether (3x). The organic layers were combined, dried over anhydrous sodium sulfate, and concentrated to a clear oil. The crude product was purified by flash chromatography (Merck silica gel 60, art#9385-3) eluting with 10% methanol/methylene chloride to give the heptyl-[2-(4-hydroxymethyl-phenyl)-ethyl]-carbamic acid tert-butyl ester as a colorless oil (1.70 g, 89%).

$^1$H NMR δ(CDCl$_3$): 7.28 (d, J=7.89 Hz, 2H); 7.17 (br.s, 2H); 4.64 (d, J=5.81 Hz, 2H); 3.33 (br.s, 2H); 3.20–3.00 (m, 2H); 2.87–2.73 (br.s, 2H); 1.68 (t, J=5.92 Hz, 1H); 1.49–1.40 (m, 11H); 1.34–1.15 (m, 8H); 0.86 (t, J=6.76 Hz, 3H)

MS: m/z 250.0 (M–100+1).

EXAMPLE 5

[2-(4-Formyl-phenyl)-ethyl-heptyl-carbamic acid tert-butyl ester:

To a stirred solution of heptyl-[2-(4-hydroxymethyl-phenyl)-ethyl]-carbamic acid tert-butyl ester (4.9 mmol, 1.7 g) in anhydrous ether (50 mL) was added activated manganese dioxide (Aldrich, 5 g). The resulting suspension was stirred at room temperature adding further 2 g portions of manganese dioxide every 2 hours until the starting material had been consumed as determined by TLC. The mixture was filtered through a Celite® plug and washed through exhaustively with dichloromethane. The yellow filtrate was concentrated to a yellow oil which was chromatographed on silica gel (20% ethyl acetate/hexanes) to give [2-(4-formyl-phenyl)-ethyl]-heptyl-carbamic acid tert-butyl ester as a clear oil (1.30 g, 76%).

$^1$H NMR δ(CDCl$_3$): 9.96 (s, 1H); 7.79 (d, J=7.89 Hz, 2H); 7.41–7.27 (m, 2H); 3.38 (br.s, 2H); 3.20–3.00 (m, 2H); 2.95–2.80 (m, 2H); 1.50–1.35 (m, 11H); 1.32–1.15 (m, 8H); 0.86 (t, J=6.75 Hz, 3H)

MS: m/z 248.1 (M–100+1).

EXAMPLE 6

3-{4-[2-(tert-Butoxycarbonyl-heptyl-amino)-ethyl]-phenyl}-2-ethoxy-acrylic acid ethyl ester:

To a suspension of 60% by weight sodium hydride oil dispersion (6.97 mmol, 277 mg) in anhydrous tetrahydrofuran (20 mL) cooled to 0° C. was added 2-diphenylphosphinoyl-2-ethoxyacetic acid ethyl ester (3.80 mmol, 1.26 g) followed by [2-(4-formyl-phenyl)-ethyl]-heptyl-carbamic acid tert-butyl ester (3.46 mmol, 1.2 g) dissolved in anhydrous tetrahydrofuran (15 mL). The resulting heterogeneous solution was heated to reflux for one hour. The mixture was cooled to room temperature, quenched by the addition of ethanol (2 mL) and diluted with water (20 mL). The aqueous layer was isolated and extracted with diethyl ether (3x). The organic layers were combined, washed with saturated NaHCO$_3$ (2x), brine (1x), dried over anhydrous sodium sulfate, and concentrated to a crude yellow oil. The crude oil was chromatographed on silica gel (20% ethyl acetate/hexanes) to give 3-{4-[2-(tert-butoxycarbonyl-heptyl-amino)-ethyl]-phenyl}-2-ethoxy-acrylic acid ethyl ester as a clear oil (700 mg, 44%).

$^1$H NMR δ(CDCl$_3$): 7.69 (d, J=8.09 Hz, 2H); 7.21–7.10 (m, 2H); 6.95 (s, 1H); 4.28 (q, J=7.12 Hz, 2H); 3.87 (q, J=7.06 Hz, 2H); 3.35 (br.s, 2H); 3.20–2.96 (m, 2H); 2.80 (br.s, 2H); 1.54–1.38 (m, 11H); 1.85 (t, J=7.26 Hz, 6H); 0.86 (t, J=6.85 Hz, 3H)

MS: m/z 362 (M–100+1).

EXAMPLE 7

3-{4-[2-(tert-Butoxycarbonyl-heptyl-amino)-ethyl]-phenyl}-2-ethoxy-propionic acid methyl ester:

To a solution of 3-{4-[2-(tert-butoxycarbonyl-heptyl-amino)-ethyl]-phenyl}-2-ethoxy-acrylic acid ethyl ester (1.11 mmol, 510 mg) dissolved in anhydrous methanol (20 mL) was added dry magnesium turnings (2.77 mmol, 67 mg). The resulting solution was allowed to stir at room temperature, with additional portions of magnesium being added after dissolution of the previous portion until the starting material had been consumed as determined by mass spectrometry. The mixture was poured over 25 mL of ice cooled 2M HCl. The acidic mixture was brought to pH 9 by the addition of concentrated aqueous ammonia, then was extracted with diethyl ether (3x). The organic layers were combined, washed with saturated NaCl (3x), dried over anhydrous sodium sulfate, and concentrated under reduced pressure to give 3-{4-[2-(tert-butoxycarbonyl-heptyl-amino)-ethyl]-phenyl}-2-ethoxy-propionic acid methyl ester as a clear oil (437 mg, 88%).

EXAMPLE 8

2-Ethoxy-3-[4-(2-heptylamino-ethyl)-phenyl]-propionic acid methyl ester:

A solution of 3-{4-[2-(tert-butoxycarbonyl-heptyl-amino)-ethyl]-phenyl}-2-ethoxy-propionic acid methyl ester (0.97 mmol, 437 mg) in ethyl acetate (25 mL) under a nitrogen atmosphere was cooled to −78° C., and saturated with HCl gas. The solution was allowed to warm to room temperature and the solvent was evaporated, leaving a white solid. The white solid was pumped dry to give 2-ethoxy-3-[4-(2-heptylamino-ethyl)-phenyl]-propionic acid methyl ester as the HCl salt (364 mg, 97%).

$^1$H NMR δ(CDCl$_3$): 8.83 (br.s, 2H); 7.14 (s, 4H); 4.08 (dd, J=7.48, 5.82 Hz, 1H); 3.58 (s, 3H); 3.45 (dq, J=9.14, 7.06 Hz, 1H); 3.30 (dq, J=9.14, 7.06 Hz, 1H); 3.12–3.00 (m, 2H); 1.30–1015 (m, 8H); 1.01 (t, J=6.80 Hz, 3H); 0.84 (t, J=8.86 Hz, 3H).

EXAMPLE 9

2-Diphenylphosphinoyl-2-ethoxyacetic acid ethyl ester:

To a stirred solution of ethyl diethoxyacetate (17.23 g, 98 mmol) under a nitrogen atmosphere was added chlorodiphenyl phosphine (16.5 g, 75 mmol) dropwise. The resulting mixture was heated to 150° C. for 3 hours. Excess ethyl diethoxyacetate was removed by bulb to bulb distillation, and the residue was dissolved in toluene and treated with diethyl ether at −78° C., causing a white precipitate to form. The slurry was stored at 0° C. for 16 hours and the solid was collected by vacuum filtration and washed with cold diethyl ether to give 2-diphenylphosphinoyl-2-ethoxyacetic acid ethyl ester as a white solid (14 g, 48%).

$^1$H NMR δ(CDCl$_3$): 7.95–7.81 (m, 4H); 7.56–7.48 (m, 2H); 7.47–7.40 (m, 4H); 4.67 (d, J=14.95 Hz, 1H); 4.10 (dq, J=7.07, 2.28 Hz, 2H); 3.70 (dq, J=9.14 Hz, 7.06 Hz, 1H); 3.33 (dq, J=9.14, 7.06 Hz; 1H); 1.06 (t, J=7.07 Hz, 3H); 1.05 (t, J=7.17 Hz, 3H)

MS: m/z 333.2 (M+1)

EXAMPLE 10

3-(4-{2-[3-(2,4-Dimethoxy-phenyl)-1-heptyl-ureido]-ethyl}-phenyl)-2-ethoxy-propionic acid methyl ester:

To a solution of 2-ethoxy-3-[4-(2-heptylamino-ethyl)-phenyl]-propionic acid methyl ester HCl salt (200 mg, 0.52 mmol), and 2,4-methoxyphenylisocyanate (0.57 mmol, 102 mg) in toluene (5 mL) was added N,N-diisopropylethylamine (1.56 mmol, 0.271 mL). The mixture was allowed to stir at room temperature for 16 hours. Then was poured over 1M HCl (5 mL). The aqueous layer was isolated and extracted with diethyl ether (2x). The organic layers were combined, washed with 2M HCl (2x), brine (2x), dried over anhydrous sodium sulfate, and concentrated to give a clear oil. The crude solid was chromatographed on silica gel 40% ethyl acetate/hexanes to give 3-(4-{2-[3-(2,4-dimethoxy-phenyl)-1-heptyl-ureido]-ethyl}-phenyl)-2-ethoxy-propionic acid methyl ester as a clear oil (255 mg, 93%).

MS: m/z 529.5 (M+1)

EXAMPLE 11

3-(4-{2-[3-(2,4-Difluoro-phenyl)-1-heptyl-ureido]-ethyl}-phenyl)-2-ethoxy-propionic acid methyl ester:

To a solution of 2-ethoxy-3-[3-(2-heptylamino-ethyl)-phenyl]-propionic acid methyl ester HCl salt (41 mg, 0.106 mmol), and 2,4-difluorophenylisocyanate (0.17 mmol, 0.0138 mL) in toluene (4.5 mL) was added N,N-diisopropylethylamine (0.32 mmol, 0.055 mL). The mixture was allowed to stir at room temperature for 18 hours, then was poured over 1M HCl (5 mL). The aqueous layer was isolated and extracted with diethyl ether (2x). The organic layers were combined, washed with 2M HCl (2x), brine (2x), dried over anhydrous sodium sulfate, and concentrated to give a clear oil. The crude solid was chromatographed on silica gel (Merck silica gel 60, art#9385-3) eluting with 20% ethyl acetate/hexanes to give 3-(4-{2-[3-(2,4-difluoro-phenyl)-1-heptyl-ureido]-ethyl}-phenyl)-2-ethoxy-propionic acid methyl ester as a clear oil (44 mg, 82%).

$^1$H NMR δ(CDCl$_3$): 8.04–7.94 (m, 1H); 7.20–7.10 (m, 4H); 6.85–6.75 (m, 2H); 6.29 (d, J=3.32, 1H); 3.90 (dd, J=7.47, 5.60 Hz, 1H); 3.69 (s, 3H); 3.56 (dq, J=9.13, 7.05 Hz, 1H); 3.50 (t, J=7.57 Hz, 2H); 3.30 (dq, J=9.13, 7.05 Hz, 1H); 3.20 (t, J=7.68 Hz, 2H); 3.01–2.90 (m, 2H); 2.87 (t, J=7.57 Hz, 2H); 1.58 (quint, J=6.85 Hz, 2H); 1.34–1.16 (m, 8H); 1.13 (t, J=6.95 Hz, 3H); 0.86 (t, J=6.84 Hz, 3H)

MS: m/z 505.3 (M+1)

EXAMPLE 12

3-[4-(2-{[(2,4-Difluorophenyl)-acetyl]-heptyl-amino}-ethyl)-phenyl]-2-ethoxy-propionic acid methyl ester:

To a solution of 2-ethoxy-3-[3-(2-heptylamino-ethyl)-phenyl]-propionic acid methyl ester HCl salt (43 mg, 0.11 mmol) and N,N-diisopropylethylamine (0.33 mmol, 0.058 mL) in anhydrous methylene chloride (2 mL) was added 2,4-difluorophenylacetyl chloride (0.128 mmol) in anhydrous methylene chloride (2 mL). The mixture was allowed to stir at room temperature for 16 hours. Then was poured over 1 M HCl (5 mL). The aqueous layer was isolated and extracted with methylene chloride (1x). The organic layers were combined, washed with 2 M HCl (1x), brine (1x), dried over anhydrous sodium sulfate, and concentrated to give a clear oil. The crude product was chromatographed on silica gel (Merck silica gel 60, art#9385-3) eluting with 20% ethyl acetate/hexanes to give 3-[4-(2-{[(2,4-difluoro-phenyl)-acetyl]-heptyl-amino}-ethyl)-phenyl]-2-ethoxy-propionic acid methyl ester as a clear oil (36.5 mg, 66%).

$^1$H NMR δ(CDCl$_3$): (1:1 ratio of rotomers) 7.30–7.00 (m, 6H); 6.90–6.70 (m, 2H); 4.03–3.95 (m, 1H); 3.70–3.67 (m, 3H); 3.62 (s, 1H); 3.60–3.52 (m, 1H); 3.52–3.42 (m, 2H); 3.89 (s, 1H); 3.87–3.25 (m, 2H); 3.13 (t, J=7.78 Hz, 2H); 3.02–2.90 (m, 2H); 2.80 (t, J=7.66; 2H); 3.13 (t, J=7.78 Hz, 2H); 3.02–2.90 (m, 2H); 2.80 (t, J=7.66 Hz, 2H); 1.59–1.45 (m, 2H); 1.35–1.15 (m, 8H); 1.13 (t, J=7.05 Hz, 3H); 0.90–0.80 (m, 3H)

MS: m/z 504.1 (M+1).

The title compounds of Examples 13–17 were prepared using a procedure analogous to that used for Example 10.

EXAMPLE 13

2-Ethoxy-3-{4-[2-(1-heptyl-3-p-tolyl-ureido)-ethyl]-phenyl}-propionic acid methyl ester:

$^1$H NMR δ(CDCl$_3$): 7.21–7.12 (m, 4H); 7.10–6.99 (m, 4H); 5.92 (s, 1H); 3.99 (dd, J=7.47, 5.40 Hz, 1H); 3.69 (s, 3H); 3.56 (dq, J=9.14, 7.07 Hz, 1H); 3.50 (t, J=7.27 Hz, 2H); 3.30 (dq, J=9.14, 7.07 Hz, 1H); 3.20 (t, J=7.68 Hz, 2H); 3.03–2.91 (m, 2H); 2.86 (t, J=7.06 Hz, 2H); 2.25 (s, 3H); 1.59 (quint, J=7.28 Hz, 2H); 1.36–1.17 (m, 8H); 1.13 (t, J=7.06 Hz, 3H); 0.87 (t, J=6.85 Hz, 3H)

MS: m/z 483.2 (M+1)

EXAMPLE 14

2-Ethoxy-3-{4-[2-(heptyl-p-tolylacetyl-amino)-ethyl]-phenyl}-propionic acid methyl ester:

¹H NMR δ(CDCl₃): (1:1 ratio of rotomers) 7.20–6.97 (m, 8H), 4.02–3.95 (m, 1H); 3.71–3.67 (m, 3H); 3.63 (s, 1H); 3.62–3.53 (m, 1H); 3.52–3.45 (m, 2H); 3.44–3.25 (m, 4H); 3.07 (t, J=7.90, 1H); 3.00–2.90 (m, 2H); 2.80 (t, J=7.69 Hz, 1H); 2.70 (t, J=7.47, 1H); 2.35–2.27 (m, 3H); 1.53 (quint, J=7.28 Hz, 1H); 1.41 (quint, 7.28, 1H); 1.35–1.16 (m, 8H); 1.16–1.10 (m, 3H); 0.90–0.82 (m, 3H)

MS: m/z 482.4 (M+1)

EXAMPLE 15

3-(4-{2-[(Bicylo[4.2.0]octa-1,3,5-triene-7-carbonyl)-heptyl-amino]-ethyl}-phenyl)-2-ethoxy-propionic acid methyl ester:

¹H NMR δ(CDCl₃): 7.25–6.95 (m, 8H); 4.45–4.38 (m, 0.5H); 4.24–4.15 (m, 0.5H); 4.30–3.94 (m, 1H); 3.68 (s, 3H); 3.64–3.15 (m, 8H); 3.15–3.02 (m, 1H); 3.00–2.70 (m, 4H); 1.65–1.43 (m, 2H); 1.35–1.16 (m, 8H); 1.16–1.05 (m, 3H); 0.91–0.78 (m, 3H)

MS: m/z 480.3 (M+1)

EXAMPLE 16

2-Ethoxy-3-(4-{2-[heptyl-(1-p-tolyl-cyclopropanecarbonyl)-amino]-ethyl}-phenyl)-propionic acid methyl ester:

¹H NMR δ(CDCl₃): 7.15–7.00 (m, 7H); 6.78 (d, J=7.89 Hz, 1H); 4.02–3.95 (m, 1H); 3.68 (s, 3H); 3.62–3.52 (m, 1H); 3.47 (t, J=7.67 Hz, 1H); 3.41 (t, J=8.05 Hz, 1H); 3.38–3.26 (m, 2H); 3.11 (t, J=8.10 Hz, 1H); 2.82–2.25 (m, 3H); 1.61–1.50 (m, 1H); 1.40–1.16 (m, 8H); 1.16–0.97 (m, 9H); 0.95–0.80 (m, 4H)

MS: m/z 480.1 (M+1)

EXAMPLE 17

2-Ethoxy-3-{4-[2-(1-heptyl-3-methyl-3-p-tolyl-ureido)-ethyl]-phenyl}-propionic acid methyl ester:

¹H NMR δ(CDCl₃): 7.30–7.22 (m, 2H); 7.13–7.05 (m, 3H); 7.02–6.90 (m, 4H); 4.01–3.96 (m, 1H); 3.67 (s, 3H); 3.56 (dq, J=9.13, 7.05, 1H); 4.01–3.69 (m, 1H); 3.67 (s, 3H); 3.56 (dq, J=9.13, 7.05, 1H); 3.30 (dq, J=9.13, 7.05 Hz, 1H); 3.24 (t, J=7.68 Hz, 2H); 3.07 (s, 3H); 3.00 (t, J=7.48 Hz, 2H); 2.96–2.86 (m, 2H); 2.60 (t, J=7.68, 2H); 1.34 (quint, J=7.34, 2H); 1.29–1.00 (m, 8H); 1.12 (tm J=6.85 Hz, 3H); 0.85 (t, J=6.85 Hz, 3H).

MS: m/z 508.3 (M+1)

EXAMPLE 18

3-(4-{2-[3-(2,4-Dimethoxy-phenyl)-1-heptyl-ureido]-ethyl}-phenyl)-2-ethoxy-propionic acid:

A solution of 3-(4-{2-[3-(2,4-dimethoxy-phenyl)-1-heptyl-ureido]-ethyl}-phenyl)-2-ethoxy-propionic acid methyl ester (249 mg, 0.47 mmol) and 1 M LiOH (1.41 mmol, 1.41 mL) in tetrahydrofuran (2 mL) was allowed to stir at room temperature for 16 hours. The solution was quenched by the addition of 2 N HCl until the solution had a pH<2. After dilution with twice its volume in water, the aqueous layer was extracted with diethyl ether (2×). The organic layers were combined, washed with 2 M HCl (2×), dried over anhydrous sodium sulfate, and concentrated to give 3-(4-{2-[3-(2,4-dimethoxy-phenyl)-1-heptyl-ureido]-ethyl}-phenyl)-2-ethoxy-propionic acid as a clear oil (229 mg, 95%).

¹H NMR δ(CDCl₃): 8.04–7.97 (m, 1H); 7.18 (d, J=8.50 Hz, 2H); 7.15 (d, J=8.50, 2H); 6.82 (s, 1H); 6.48–6.43 (m, 2H); 4.04 (dd, J=7.67, 4.15 Hz, 1H); 3.83 (s, 3H); 3.77 (s, 3H); 3.56 (dq, J=9.13, 6.99 Hz, 1H); 3.48 (t, J=7.78 Hz, 2H); 3.41 (dq, J=9.13, 7.05 Hz, 1H); 3.13 (t, J=7.68 Hz, 2H); 3.09 (dd, J=14.11, 4.35 Hz, 1H); 2.96 (dd, J=14.11, 7.68 Hz, 1H); 2.88 (t, J=7.71 Hz, 2H); 1.68 (quint, J=7.17 Hz, 2H); 1.34–1.19 (m, 8H); 1.14 (t, J=7.06 Hz, 3H); 0.86 (t, J=6.84 Hz, 3H)

MS: m/z 515.4 (M+1)

EXAMPLE 19

3-(4-{2-[3-(2,4-Difluoro-phenyl)-1-heptyl-ureido]-ethyl}-phenyl)-2-ethoxy-propionic acid:

A solution of 3-(4-{2-[3-(2,4-difluoro-phenyl)-1-heptyl-ureido]-ethyl}-phenyl)-2-ethoxy-propionic acid methyl ester (44 mg, 0.087 mmol) and 1 M LiOH (0.26 mmol, 0.26 mL) in tetrahydrofuran (2 mL) was allowed to stir at room temperature for 94 hours. The solution was quenched by the addition of 2 N HCL until the solution had a pH<2. After dilution with twice its volume in water, the aqueous layer was extracted with diethyl ether (2×). The organic layers were combined, washed with 2 M HCl (2×), dried over anhydrous sodium sulfate, and concentrated to a crude oil. The oil was chromatographed on silica gel (15% methanol/methylene chloride) to give 3-(4-{2-[3-(2,4-difluoro-phenyl)-1-heptyl-ureido]-ethyl}-phenyl)-2-ethoxy-propionic acid as a white waxy-solid (26.3 mg, 62%).

¹H NMR δ(CDCl₃): 7.94 (br.s, 1H); 7.17 (d, J=6.23 Hz, 2H); 7.09 (d, J=6.65 Hz, 2H); 6.85–6.70 (m, 2H); 6.33 (br.s, 1H); 3.96 (br.s, 1H); 3.65–3.37 (m, 3H); 3.30 (br.s, 1H); 3.18 (t, J=7.08 Hz, 2H); 3.10–2.98 (m, 1H); 2.92 (br.s, 1H); 2.82 (br.s, 2H); 1.56 (br.s, 2H); 1.35–1.15 (m, 8H); 1.01 (br.s, 3H); 0.84 (t, J=6.23 Hz, 3H)

MS: m/z 491.1 (M+1)

EXAMPLE 20

3-[4-(2-{[(2,4-Difluoro-phenyl)-acetyl]-heptyl-amino}-ethyl)-phenyl]-2-ethoxy-propionic acid:

A solution of 3-[4-(2-{[(2,4-difluoro-phenyl)-acetyl]-heptyl-amino}-ethyl)-phenyl]-2-ethoxy-propionic acid methyl ester (35 mg, 0.07 mmol) and 1 M LiOH (0.208 mmol, 0.208 mL) in tetrahydrofuran (1 mL) was allowed to stir at room temperature for 78 hours. 2 N HCL was added until the solution had a pH<2. After dilution with twice its volume in water, the aqueous layer was extracted with diethyl ether (2×). The organic layers were combined, washed with 2M HCl (2×), dried over anhydrous sodium sulfate, and concentrated to give 3-[4-(2-{[(2,4-difluoro-phenyl)-acetyl]-heptyl-amino}-ethyl)-phenyl]-2-ethoxy-propionic acid as a clear oil (28.6 mg, 84%).

¹H NMR δ(CDCl₃): 7.30–7.02 (m, 5H); 6.90–6.68 (m, 2H); 4.06–3.98 (m, 1H); 3.63 (s, 1H); 3.62–3.55 (m, 1H); 3.55–3.45 (m, 2H); 3.45–3.26 (m, 3H); 3.13 (t, J=7.89 Hz, 1H); 3.10–3.02 (m, 1H) 3.02–2.90 (m, 1H); 2.85–2.75 (m, 2H); 1.57–1.44 (m, 2H); 1.35–1.17 (m, 8H); 1.17–1.10 (m, 3H); 0.90–0.80 (m, 3H)

MS:m/z 490.4 (M+1)

EXAMPLE 21

2-Ethoxy-3-{4-[2-(1-heptyl-3-p-tolyl-ureido)-ethyl]-phenyl}-propionic acid:

A solution of 2-ethoxy-3-{4-[2-(1-heptyl-3-p-tolyl-ureido)-ethyl]-phenyl}-propionic acid methyl ester (40 mg, 0.083 mmol) and 1 M LiOH (0.25 mmol, 0.25 mL) in tetrahydrofuran (2 mL) was allowed to stir at room temperature for 16 hours. The solution was quenched by the addition of 2 N HCl until the solution had a pH<2. After dilution with twice its volume in water, the aqueous layer was extracted with diethyl ether (2×). The organic layers were combined, washed with 2 M HCl (2×), dried over anhydrous sodium sulfate, and concentrated to a crude oil. The crude oil was chromatographed on silica gel (2% methanol/methylene chloride gradient to 15% methanol/methylene chloride) to give 2-ethoxy-3-{4-[2-(1-heptyl-3-p-tolyl-ureido)-ethyl]-phenyl}-propionic acid as a white waxy-solid (32 mg, 82%).

$^1$H NMR δ(CDCl$_3$):7.22–6.95 (m, 8H); 6.02 (s, 1H); 3.99 (dd, J=7.47, 3.67 Hz, 1H); 3.60–3.41 (m, 3H); 3.40–3.26 (m, 1H); 3.18 (t, J=7.33 Hz, 2H); 3.05 (dd, J=14.65 Hz, 3.42 Hz, 1H); 2.93 (dd, J=14.40, 8.60 Hz, 1H); 2.82 (t, J=6.84 Hz, 2H); 2.24 (s, 3H); 1.56 (quint, J=6.58 Hz, 2H); 1.35–1.15 (m, 8H); 1.08 (t, J=6.50, 3H)

EXAMPLE 22

2-Ethoxy-3-{4-[2-(heptyl-p-tolylacetyl-amino)-ethyl]-phenyl}-propionic acid:

A solution of 2-ethoxy-3-{4-[2-(heptyl-p-tolylacetyl-amino)-ethyl]-phenyl}-propionic acid methyl ester (21 mg, 0.044 mmol) and 1 M LiOH (0.131 mmol, 0.131 mL) in tetrahydrofuran (1 mL) was allowed to stir at room temperature for 24 hours. 2 N HCL was then added until the solution had a pH<2. After dilution with twice its volume in water, the aqueous layer was extracted with diethyl ether (2×). The organic layers were combined, washed with 2 M HCl (2×), dried over anhydrous sodium sulfate, and concentrated to give 2-ethoxy-3-{4-[2-(heptyl-p-tolylacetyl-amino)-ethyl]-phenyl}-propionic acid as a clear oil (19.5 mg, 95%).

$^1$H NMR δ(CDCl$_3$): 7.20–6.97 (m, 8H); 4.06–4.00 (m, 1H); 3.64(s, 1H); 3.63–3.52 (m, 1H); 3.52–3.45 (m, 1H); 3.45–3.52 (m, 4H); 3.12–2.90 (m, 3H); 2.83–2.65 (m, 2H); 2.34–2.26 (m, 3H); 1.60–1.35 (m, 2H); 1.35–1.10 (m, 11H); 0.90–0.83 (m, 3H)

MS: m/z 468.4 (M+1)

EXAMPLE 23

3-(4-{1-[3-(2,4-Difluoro-phenyl)-1-heptyl-ureidomethyl]-cyclopropyl}-phenyl)-2-ethoxy-propionic acid:

A solution of 3-(4-{1-[3-(2,4-difluoro-phenyl)-1-heptyl-ureidomethyl]-cyclopropyl}-phenyl)-2-ethoxy-propionic acid methyl ester (50 mg, 0.094 mmol) and 1 M LiOH (0.283 mmol, 0.283 mL) in tetrahydrofuran (1 mL) was allowed to stir at room temperature for 18 hours. 2 N HCL was then added until the solution had a pH<2. After dilution with twice its volume in water, the aqueous layer was extracted with diethyl ether (2×). The organic layers were combined, washed with 2 M HCl (2×), dried over anhydrous sodium sulfate, and concentrated to give 3-(4-{1-[3-(2,4-difluoro-phenyl)-1-heptyl-ureidomethyl]-cyclopropyl}-phenyl)-2-ethoxy-propionic acid as a clear oil (30 mg, 61%).

EXAMPLE 24

3-(4-{2-[(Bicyclo[4.2.0]octa-1(6),2,4-triene-7-carbonyl)-heptyl-amino]-ethyl}-phenyl)-2-ethoxy-propionic acid:

A solution of 3-(4-{2-[(bicyclo[4.2.0]octa-1(6),2,4-triene-7-carbonyl)-heptyl-amino]-ethyl}-phenyl)-2-ethoxy-propionic acid methyl ester (96 mg, 0.20 mmol) and 1 M LiOH (0.60 mmol, 0.60 mL) in tetrahydrofuran (3 mL) was allowed to stir at room temperature for 16 hours. 2 N HCL was then added until the solution had a pH<2. After dilution with twice its volume in water, the aqueous layer was extracted with diethyl ether (2×). The organic layers were combined, washed with 2 M HCl (2×), dried over anhydrous sodium sulfate, and concentrated to give 3-(4-{2-[(bicyclo[4.2.0]octa-1(6),2,4-triene-7-carbonyl)-heptyl-amino]-ethyl}-phenyl)-2-ethoxy-propionic acid as a clear oil (56 mg, 60%).

$^1$H NMR δ(CDCl$_3$): 7.25–6.90 (m, 8H); 4.454.15 (m, 1H); 4.05–3.95 (m, 1H); 3.80–3.20 (m, 7H); 3.20–2.70 (m, 5H); 1.70–1.45 (m, 2H); 1.35–1.16 (m, 8H); 1.16–1.05 (m, 3H); 0.91–0.75 (m, 3H)

MS: m/z 466.3 (M+1)

EXAMPLE 25

2-Ethoxy-3-(4-{2-[heptyl-(1-p-tolyl-cyclopropanecarbonyl)-amino]-ethyl}-phenyl)-propionic acid:

A solution of 2-ethoxy-3-(4-{2-[heptyl-(1-p-tolyl-cyclopropanecarbonyl)-amino]-ethyl}-phenyl)-propionic acid methyl ester (94 mg, 0.185 mmol) and 1 M LiOH (0.60 mmol, 0.60 mL) in tetrahydrofuran (1 mL) was allowed to stir at room temperature for 16 hours. 2 N HCL was then added until the solution had a pH<2. After dilution with twice its volume in water, the aqueous layer was extracted with diethyl ether (2×). The organic layers were combined, washed with 2 M HCl (2×), dried over anhydrous sodium sulfate, and concentrated to give 2-ethoxy-3-(4-{2-[heptyl-(1-p-tolyl-cyclopropanecarbonyl)-amino]-ethyl}-phenyl)-propionic acid as a clear oil (60 mg, 66%).

$^1$H NMR δ(CDCl$_3$): 7.20–7.00 (m, 7H); 6.79 (d, J=7.89 Hz, 1H); 4.06–3.97 (m, 1H); 3.67–3.55 (m, 1H); 3.55–3.30 (m, 4H); 3.17–3.00 (m, 2H); 3.00–2.90 (m, 1H); 2.80 (t, J=7.67 Hz, 1H); 2.87 (t, J=8.10 Hz, 1H); 2.82–2.27 (m, 3H); 1.61–1.50 (m, 1H); 1.40–1.00 (m, 1H); 1.40–1.00 (m, 15H); 0.97–0.80 (m, 4H)

MS: m/z 494.3 (M+1)

EXAMPLE 26

2-Ethoxy-3-{4-[2-(1-heptyl-3-methyl-3-phenyl-ureido)-ethyl]-phenyl}-propionic acid:

A solution of 2-ethoxy-3-{4-[2-(1-heptyl-3-methyl-3-phenyl-ureido)-ethyl]-phenyl}-propionic acid methyl ester (98 mg, 0.20 mmol) and 1 M LiOH (0.60 mmol, 0.60 mL) in tetrahydrofuran (1 mL) was allowed to stir at room temperature for 16 hours. 2 N HCL was then added until the solution had a pH<2. After dilution with twice its volume in water, the aqueous layer was extracted with diethyl ether (2×). The organic layers were combined, washed with 2 M HCl (2×), dried over anhydrous sodium sulfate, and concentrated to give 2-ethoxy-3-{4-[2-(1-heptyl-3-methyl-3-phenyl-ureido)-ethyl]-phenyl}-propionic acid as a clear oil (73 mg, 78%).

$^1$H NMR δ(CDCl$_3$): 7.30–7.20 (m, 2H); 7.14–7.04 (m, 3H); 7.02–6.90 (m, 4H); 3.98 (dd, J=7.48, 5.82 Hz, 1H); 3.67 (s, 1H); 3.56 (dq, J=9.14, 7.06 Hz, 1H); 3.30 (dq, J=7.48, 5.82 Hz, 1H); 3.24 (t, J=7.68 Hz, 2H); 3.07 (s, 3H); 3.00 (t, J=7.48 Hz, 2H); 2.96–2.86 (m, 2H); 2.60 (t, J=7.68 Hz, 2H); 1.34 (quint, 7.48 Hz, 2H); 1.29–1.00 (m, 8H); 1.12 (t, 6.85 Hz, 3H); 0.85 (t, J=6.85, 3H)

MS: m/z 469.9 (M+1)

EXAMPLE 27

1-p-Tolyl-cyclopropanecarboxylic acid heptylamide:

To a solution of 1-p-tolylcyclopropanecarboxylic acid (5.68 grams) in chloroform (10 mL) was added thionyl chloride (17.0 mmol, 1.26 mL). The resulting mixture was brought to reflux and was allowed to stir for 3 h. The mixture was cooled to room temperature and concentrated to give a yellow oil. The oil was dissolved in dichloromethane (5 mL) and added dropwise to a solution of 1-heptylamine (6.82 mmol, 1.01 mL) and N,N-diisopropylethylamine (6.82 mmol, 1.19 mL) dissolved in dichloromethane (10 mL) cooled to 0° C. The mixture was warmed to room temperature and was allowed to stir for 30 minutes. The solution was poured over 1 N HCl, and the aqueous layer was isolated and extracted with dichloromethane (3×). The organic layers were combined, washed with 2N HCl (1×), brine (1×), dried over anhydrous sodium sulfate and concentrated to a yellow oil which solidified under high vacuum. The solid was crystallized from hexanes to give 1-p-tolyl-cyclopropanecarboxylic acid heptylamide as a white solid (1.0 g, 64%).

¹H NMR δ(CDCl₃): 7.26 (d, J=8.09 Hz, 2H); 7.15 (d, J=7.89 Hz, 2H); 5.80 (br.s, 1H); 3.11 (dt, J=7.07, 6.02 Hz, 2H); 2.84 (s, 3H); 1.57–1.51 (m, 2H); 1.82 (quint, J=6.85 Hz, 2H); 1.27–1.07 (m, 8H); 1.00–0.95 (m, 2H); 0.84 (t, J=6.95 Hz, 3H)

MS: m/z 275.4 (M+1)

EXAMPLE 28

1-(4-Hydroxymethyl-phenyl)-cyclopropanecarboxylic acid heptylamide:

To a solution of 1-p-tolyl-cyclopropanecarboxylic acid heptylamide (950 mg, 3.48 mmol) in tetrachloromethane (20 mL) was added bromine (3.48 mmol, 553 mg). The resulting mixture was irradiated and brought to reflux with a 250 W light source. After the bromine color had dissipated from the solution the mixture was cooled and concentrated to an orange tinged oil. This was dissolved in water/dioxane (50 mL/50 mL) and precipitated calcium carbonate (61.5 mmol, 6.2 g) was added. The mixture was brought to reflux for 4 h, cooled to room temperature and the dioxane was evaporated under reduced pressure. Water and dichloromethane were added to the residue and 2N HCl was added to this mixture until all solid had dissolved. The aqueous layer was extracted with dichloromethane (2×). The organic layers were washed with brine (2×), dried over anhydrous sodium sulfate and concentrated to a crude orange oil. The oil was chromatographed (30 g SiO₂, 5% methanol/dichloromethane) to give a mixture of 1-(4-hydroxymethyl-phenyl)-cyclopropanecarboxylic acid heptylamide and an impurity 1-p-tolyl-acid heptyl amide (1.0 g, 8.3%).

¹H NMR δ(CDCl₃): 7.42–7.35 (m, 2H); 4.72 (s, 2H); 3.13 (dt, J=7.27, 6.23 Hz, 2H); 2.35 (s, 3H); 1.63–1.56 (m, 2H); 1.34 (quint, J=6.85 Hz, 2H); 1.30–1.12 (m, 8H); 1.10–1.05 (m, 2H); 0.86 (t, J=7.06 Hz, 3H)

EXAMPLE 29

[4-(1-Heptylaminomethyl-cyclopropyl)-phenyl]-methanol:

To a stirred solution of the mixture containing 1-(4-hydroxymethyl-phenyl)-cyclopropanecarboxylic acid heptylamide (Example 28, 1.0 g) in tetrahydrofuran (30 mL) under an nitrogen atmosphere cooled to 0° C. was added sodium borohydride (20.7 mmol, 783 mg) in one portion followed by the dropwise addition of boron trifluoride diethyletherate (27.6 mmol, 3.50 ml). The heterogeneous white mixture was allowed to stir at room temperature for 16 hours. The mixture was cooled to 0° C. and 2 M HCl was added until gas evolution ceased, then was heated to 80° C. for 45 minutes. The mixture was cooled to room temperature and concentrated under reduced pressure to a white solid. The solid was suspended in water (50 mL), then treated with 2 M NaOH in order to bring the pH to 14. The basic solution was extracted with diethyl ether (3×). The organic layers were washed with brine (2×), dried over anhydrous sodium sulfate, and concentrated to give impure [4-(1-heptylaminomethyl-cyclopropyl)-phenyl]-methanol as a clear oil. The crude oil was used in the preparation of heptyl-[1-(4-hydroxymethyl-phenyl)-cyclopropylmethyl]-carbamic acid tert-butyl ester without further purification.

¹H NMR δ(CDCl₃): 7.40–7.05 (m, 4H); 4.63 (s, 2H); 2.73 (s, 2H); 2.58 (t, J=7.47 Hz, 2H); 1.50–1.35 (m, 2H); 1.30–1.10 (m, 8H); 0.90–0.60 (m, 6H)

MS: m/z 276.2 (M+1)

EXAMPLE 30

Heptyl-[1-(4-hydroxymethyl-phenyl)-cyclopropylmethyl]-carbamic acid tert-butyl ester:

To a beaker containing saturated NaHCO₃ (10 mL) and impure [4-(1-heptylaminomethyl-cyclopropyl)-phenyl]-methanol (~3.35 mmol) dissolved in tetrahydrofuran (2 mL) was added di-tert-butyl dicarbonate (6.7 mmol, 1.46 g). To the stirred solution was added 2M NaOH in order to keep the pH of the solution between 8 and 9. The mixture was allowed to stir at room temperature for 1 h. The mixture was extracted with diethyl ether (3×). The organic layers were combined, washed with brine (1×), dried over anhydrous sodium sulfate, and concentrated to a clear oil. The crude oil was purified by flash chromatography (Merck silica gel 60, art#9385-3) eluting with 5% methanol/methylene chloride, then 30% ethyl acetate/hexanes) to give heptyl-[1-(4-hydroxymethyl-phenyl)-cyclopropylmethyl]-carbamic acid tert-butyl ester as a clear oil (850 mg, 68%).

¹H NMR δ(CDCl₃): 7.35–7.22 (m, 4H); 4.63 (s, 2H); 3.50–3.30 (m, 2H); 3.20–3.29 (m, 2H); 1.50–1.05 (m, 19H); 0.90–0.70 (m, 6H)

MS: m/z 276.2 (M+1)

EXAMPLE 31

[1-(4-Formyl-phenyl)-cyclopropylmethyl]-heptyl-carbamic acid tert-butyl ester:

To a stirred solution of heptyl-[1-(4-hydroxymethyl-phenyl)-cyclopropylmethyl]-carbamic acid tert-butyl ester (850 mg, 2.24 mmol) in anhydrous diethyl ether (25 mL) under an nitrogen atmosphere was added activated manganese dioxide (Aldrich, 2.25 g). The solution was allowed to stir at room temperature for 2 hours. An additional 1 g of manganese dioxide was added and the mixture was stirred for 2 hours. The heterogeneous black mixture was filtered through a Celite plug and was washed exhaustively with methylene chloride. The clear filtrate was concentrated to a crude yellow tinged oil. The crude mixture was purified by flash chromatography (15% ethyl acetate/hexanes) to give [1-(4-formyl-phenyl)-cyclopropylmethyl]-heptyl-carbamic acid tert-butyl ester as a clear oil (640 mg, 77%).

¹H NMR δ(CDCl₃): 9.96 (s, 1H); 7.78 (d, 7.89 Hz, 2H); 7.47 (d, 7.89 Hz, 2H); 3.60–3.35 (m, 2H), 1.59–1.05 (m, 19H); 0.94–0.79 (m, 6H)

MS:m/z 274.3 (M+1)

EXAMPLE 32

3-(4-{1-[(tert-Butoxycarbonyl-heptyl-amino)-methyl]-cyclopropyl}-phenyl)-2-ethoxy-acrylic acid ethyl ester:

A suspension of sodium hydride, 60% in an oil dispersion, (3.43 mmol, 137 mg) in anhydrous tetrahydrofuran (10 mL) under an nitrogen atmosphere was cooled to 0° C. To the suspension was added [1-(4-formyl-phenyl)-cyclopropylmethyl]-heptyl-carbamic acid tert-butyl ester (1.66 mmol, 620 mg) followed by 2-diphenylphosphinoyl-2-ethoxyacetic acid ethyl ester (5.2 mmol, 1.8 g). The white heterogeneous mixture was heated to reflux for 20 min, then cooled to room temperature. The thick heterogeneous mixture was quenched by the addition of ethanol, then was diluted with water (30 mL) and extracted with diethyl ether (3×). The organic layers were combined, washed with saturated NaHCO₃ (2×), brine (1×), dried over anhydrous sodium sulfate and concentrated to give an oil which was chromatographed on silica gel (Merck silica gel 60, art#9385-3) eluting with 15% ethyl acetate/hexanes to give a mixture of E and Z isomers of 3-(4-{1-[(tert-butoxycarbonyl-heptyl-amino)-methyl]-cyclopropyl}-phenyl)-2-ethoxy-acrylic acid ethyl ester as a clear oil (690 mg, 85%).

¹H NMR δ(CDCl₃): 7.67 (d, J=8.31 Hz, 2H); 7.33–7.26 (m, 2H); 6.94 (s, 1H major isomer); 5.29 (s, 1H, minor isomer); 4.28 (q, J=7.06, 2H, major isomer); 4.11 (q, J=7.07 Hz, 2H minor isomer); 3.96 (q, J=7.07 Hz, 2H, major isomer); 3.50–3.32 (m, 2H); 3.20–2.85 (m, 2H); 1.50–1.05 (m, 25H); 0.91–0.70 (m, 6H)

MS: m/z 388.4 (M+1)

EXAMPLE 33

3-(4-{1-[(tert-Butoxycarbonyl-heptyl-amino)-methyl]-cyclopropyl}-phenyl)-2-ethoxy-propionic acid methyl ester:

To a solution of 3-(4-{1-[(tert-butoxycarbonyl-heptyl-amino)-methyl]-cyclopropyl}-phenyl)-2-ethoxy-acrylic acid ethyl ester (680 mg, 1.40 mmol) in anhydrous methanol (20 mL) in a flame dried round bottom flask under an nitrogen atmosphere was added magnesium turnings (53.50 mmol, 85 mg). After 30 min, 1,2-dibromoethane (1 drop) was added directly to the magnesium turnings via pipette, initiating $H_2$ gas evolution from the magnesium. At this time a dry stir bar was added and the mixture was stirred at room temperature until all of the magnesium solid had dissolved. Two additional portions of magnesium (80 mg) were added and allowed to dissolve (16 h). The mixture was poured over 25 mL of ice cooled 2NHCl. The acidic mixture was brought to pH 8.5 by the addition of concentrated aqueous ammonia, then was extracted with diethyl ether (3x). The organic layers were combined, washed with saturated NaCl (3x), dried over anhydrous sodium sulfate, and concentrated under reduced pressure to give 3-(4-{1-[(tert-butoxycarbonyl-heptyl-amino)-methyl]-cyclopropyl}-phenyl)-2-ethoxy-propionic acid methyl ester as a clear oil (580 mg, 87%).

$^1$H NMR δ(CDCl$_3$): 7.21 (d, J=7.89 Hz, 2H); 7.11 (d, J=7.89 Hz, 2H); 3.98 (dd, J=7.47, 5.81 Hz, 1H); 3.69 (s, 3H); 3.56 (dq, J=9.13, 7.05 Hz, 1H); 3.47–3.00 (m, 2H); 3.31 (dq, J=9.13, 7.05, 1H); 3.13–3.00 (m, 1H); 3.00–2.85 (m, 3H); 1.50–1.05 (m, 22H); 1.13 (t, J=6.85, 3H); 0.85(t, J=6.85 Hz, 3H); 0.83–0.65 (m, 4H)

MS: m/z 475 (M+1)

EXAMPLE 34

2-Ethoxy-3-[4-(1-heptylaminomethyl-cyclopropyl)-phenyl]-propionic acid methyl ester:

A solution of 3-(4-{1-((tert-butoxycarbonyl-heptyl-amino)-methyl]-cyclopropyl}-phenyl)-2-ethoxy-propionic acid methyl ester (1.29 mmol, 615 mg) in ethyl acetate (20 mL) under a nitrogen atmosphere was cooled to −78° C., and saturated with HCl gas. The solution was allowed to warm to room temperature and the solvent was evaporated, leaving the 2-ethoxy-3-[4-(1-heptylaminomethyl-cyclopropyl)-phenyl]-propionic acid methyl ester as its HCl salt (531 mg, 100%).

EXAMPLE 35

3-(4-{1-[3-(2,4-Difluoro-phenyl)-1-heptyl-ureidomethyl]-cyclopropyl}-phenyl)-2-ethoxy-propionic acid methyl ester:

To a solution of 2-ethoxy-3-[4-(1-heptylaminomethyl-cyclopropyl)-phenyl]-propionic acid methyl ester (54 mg, 0.13 mmol), and 2,4-difluorophenylisocyanate (0.156 mmol, 0.0185 mL) in toluene (2.5 mL) was added N,N-diisopropylethylamine (0.29 mmol, 0.050 mL). The mixture was allowed to stir at room temperature for 18 hours, then was poured over 1 M HCl (5 mL). The aqueous layer was isolated and extracted with diethyl ether (2x). The organic layers were combined, washed with 2 M HCl (1x), brine (1x), dried over anhydrous sodium sulfate, and concentrated to give a clear film. The crude product was chromatographed on silica (Merck silica gel 60, art#9385-3) eluting with 20% ethyl acetate/hexanes to give 3-(4-{1-[3-(2,4-difluoro-phenyl)-1-heptyl-ureidomethyl]-cyclopropyl}-phenyl)-2-ethoxy-propionic acid methyl ester as a clear film (50 mg, 73%).

$^1$H NMR δ(CDCl$_3$): 7.90–7.80 (m, 1H); 7.27 (d, J=7.89 Hz, 2H); 7.15 (d, J=7.88 Hz, 2H); 6.81–6.70 (m, 2H); 6.19 (d, J=2.49 Hz, 2H); 3.94 (dd, J=7.47, 5.81 Hz, 1H); 3.67 (s, 3H); 3.63 (dq, J=9.13, 7.05, 1H); 3.48 (br.s, 2H); 3.25 (dq, J=9.13, 7.05 Hz, 1H); 3.09 (t, J=7.68 Hz, 2H); 2.95–2.87 (m, 2H); 1.49 (quint, J=7.06 Hz, 2H); 1.32–1.13 (m, 8H); 1.10 (t, J=7.06 Hz, 3H); 0.95–0.80 (m, 6H)

MS: m/z 531.1 (M+1)

EXAMPLE 36

3-(4-{1-[3-(2,4-Difluoro-phenyl)-1-heptyl-ureidomethyl]-cyclopropyl}-phenyl)-2-ethoxy-propionic acid:

A solution of 3-(4-{1-[3-(2,4-difluoro-phenyl)-1-heptyl-ureidomethyl]-cyclopropyl}-phenyl)-2-ethoxy-propionic acid methyl ester (50 mg, 0.094 mmol) and 1 M LiOH (0.283 mmol, 0.283 mL) in tetrahydrofuran (1 mL) was allowed to stir at room temperature for 18 hours. 2 N HCL was then added until the solution had a pH<2. After dilution with twice its volume in water, the aqueous layer was extracted with diethyl ether (2x). The organic layers were combined, washed with 2 M HCl (2x), dried over anhydrous sodium sulfate, and concentrated to give 3-(4-{1-[3-(2,4-difluoro-phenyl)-1-heptyl-ureidomethyl]-cyclopropyl}-phenyl)-2-ethoxy-propionic acid as a clear oil (29.6 mg, 61%).

$^1$H NMR δ(CDCl$_3$): 7.92–7.80 (m, 1H); 7.28 (d, J=7.89 Hz, 2H); 7.16 (d, J=7.90, 2H); 6.76 (t, J=8.72 Hz, 2H); 6.21 (d, J=2.50 Hz, I H); 3.99 (dd, J=7.89 Hz, 2H); 3.59–3.42 (m, 3H); 3.35 (dq, J=8.73, 7.07 Hz, 1H); 3.13–3.05 (m, 2H); 3.04 (dd, J=14.13, 4.16 Hz, 1H); 2.92 (dd, J=13.71, 7.47 Hz, 1H); 1.49 (quint, J=7.05 Hz, 2H) 1.31–1.15 (m, 8H); 1.10 (t, J=6.84 Hz, 3H); 0.95–0.80 (m, 6H)

MS: m/z 517.2 (M+1)

EXAMPLE 37

3-(4-Carboxymethyl-phenyl)-2,2-dimethyl-propionic acid ethyl ester:

To a solution of diisopropylamine (13.11 mmol, 1.8 mL) in anhydrous tetrahydrofuran (40 mL) cooled to −78° C. under a nitrogen atmosphere was added 2.5M n-BuLi in hexanes (13.11 mmol, 5.24 mL). The resulting solution was allowed to stir at −78° C. for 20 minutes, warmed to room temperature for 10 minutes, then cooled back to −78° C. for 10 minutes. The mixture was added to a solution of ethyl isobutyrate (13.11 mmol, 1.76 mL) dissolved in anhydrous tetrahydrofuran (20 mL) cooled to −78° C. The resulting solution was allowed to stir at −78° C. for 1 h. (4-Bromomethyl-phenyl)-acetic acid (1 g, 4.37 mmol) in anhydrous tetrahydrofuran (10 mL) was added to the solution dropwise. The solution was warmed to room temperature and was allowed to stir for 20 minutes. The reaction mixture was poured over a dilute HCl solution (1 N). The aqueous layer was isolated and extracted with diethyl ether (1x). The organic layers were combined, washed with 2N HCl (2x), brine (1x), dried over anhydrous sodium sulfate, and concentrated to a crude oil. The oil was chromatographed on silica gel (Merck silica gel 60, art#9385-3) eluting with 10% methanol/methylene chloride to give 3-(4-carboxymethyl-phenyl)-2,2-dimethyl-propionic acid ethyl ester as a white solid (0.97 g, 84%).

$^1$H NMR δ(CDCl$_3$): 7.14 (d, J=7.89 Hz, 2H); 7.05 (d, J=7.89 Hz, 2H); 4.09 (q, J=7.16 Hz, 2H); 3.56 (s, 2H); 2.81 (s, 2H); 1.21 (t, J=7.27 Hz, 3H); 1.14 (s, 6H)

EXAMPLE 38

3-(4-Heptylcarbamoylmethyl-phenyl)-2,2-dimethyl-propionic acid ethyl ester:

To a stirred solution of 3-(4-carboxymethyl-phenyl)-2,2-dimethyl-propionic acid ethyl ester (0.97 g, 3.67 mmol) in chloroform (15 mL) under an nitrogen atmosphere was added thionyl chloride (11 mmol, 0.804 mL). The mixture was heated under reflux for 2.75 hours, cooled to room temperature and concentrated under reduced pressure to a clear oil. The oil was dissolved in methylene chloride (0.50 mL) then added dropwise to a solution of 1-heptylamine (4.40 mmol, 0.653 mL) and N,N-diisopropylethylamine (4.40 mmol, 0.765 mL) in anhydrous dichloromethane (5 mL) cooled to 0° C. The solution was warmed to room temperature and allowed to stir for 30 minutes, then was poured over a solution of 1 M HCl (10 mL). The aqueous layer was isolated and extracted with diethyl ether (2×). The organic layers were combined, washed with 2N HCl (2×), brine (1×), dried over anhydrous sodium sulfate and concentrated under reduced pressure to give crude 3-(4-heptylcarbamoylmethyl-phenyl)-2,2-dimethyl-propionic acid ethyl ester as an orange oil. The oil was used in the preparation of 3-[4-(2-heptylamino-ethyl)-phenyl]-2,2-dimethyl-propionic acid ethyl ester without further purification. (1.27 g, 95%).

$^1$H NMR δ(CDCl$_3$): 7.12 (d, J=8.31 Hz, 2H); 7.08 (d, J=7.89 Hz, 2H); 5.29 (br.s, 1H); 4.10 (q, J=7.06 Hz, 2H); 3.61 (s, 2H); 3.16 (q, J=6.65 Hz, 2H); 2.83 (s, 2H); 1.88 (quint, J=6.86 Hz, 2H); 1.22 (t, J=7.06 Hz, 3H); 1.23–1.17 (m, 8H); 1.15 (s, 6H); 0.84 (t, J=6.86 Hz, 3H).

MS: m/z 362.4 (M+1)

EXAMPLE 39

3-[4-(2-Heptylamino-ethyl)-phenyl-2,2-dimethyl-propionic acid ethyl ester:

To a stirred solution of 3-(4-heptylcarbamoylmethyl-phenyl)-2,2-dimethyl-propionic acid ethyl ester (1.2 g, 3.32 mmol) in tetrahydrofuran (30 mL) under an nitrogen atmosphere cooled to 0° C. was added sodium borohydride (9.96 mmol, 377 mg) in one portion followed by the dropwise addition of boron trifluoride diethyl etherate (13.28 mmol, 1.68 mL). The heterogeneous white mixture was allowed to stir at room temperature for 22 hours. The mixture was cooled to 0° C. and 2 M HCl was added until gas evolution ceased then was heated to 80° C. for 45 minutes. The mixture was cooled to room temperature and concentrated under reduced pressure to a white solid. The solid was suspended in water (50 mL), then treated with 2 M NaOH in order to bring the pH to 14. The basic solution was extracted with diethyl ether (3×). The organic layers were washed with brine (2×), dried over anhydrous sodium sulfate, and concentrated to give a clear oil which consisted of a mixture of 3-[4-(2-heptylamino-ethyl)-phenyl]-2,2-dimethyl-propionic acid ethyl ester and over-reduced alcohol (3-[4-(2-heptylamino-ethyl)-phenyl]-2,2-dimethyl-propan-1-ol) in an approximately 50:50 mixture.

$^1$H NMR δ(CDCl$_3$): 7.10–6.97 (m, 4H); 4.09 (q, J=7.16 Hz, 2H); 3.29 (s, 2H); 2.87–2.70 (m, 4H); 2.61–2.55 (m, 2H); 1.54–1.35 (m, 2H); 1.30–1.16 (m, 8H); 1.15 (s, 6H); 0.85 (t, J=6.95 Hz, 3H)

MS: m/z 348.4 (M+1)

EXAMPLE 40

3-[4-(2-Heptylamino-ethyl)-phenyl]-2,2-dimethyl-propionic acid:

To a solution of the impure 3-[4-(2-heptylamino-ethyl)-phenyl]-2,2-dimethyl-propionic acid ethyl ester (100 mg of the mixture) dissolved in methylene chloride (5 mL) cooled to −78° C. under a nitrogen atmosphere was added boron tribromide (1M in dichloromethane, 0.432 mL). The mixture was warmed to room temperature and stirred for 3 h. The mixture was cooled to −78° C. and an additional 0.432 mL of the 1M boron tribromide in dichloromethane was added. The mixture was warmed to room temperature and stirred for 20 minutes. The mixture was poured over H$_2$O (10 mL) and extracted with dichloromethane (3×). The organic layers were combined, dried over anhydrous sodium sulfate, and concentrated to a clear film. This was dissolved in dioxane/2M HCl (10 mL/10 mL) and was refluxed for 20 minutes. The mixture was cooled and brought to pH 10 with 2 N NaOH. The basic solution was washed with diethyl ether (3×) and brought to pH 4 with 2N HCL. The acidic solution was extracted with diethyl ether (3×), washed with brine (2×), dried over anhydrous sodium sulfate and concentrated to give 3-[4-(2-heptylamino-ethyl)-phenyl]-2,2-dimethyl-propionic acid as a clear film (23 mg, 46%).

$^1$H NMR δ(CDCl$_3$): 9.44 (br.s, 2H); 7.06 (d, J=7.90 Hz, 2H); 7.01 (d, J=7.90 Hz, 2H); 3.11 (s, 4H); 3.00–2.90 (m, 2H); 2.80 (s, 2H); 1.85 (q, J=7.37, 2H); 1.37–1.22 (m, 8H); 1.20 (s, 6H); 0.84 (t, J=6.65, 3H)

MS: m/z 320.3 (M+1)

EXAMPLE 41

3-(4-{2-[3-(2,4-Difluoro-phenyl)-1-hentyl-ureido]-ethyl}-phenyl)-2,2-dimethyl-propionic acid:

To a solution of 3-[4-(2-heptylamino-ethyl)-phenyl]-2,2-dimethyl-propionic acid (23 mg, 0.072 mmol), and N,N-diisopropylethylamine (0.152 mmol, 0.0264 mL) dissolved in toluene (2 mL) was added 2,4-difluorophenylisocyanate (0.0796 mmol, 0.0094 mL). The mixture was allowed to stir at room temperature for 72 hours, then was poured over 1 M HCl (5 mL). The aqueous layer was isolated and extracted with diethyl ether (2×). The organic layers were combined, washed with 2 M HCl (2×), brine (2×), dried over anhydrous sodium sulfate, and concentrated to give a clear film. The crude product was chromatographed on silica gel (Merck silica gel 60, art#9385-3) eluting with 5% methanol/methylene chloride to give 3-(4-{2-[3-(2,4-difluoro-phenyl)-1-heptyl-ureido]-ethyl}-phenyl)-2,2-dimethyl-propionic acid as a clear film (18.5 mg, 54%).

$^1$H NMR δ(CDCl$_3$): 8.05–7.94 (m, 1H); 7.12 (d, J=8.31 Hz, 2H); 7.09 (d, 2H, J=7.89 Hz); 6.87–6.75 (m, 2H); 6.28 (d, J=3.32 Hz, 1H); 3.50 (t, J=7.48 Hz, 2H); 3.18 (t, J 7.69 Hz, 2H); 2.87 (t, J=7.48 Hz, 2H); 2.84 (s, 2H); 1.57 (quint, J=6.86 Hz, 3H); 1.35–1.20 (m, 8H); 1.15 (s, 6H); 0.86 (t, J=6.86 Hz, 3H)

MS: m/z 475.3 (M+1)

EXAMPLE 42

2-(4-Bromo-phenyl)-N-heptyl-acetamide:

A stirred solution of (4-bromo-phenyl)-acetic acid (0.186 mol, 40.0 g) and thionyl chloride (0.558 mol, 40.0 mL) in chloroform (500 mL) under a N$_2$ atmosphere was heated under reflux for 20 hours. The mixture was cooled to room temperature and evaporated under vacuum to give an oil. This was dissolved in anhydrous methylene chloride (150 mL) and added dropwise to a solution of heptylamine (0.20 mol, 30.3 mL) and N,N-diisopropylethylamine (0.37 mol, 64.7 mL) in anhydrous methylene chloride cooled to 0° C. The mixture was stirred at room temperature for 45 minutes then poured into water and extracted with methylene chloride. The extract was washed with saturated brine, dried over anhydrous sodium sulfate and the solvent was removed under vacuum. The solid residue was purified by crystallization from ethyl acetate/hexanes to give 2-(4-bromo-phenyl)-N-heptyl-acetamide as a white solid. (37 g, 64%)

$^1$H NMR δ(CDCl$_3$): 7.46 (m, 2H) 7.12 (m, 2H); 3.49 (s, 2H); 3.17 (m, 2H); 1.40 (quint, 2H); 1.31–1.14 (m, 8H); 0.85 (t, 3H).

MS: m/z 312.1

EXAMPLE 43

[2-(4-Bromo-phenyl)-ethyl]-heptyl-amine:

Synthesized from 2-(4-bromo-phenyl)-N-heptyl-acetamide using a procedure analogous to that used for Example 3 to give [2-(4-bromo-phenyl)-ethyl]-heptyl-amine as a crude oil. The clear crude oil was used in the next step without purification. (32.7 g, 95%)

$^1$H NMR δ(CDCl$_3$):7.39 (m, 2H); 7.07 (m, 2H); 2.95–2.75 (m, 4H); 2.70–2.56 (m, 2H); 1.56–1.44 (m, 2H); 1.32–1.15 (m, 8H); 0.85 (t, 3H)

EXAMPLE 44

[2-(4-Bromo-phenyl)-ethyl]-heptyl-carbamic acid tert-butyl ester:

Synthesized from [2-(4-bromo-phenyl)-ethyl]-heptyl-amine using a procedure analogous to that used for Example 4. The crude oil was purified by chromatography on silica gel (Merck silica gel 60, art#9385-3) eluting with 20% ethyl acetate in hexanes to give [2-(4-bromo-phenyl)-ethyl]-heptyl-carbamic acid tert-butyl ester as a clear oil. (69.7 g, 99%)

$^1$H NMR δ(CDCl$_3$): 7.38 (m, 2H); 7.04 (m, 2H); 3.32 (t, 2H); 3.08 (t, 2H); 2.75 (t, 2H); 1.50–1.35 (m, 11H); 1.32–1.15 (m, 8H); 0.86 (t, 3H)

EXAMPLE 45

[2-(4-Formyl-phenyl)-ethyl]-heptyl-carbamic acid tert-butyl ester:

To a solution of [2-(4-bromo-phenyl)-ethyl]-heptyl-carbamic acid tert-butyl ester (20 g, 50.2 mmol) dissolved in tetrahydrofuran (200 mL) under a nitrogen atmosphere at −78° C. was added 1.3 M sec-BuLi in cyclohexane (100.5 mmol, 77.3 mL) dropwise. The solution was allowed to stir at −78° C. for 30 minutes. Anhydrous N,N-dimethylformamide (150.6 mmol, 11.6 mL) was added in one portion and the solution was allowed to warm to room temperature. After stirring for 30 minutes the mixture was poured over saturated NH$_4$Cl solution and extracted with diethyl ether (3×). The organic layers were combined, washed with water (1×), saturated brine (2×), dried over Na$_2$SO$_4$ and concentrated to a crude yellow oil. The oil was purified by chromatography on silica gel (Merck silica gel 60, art#9385-3) eluting with 20% ethyl acetate in hexanes to give impure [2-(4-formyl-phenyl)-ethyl]-heptyl-carbamic acid tert-butyl ester as a clear oil used directly in the following procedure. (11.62 g crude).

$^1$H NMR δ(CDCl$_3$): 9.96 (s, 1H); 7.79 (d, 2H); 7.39–7.31 (m, 2H); 3.39 (t, 2H); 3.16–3.00 (m, 2H); 2.95–2.85 (m, 2H); 1.50–1.37 (m, 11H); 1.33–1.15 (m, 8H); 0.86 (t, 3H)

MS: m/z 248.2 (M−Boc+1)

EXAMPLE 46

3-{4-[2-(tert-Butoxycarbonyl-heptyl-amino)-ethyl]-phenyl}-2-hydroxy-propionic acid ethyl ester:

To a solution of [2-(4-formyl-phenyl)-ethyl]-heptyl-carbamic acid tert-butyl ester (8 g crude, ~18.4 mmol) and ethyl chloroacetate (27.7 mmol, 2.73 mL) dissolved in anhydrous tetrahydrofuran (50 mL) was added NaH (60% oil dispersion, 27.7 mmol, 1.1 g). The mixture was allowed to stir at room temperature for 1 h, then was refluxed for 10 minutes. The mixture was cooled to room temperature and quenched by the addition of ethanol. The solution was diluted with water and extracted with ethyl acetate (3×). The organic layers were combined, washed with saturated brine (2×), dried over Na$_2$SO$_4$ and concentrated to a crude oil. The oil was dissolved in methanol (150 mL). To this solution was added ammonium formate (34.2 mmol; 2.16 g) and 10% Pd/C (170 mg). The mixture was heated to reflux for 2 h, then cooled to room temperature and filtered through Celite®. The filtrate was concentrated to a tan solid and redissolved in water. The aqueous solution was extracted with ethyl acetate (3×). The organic layers were combined, washed with brine (2×), dried over Na$_2$SO$_4$, and concentrated to a crude oil. The oil was purified by chromatography on silica gel (Merck silica gel 60, art#9385-3) eluting with 35% ethyl acetate in hexanes to give 3-{4-[2-(tert-butoxycarbonyl-heptyl-amino)-ethyl]-phenyl}2-hydroxy-propionic acid ethyl ester as a clear oil (3.17 g, 41%).

$^1$H NMR δ(CDCl$_3$): 7.15–7.07 (m, 4H); 4.39 (dd, 1H); 4.20 (q, 2H); 3.32 (t, 2H); 3.15–3.04 (m, 3H); 2.96–2.87 (m, 1H); 2.76 (t, 2H); 1.53–1.40 (m, 11H); 1.34–1.15 (m, 11H); 0.86 (t, 3H)

MS: m/z 335.9 (M−Boc+1)

EXAMPLE 47

2-Benzyloxy-3-{4-[2-(tert-butoxycarbonyl-heptyl-amino)-ethyl]-phenyl}-propionic acid ethyl ester:

To a solution of 3-{4-[2-(tert-butoxycarbonyl-heptyl-amino)-ethyl]-phenyl}-2-hydroxy-propionic acid ethyl ester (0.59 mmol, 250 mg) was added anhydrous CsOH (0.885 mmol, 148.6 mg) and freshly dried powdered 4 Angstrom molecular sieves (300 mg) followed by benzyl bromide (4.72 mmol, 0.56 mL). The mixture was allowed to stir for 16 hours. The mixture was poured into water and extracted with diethyl ether (3×). The organic layers were combined, washed with water (2×), brine (2×), dried over Na$_2$SO$_4$, and concentrated to a crude oil. The oil was purified by chromatography on silica gel (Merck silica gel 60, art#9385-3) eluting with 20% ethyl acetate in hexanes to give 2-benzyloxy-3-{4-[2-(tert-butoxycarbonyl-heptyl-amino)-ethyl]-phenyl}-propionic acid ethyl ester as a clear oil (180 mg, 58%).

$^1$H NMR δ(CDCl$_3$): 7.40–6.95 (m, 9H); 4.63 (d, 1H); 4.35 (d, 1H); 4.15 (q, 2H); 4.07 (dd, 1H); 3.40–3.25 (m, 2H); 3.18–2.90 (m, 4H); 2.78 (t, 2H); 1.50–1.36 (m, 11H); 1.33–1.15 (m, 11H; 0.86 (t, 3H)

MS: m/z 426.3 (M−Boc+1) Example 48

3-{4-[2-(tert-Butoxcarbonyl-heptyl-amino)-ethyl]-phenyl}-2-methoxy-propionic acid methyl ester:

Synthesized from 3-{4-[2-(tert-butoxycarbonyl-heptyl-amino)-ethyl]-phenyl}-2-hydroxy-propionic acid ethyl ester using a procedure analogous to that used for Example 47 and substituting methyl iodide as the electrophile to give 3-{4-[2-(tert-butoxycarbonyl-heptyl-amino)-ethyl]-phenyl}-2-methoxy-propionic acid methyl ester as a clear oil containing a mixture of methyl and ethyl ester (48 mg, 18%).

$^1$H NMR δ(CDCl$_3$): 7.20–7.00 (m, 4H); 4.16 (q, 2H, ethyl ester); 3.94 (s, 1H); 3.70 (s, 3H, methyl ester; 3.40–3.23 (m, 5H); 3.19–2.90 (m, 4H); 2.76 (t, 2H); 1.53–1.35 (m, 11H); 1.32–1.14 (m, 11H, includes ethyl ester signal); 0.85 (t, 3H)

MS: m/z 336.3 (m−Boc+1, methyl ester); 350.3 (M−Boc+1, ethyl ester)

EXAMPLE 49

2-Allyloxy-3-{4-[2-(tert-butoxycarbonyl-heptyl-amino)-ethyl]-phenyl}-propionic acid ethyl ester:

Synthesized from 3-{4-[2-(tert-butoxycarbonyl-heptyl-amino)-ethyl]-phenyl}-2-hydroxy-propionic acid ethyl ester using a procedure analogous to that used for Example 47 and substituting allyl bromide as the electrophile to give 2-allyloxy-3-{4-[2-(tert-butoxycarbonyl-heptyl-amino)-ethyl]-phenyl}-propionic acid ethyl ester as a clear oil (187 mg, 41%)

$^1$H NMR δ(CDCl$_3$): 7.20–6.99 (m, 4H); 5.96–5.68 (m, 1H); 5.32–5.00 (m, 2H); 4.15 (q, 2H); 4.11–4.00 (m, 1H); 3.89–3.80 (m, 1H); 3.41–3.21 (m, 2H); 3.19–2.92 (m, 4H); 2.85–2.66 (m, 2H); 1.54–1.33 (m, 11H); 1.32–1.13 (m, 11H); 0.85 (t, 3H).

MS: m/z 376.3 (M−Boc+1)

EXAMPLE 50

3-{4-[2-(tert-Butoxycarbonyl-heptyl-amino)-ethyl]-phenyl}-2-isopropylsulfanyl-propionic acid ethyl ester:

To a solution of 3-{4-[2-(tert-butoxycarbonyl-heptyl-amino)-ethyl]-phenyl}-2-hydroxy-propionic acid ethyl ester (0.69 mmol, 300 mg) dissolved in pyridine (3 mL) was added methanesulfonyl chloride (0.69 mmol, 0.534 mL). The mixture was stirred at room temperature overnight. A portion of the reaction mixture (0.115 mmol) was added to a solution containing 2-propane thiol (0.115 mmol, 0.107 mL) dissolved in anhydrous $CH_2Cl_2$ (2 mL). To this stirred solution was added a 1M solution of potassium tert-butoxide in tetrahydrofuran (0.115 mmol, 0.115 mL). The mixture was stirred overnight then poured over 1 M HCl. The mixture was extracted with diethyl ether (3×). The organic layers were combined, washed with 1 M HCl (2×), saturated brine (2×), dried over $Na_2SO_4$, and concentrated to a crude film. The film was purified by chromatography on silica gel (Merck silica gel 60, art#9385-3) eluting with 20% ethyl acetate in hexanes to give 3-{4-[2-(tert-butoxycarbonyl-heptyl-amino)-ethyl]-phenyl}-2-isopropylsulfanyl-propionic acid ethyl ester as a clear film containing an approximate 1:1 mixture of methyl and ethyl ester (30.2 mg, 55%).

$^1$H NMR δ($CDCl_3$): 7.15–7.00 (m, 4H); 4.20–4.04 (m, 2H, ethyl ester); 3.56 (s, 3H, methyl ester); 3.56–3.49 (m, 1H); 3.37–3.24 (m, 2H); 3.20–2.94 (m, 4H); 2.94–2.86 (m, 1H); 2.76 (t, 2H); 1.50–1.35 (m, 11H); 1.32–1.13 (m, 17H, ethyl ester within multiplet); 0.86 (t, 3H)

MS: m/z 380.2 (M−Boc+1)

EXAMPLE 51

2-Benzylsulfanyl-3-{4-[2-(tert-butoxycarbonyl-heptyl-amino)-ethyl]-phenyl}-propionic acid ethyl ester:

Synthesized from 3-{4-[2-(tert-butoxycarbonyl-heptyl-amino)-ethyl]-phenyl}-2-hydroxy-propionic acid ethyl ester using a procedure analogous to that used for Example 50 and substituting benzylthiol as the nucleophile to give an approximate 1:1 mixture of ethyl and methyl ester as a clear film (58 mg, 95%).

$^1$H NMR δ($CDCl_3$): 7.35–7.15 (m, 5H); 7.15–6.95 (m, 4H); 4.16–4.03 (m, 2H, ethyl ester); 3.85–3.70 (m, 2H); 3.62 (s, 2H, ethyl ester); 3.58 (s, 1H, methyl ester); 3.45–3.25 (m, 3H); 3.20–3.00 (m, 3H); 2.89–2.80 (m, 1H); 2.81–2.68 (m, 2H); 1.55–1.40 (m, 11H); 1.35–1.15 (m, 11H, includes ethyl ester signal); 0.86 (t, 3H).

MS: m/z 428.2 (M−Boc+1; methyl ester); 442.2 (M−Boc+1; ethyl ester)

EXAMPLE 52

3-{4-[2-(tert-Butoxycarbonyl-heptyl-amino)-ethyl]-phenyl}-2-ethylsulfanyl-propionic acid ethyl ester:

Synthesized from 3-{4-[2-(tert-butoxycarbonyl-heptyl-amino)-ethyl]-phenyl}-2-hydroxy-propionic acid ethyl ester using a procedure analogous to that used for Example 50 and substituting the sodium salt of ethanethiol as the nucleophile to give an approximate 1:1 mixture of ethyl and methyl ester as a clear film (23 mg, 43%).

$^1$H NMR δ($CDCl_3$): 7.15–7.00 (m, 4H); 4.17–4.05 (m, 2H, ethyl ester); 3.66 (s, 3H, methyl ester); 3.54–3.45 (m, 1H); 3.40–3.25 (m, 2H); 3.20–2.98 (m, 3H); 2.95–2.87 (m, 1H); 2.82–2.70 (m, 2H); 2.67–2.55 (m, 2H); 1.55–1.37 (m, 11H); 1.34–1.14 (m, 14H, includes ethyl ester signal); 0.86 (t, 3H)

MS: m/z 366.2 (M−Boc+1, methyl ester); 380.2 (M−Boc+1, ethyl ester)

EXAMPLE 53

3-{4-[2-(tert-Butoxycarbonyl-heptyl-amino)-ethyl]-phenyl}-2-phenoxy-propionic acid ethyl ester:

Synthesized from 3-{4-[2-(tert-butoxycarbonyl-heptyl-amino)-ethyl]-phenyl}-2-hydroxy-propionic acid ethyl ester using a procedure analogous to that used for Example 50 and substituting phenol as the nucleophile to give an approximate 1:1 mixture of ethyl and methyl ester as a clear film (35 mg, 61%).

$^1$H NMR δ($CDCl_3$): 7.32–7.17 (m, 3H); 7.17–7.04 (m, 2H); 7.01–6.77 (m, 4H); 4.88–4.71 (m, 2H, ethyl ester); 4.26–4.09 (m, 1H); 3.80–3.66 (m, 3H, methyl ester); 3.45–3.27 (m, 2H); 3.27–3.00 (m, 4H); 2.90–2.67 (m, 2H); 1.57–1.37 (m, 11H); 1.37–1.10 (m, 12H, includes ethyl ester signal); 0.97–0.79 (m, 3H).

MS: m/z 398.2 (M−Boc+1, methyl ester); 412.2 (M−Boc+1, ethyl ester)

EXAMPLE 54

3-{4-[2-(tert-Butoxycarbonyl-heptyl-amino)-ethyl]-phenyl}-2-phenylsulfanyl-propionic acid ethyl ester:

Synthesized from 3-{4-[2-(tert-butoxycarbonyl-heptyl-amino)-ethyl]-phenyl}-2-hydroxy-propionic acid ethyl ester using a procedure analogous to that used for Example 50 and substituting benzenethiol as the nucleophile to give an approximate 1:1 mixture of ethyl and methyl ester as a clear film (51 mg, 87%).

$^1$H NMR δ($CDCl_3$): 7.50–7.38 (m, 2H); 7.32–7.25 (m, 3H); 7.17–7.01 (m, 4H); 4.07–3.95 (m, 2H, ethyl ester); 3.91–3.82 (m, 1H); 3.56 (s, 3H, methyl ester); 3.41–3.24 (m, 2H); 3.23–2.97 (m, 4H); 2.83–2.68 (m, 2H); 1.52–1.37 (m, 11H); 1.34–1.15 (m, 8H); 1.06 (t, 3 H, ethyl ester signal); 0.86 (t, 3H)

MS: m/z 414.1 (M−Boc+1, methyl ester); 428.1 (M−Boc+1, ethyl ester) 47723-84-1 through 12

EXAMPLE 55

2-Benzyloxy-3-(4-{2-[1-heptyl-3-(4-isopropyl-phenyl)-ureido]-ethyl}-phenyl-propionic acid ethyl ester:

Synthesized from 2-benzyloxy-3-{4-[2-(tert-butoxycarbonyl-heptyl-amino)-ethyl]-phenyl}-propionic acid ethyl ester using procedures analogous to that used for Example 8 immediately followed by Example 10 and substituting 1-isocyanato-4-isopropyl-benzene in the place of 2,4-dimethoxyphenylisocyanate to give crude 2-benzyloxy-3-(4-{2-[1-heptyl-3-(4-isopropyl-phenyl)-ureido]-ethyl}-phenyl)-propionic acid ethyl ester.

MS: m/z 587.2 (M+1)

EXAMPLE 56

3-(4-{2-]1-Heptyl-3-(4-isopropyl-phenyl)-ureido]-ethyl}-phenyl)-2-methoxy-propionic acid ethyl ester:

Synthesized from 3-{4-[2-(tert-butoxycarbonyl-heptyl-amino)-ethyl]-phenyl}-2-methoxy-propionic acid methyl ester using procedures analogous to that used for Example 8 immediately followed by Example 10 and substituting 1-isocyanato4-isopropyl-benzene in the place of 2,4-dimethoxyphenylisocyanate to give 3-(4-{2-[1-heptyl-3-(4-isopropyl-phenyl)-ureido]-ethyl}-phenyl)-2-methoxy-propionic acid ethyl ester.

MS: m/z 511.2 (M+1; ethyl ester); 497.2 (M+1, methyl ester)

EXAMPLE 57

2-Allyloxy-3-(4-{2-[1-heptyl-3-(4-isopropyl-phenyl)-ureido]-ethyl}-phenyl)-propionic acid ethyl ester:

Synthesized from 3-{4-[2-(tert-butoxycarbonyl-heptyl-amino)-ethyl]-phenyl}-2-allyloxy-propionic acid methyl

EXAMPLE 58

3-(4-{2-[1-Heptyl-3-(4-isopropyl-phenyl)-ureido]-ethyl}-phenyl)-2-phenoxy-propionic acid ethyl ester:

Synthesized from 3-{4-[2-(tert-butoxycarbonyl-heptyl-amino)-ethyl]-phenyl}-2-phenoxy-propionic acid methyl ester using procedures analogous to that used for Example 8 immediately followed by Example 10 and substituting 1-isocyanato-4-isopropyl-benzene in the place of 2,4-dimethoxyphenylisocyanate to give the title compound.

MS: m/z 573.2 (M+1, ethyl ester); 559.2 (methyl ester)

EXAMPLE 59

3-(4-{2-[1-Heptyl-3-(4-isopropyl-phenyl)-ureido]-ethyl}-phenyl)-2-isopropylsulfanyl-propionic acid ethyl ester:

Synthesized using procedures analogous to that used for Example 8 immediately followed by Example 10 and substituting 1-isocyanato4-isopropyl-benzene in the place of 2,4-dimethoxyphenylisocyanate to give the title compound.

MS: m/z 555.2 (M+1, ethyl ester); 541.2 (M+1, methyl ester)

EXAMPLE 60

2-Benzylsulfanyl-3-(4-{2-[1-heptyl-3-(4-isopropyl-phenyl)-ureido]-ethyl}-phenyl)-propionic acid ethyl ester:

Synthesized using procedures analogous to that used for Example 8 immediately followed by Example 10 and substituting 1-isocyanato-4-isopropyl-benzene in the place of 2,4-dimethoxyphenylisocyanate to give the title compound.

MS: m/z 603.2 (M+1, ethyl ester); 589.2 (M+1, methyl ester)

EXAMPLE 61

2-Ethylsulfanyl-3-(4-{2-[1-heptyl-3-(4-isopropyl-phenyl)-ureido]-ethyl}-phenyl)-propionic acid ethyl ester:

Synthesized using procedures analogous to that used for Example 8 immediately followed by Example 10 and substituting 1-isocyanato-4-isopropyl-benzene in the place of 2,4-dimethoxyphenylisocyanate to give the title compound.

MS: m/z 541.2 (M+1, ethyl ester); 527.2 (M+1, methyl ester)

EXAMPLE 62

3-(4-{2-[11 -Heptyl-3-(4-isopropyl-phenyl)-ureido]-ethyl}-phenyl)-2-phenylsulfanyl-propionic acid ethyl ester:

Synthesized using procedures analogous to that used for Example 8 immediately followed by Example 10 and substituting 1-isocyanato-4-isopropyl-benzene in the place of 2,4-dimethoxyphenylisocyanate to give the title compound.

MS: m/z 589.2 (M+1, ethyl ester); 575.2 (M+1, methyl ester)

EXAMPLE 63

2-Benzyloxy-3-(4-{2-[3-(2,4-difluoro-phenyl)-1-heptyl-ureido]-ethyl}-phenyl)-propionic acid ethyl ester:

Synthesized using procedures analogous to that used for Example 8 immediately followed by Example 10 and substituting 2,4-difluorophenylisocyanate in the place of 2,4-dimethoxyphenylisocyanate to give the title compound.

MS: m/z 581.3(M+1)

EXAMPLE 64

2-Benzyloxy-3-(4-{2-[3-(2,4-dimethoxy-phenyl)-1-heptyl-ureido]-ethyl}-phenyl)-propionic acid ethyl ester:

Synthesized using procedures analogous to that used for Example 8 immediately followed by Example 10 to give the title compound.

MS: m/z 531.5 (M+1)

EXAMPLE 65

2-Allyoxy-3-(4-{2-[3-(2,4-difluoro-phenyl)-1-heptyl-ureido]-ethyl}-phenyl)-propionic acid ethyl ester:

Synthesized using a procedure analogous to that used for Example 8 immediately followed by Example 10 and substituting 2,4-difluorophenylisocyanate in the place of 2,4-dimethoxyphenylisocyanate to give the title compound.

MS: m/z 505.5 (M+1)

Examples 66–76 were prepared according to procedures analogous to those of Example 18.

EXAMPLE 66

2-Benzyloxy-3-(4-{2-[1-heptyl-3-(4-isopropyl-phenyl)-ureido]-ethyl}-phenyl)-propionic acid:

$^1$H NMR δ(CDCl$_3$):7.38–7.26 (m, 3H); 7.22–7.04 (m, 1OH); 4.59 (d, 1H); 4.39 (d, 1H); 4.17 (dd, 1H); 3.50 (t, 2H); 3.25–3.09 (m, 3H); 3.06–2.97 (m, 1H); 2.89 (t, 2H); 2.85–2.77 (m, 1H); 1.60 (quint, 2H); 1.35–1.20 (m, 8H); 1.20(s, 3H); 1.18 (s, 3H); 0.87 (t, 3H).

MS: m/z 557.1 (M−1)

EXAMPLE 67

3-(4-{2-[1-Heptyl-3-(4-isopropyl-phenyl)-ureido]-ethyl}-phenyl)-2-methoxy-propionic acid:

$^1$H NMR δ(CDCl$_3$): 7.23–7.03 (m, 8H); 6.04 (s, 1H); 3.95 (dd, 1H); 3.50 (t, 2H); 3.33 (s, 3H); 3.20 (t, 2H); 3.08 (dd, 1H); 2.97 (dd, 1H); 2.91–2.72 (m, 3H); 1.59 (quint, 2H); 1.35–1.20 (m, 8H); 1.19 (s, 3H); 1.18 (s, 3H); 0.87 (t, 3H)

MS: m/z 481.1 (M−1)

EXAMPLE 68

2-Allyloxy-3-(4-{2-[1-heptyl-3-(4-isopropyl-phenyl)-ureido]-ethyl}-phenyl-propionic acid:

$^1$H NMR δ(CDCl$_3$): 7.24–7.05 (m, 8H); 5.98 (s, 1H); 5.80–5.68 (m, 1H); 5.22–5.10 (m, 2H); 4.10 (dd, 1H); 4.07–4.02 (m, 1H); 3.90–3.84 (m, 1H); 3.50 (t, 2H); 3.20 (t, 2H); 3.08 (dd, 1H); 2.98 (dd, 1H); 2.92–2.75 (m, 3H); 1.59 (quint, 2H); 1.35–1.20 (m, 8H); 1.18 (s, 3H); 0.87 (t, 3H).

MS: m/z 507.1 (M−1)

EXAMPLE 69

3-(4-{2-[1-Heptyl-3-(4-isopropyl-phenyl)-ureido]-ethyl}-phenyl)-2-phenoxy-propionic acid:

$^1$H NMR δ(CDCl$_3$): 7.30–7.04 (m, 11H); 6.95 (t, 1H); 6.83 (d, 1H); 6.06 (s, 1H); 4.80 (t, 1H); 3.48 (t, 2H); 3.22 (d, 2H); 3.17 (t, 2H); 2.90–2.75 (m, 3H); 1.57 (quint, 2H); 1.35–1.20 (m, 8H); 1.19 (s, 3H); 1.17 (s, 3H); 0.87 (t, 3H).

MS: m/z 543.1 (M−1)

EXAMPLE 70

3-(4-{2-[1-heptyl-3-(4-isopropyl-phenyl)-ureido]-ethyl}-phenyl)-2-isopropylsulfanyl-propionic acid:

$^1$H NMR δ(CDCl$_3$):7.23–7.05 (m, 8H); 6.26 (s, 1H); 3.53 (dd, 1H); 3.48 (t, 2H); 3.23–3.11 (m, 3H); 3.05 (septet, 1H); 2.92 (dd, 1H); 2.88–2.75 (m, 3H); 1.59 (quint, 2H); 1.35–1.15 (m, 20H); 0.87 (t, 3H).

MS: m/z 525.1 (M−1)

EXAMPLE 71
2-Benzylsulfanyl-3-(4-{2-[1-heptyl-3-(4-isopropyl-phenyl)-ureido]-ethyl}-phenyl)-propionic acid:

$^1$H NMR δ(CDCl$_3$): 7.30–6.98 (m, 13H); 6.21 (s, 1H); 3.84 (d, 1H); 3.77 (d, 1H); 3.47 (t, 2H); 3.38 (dd, 1H); 3.19 (t, 2H); 3.16–3.09 (m, 1H); 2.90–2.80 (m, 4H); 1.59 (quint, 2H); 1.34–1.21 (m, 8H); 1.20 (s, 3H); 1.18 (s, 3H); 0.87 (t, 3H).

MS: m/z 573.1 (M−1)

EXAMPLE 72
2-Ethylsulfanyl-3-(4-{2-[1-heptyl-3-(4-isopropyl-phenyl)-ureido]-ethyl}-phenyl)-propionic acid:

$^1$H NMR δ(CDCl$_3$):7.207.05 (m, 8H); 6.27 (s, 1H); 3.55–3.45 (m, 3H); 3.24–3.11 (m, 3H); 2.92 (dd, 1H); 2.89–2.77 (m, 3H); 2.70–2.60 (m, 2H); 1.59 (quint, 2H); 1.33–1.21 (m, 11H); 1.20 (s, 3H); 1.18 (s, 3H); 0.86 (t, 3H).

MS: m/z 511.1 (M−1)

EXAMPLE 73
3-(4-{2-[1-Heptyl-3-(4-isopropyl-phenyl)-ureido]-ethyl}-phenyl)-2-phenylsulfanyl-propionic acid:

$^1$H NMR δ(CDCl$_3$): 7.44–7.38 (m, 2H); 7.29–7.24 (m, 3H); 7.19–7.06 (m, 8H); 6.11 (s, 1H); 3.83 (dd, 1H); 3.46 (t, 2H); 3.20–3.09 (m, 3H); 3.01 (dd, 1H); 2.89–2.76 (m, 3H); 1.56 (quint, 2H); 1.34–1.20 (m, 8H); 1.19 (s, 3H); 1.17 (s, 3H); 0.86 (t, 3H).

MS: m/z 559.1 (M−1)

EXAMPLE 74
2-Benzyloxy-3-(4-{2-[3-(2,4-difluoro-phenyl)-1-heptyl-ureido]-ethyl}-phenyl)-propionic acid:

$^1$H NMR δ(CDCl$_3$): 8.10–7.95 (m, 1H); 7.32–7.26 (m, 3H); 7.22–7.12 (m, 6H); 6.89–6.76 (m, 2H); 6.32 (d, 1H); 4.60 (d, 1H); 4.41 (d, 1H); 4.16 (dd, 1H); 3.51 (t, 2H); 3.21 (t, 2H); 3.13 (dd, 1H); 3.01 (dd, 1H); 2.89 (t, 2H); 1.59 (quint, 2H); 1.38–1.20 (m, 8H); 0.87 (t, 3H) MS: m/z 551.1 (M−1)

EXAMPLE 75
2-Benzyloxy-3-(4-{2-[3-(2,4-dimethoxy-phenyl)-1-heptyl-ureido]-ethyl}-phenyl)-propionic acid:

$^1$H NMR δ(CDCl$_3$): 8.05–7.95 (m, 1H); 7.19 (d, 2H); 7.15 (d, 2H); 6.85–6.75 (m, 2H); 6.32 (d, 1H); 5.80–5.70 (m, 1H); 5.23–5.13 (m, 2H); 4.11 (dd, 1H); 4.08–4.00 (m, 1H); 3.96–3.88 (m, 1H); 3.50 (t, 2H); 3.20 (t, 2H); 3.10 (dd, 1H); 2.98 (dd, 1H); 2.88 (t, 2H); 1.59 (quint, 2H); 1.35–1.20 (m, 8H); 0.87 (t, 3H).

MS: m/z 501.1 (M−1)

EXAMPLE 76
2-Allyloxy-3-(4-{2-[3-(2,4-difluoro-phenyl)-1-heptyl-ureido]-ethyl}-phenyl)-propionic acid:

$^1$H NMR δ(CDCl$_3$):8.04–7.98 (m, 1H); 7.29–7.23 (m, 3H; 7.20–7.12 (m, 5H); 7.29–7.23 (m, 3H); 7.20–7.13 (m, 5H); 6.87 (s, 1H); 6.50–6.44 (m, 2H); 4.63 (d, 1H); 4.39 (d, 1H); 4.14 (dd, 1H); 3.83 (s, 3H); 3.77 (s, 3H); 3.49 (t, 2H); 3.22 (t, 2H); 3.12 (dd, 1H); 3.00 (dd, 1H); 2.90 (t, 2H); 1.60 (quint, 2H); 1.35–1.20 (m, 8H); 0.86 (t, 3H).

MS: m/z 575.1 (M−1)

EXAMPLE 77
2-(4-{2-[3-(2,4-Difluoro-phenyl)-1-heptyl-ureido]-ethyl}-phenylamino)-2-methyl-propionic acid:

1-(3-Dimethylaminopropyl)-3-ethylcarbodiimide hydrochloride (3.86 g, 20.1 mmol) and heptanoic acid (2.38 mL, 16.8 mmol) were added sequentially to a solution of 4-nitrophenethylamine (3.40 g, 16.8 mmol), triethylamine (2.81 mL, 20.1 mmol) and methylene chloride (25 mL). After stirring 18 h at ambient temperature, the reaction mixture was diluted with ethyl acetate; washed sequentially with water, 1N aqueous hydrochloric acid, water, saturated aqueous sodium bicarbonate and saturated aqueous sodium chloride; dried over anhydrous sodium sulfate; filtered and concentrated under reduced pressure to provide 3.80 g (81%) of heptanoic acid [2-(4-nitro-phenyl)-ethyl]-amide as an off-white solid.

MS (APCI): 279 (M+H)$^+$.

$^1$H NMR (400 MHz, CDCl$_3$) δ8.16 (d, 2H), 7.35 (d, 2H), 5.43 (s, 1H), 3.54 (m, 2H), 2.93 (t, 2H), 2.12 (t, 2H), 1.57 (m, 3H), 1.26 (m, 5H), 0.86 (t, 3H). 10% Palladium on carbon (380 mg, 10 wt %) was added to a solution of heptanoic acid [2-(4-nitro-phenyl)-ethyl]-amide (3.80 g, 13.6 mmol) and methanol (80 mL) in a Parr bottle and the resulting mixture hydrogenated at 55 psi for 4 h. The reaction mixture was filtered through a plug of Celite and the Celite plug washed thoroughly with ethyl acetate. The combined filtrates were concentrated under reduced pressure to provide 3.24 g (96%) of heptanoic acid [2-(4-amino-phenyl)-ethyl]-amide as an off-white solid.

MS (APCI): 249 (M+H)$^+$.

$^1$H NMR (400 MHz, CDCl$_3$) δ6.94 (d, 2H), 6.61 (d, 2H), 5.35 (s, 1H), 3.57 (s, 2H), 3.43 (m, 2H), 2.66 (t, 3H), 2.07 (t, 2H), 1.55 (m, 3H), 1.24 (m, 5H), 0.84 (t, 3H). A mixture of heptanoic acid [2-(4-amino-phenyl)-ethyl]-amide (1.50 g, 6.04 mmol), cesium carbonate (7.87 g, 24.2 mmol), tert butyl-2-bromoisobutyrate (10.78 g, 48.3 mmol) and dimethylformamide (14.6 mL) was heated at 80° C. for 4 days. The reaction mixture was cooled to ambient temperature, diluted with water and extracted with ether (2×). The combined organics were washed with water and saturated aqueous sodium chloride, dried over anhydrous sodium sulfate, filtered, concentrated under reduced pressure and purified by flash column chromatography (2:3 ethyl acetate/hexanes) to provide 1.37 g (58%) of 2-[4-(2-heptanoylamino-ethyl)-phenylamino]-2-methyl-propionic acid tert-butyl ester as a colorless oil.

MS (APCI): 391 (M+H)$^+$.

$^1$H NMR (400 MHz, CDCl$_3$) δ6.98 (d, 2H), 6.59 (d, 2H), 5.38 (s, 1H), 4.03 (s, 1H), 3.47 (m, 2H), 2.70 (t, 2H), 2.11 (t, 2H), 1.65–1.40 (m, 3H), 1.53 (s, 6H), 1.39 (s, 9H), 1.29 (m, 5H), 0.89 (t, 3H). Borane-tetrahydrofuran complex (1.0M in THF; 6.96 mL, 6.96 mmol) was added to a solution of 2-[4-(2-heptanoylamino-ethyl)-phenylamino]-2-methyl-propionic acid tert-butyl ester (1.36 g, 3.48 mmol) and tetrahydrofuran (25 mL) and the resulting mixture stirred at ambient temperature for 18 h. Additional borane-tetrahydrofuran complex (3.5 mL, 3.5 mmol) was added and the resulting mixture stirred 24 h at ambient temperature before acidifying with 1N aqueous hydrochloric acid. The resulting mixture was then refluxed for 2 h, cooled to ambient temperature and the tetrahydrofuran removed under reduced pressure. The resulting residue was neutralized with saturated aqueous sodium bicarbonate, concentrated under reduced pressure, azeotroped with ethyl acetate and purified by flash column chromatography (10% methanol/1% concentrated ammonium hydroxide/chloroform→15% methanol/1% concentrated ammonium hydroxide/chloroform) to provide 417 mg (38%) of 2-[4-(2-heptylamino-ethyl)-phenylamino]-2-methyl-propionic acid as a white solid.

MS (APCI): 321 (M+H)$^+$.

A solution of of 2-[4-(2-heptylamino-ethyl)-phenylamino]-2-methyl-propionic acid (75 mg, 234 μmol), 2,4-difluorophenyl isocyanate (33 μL, 281 μmol), N,N- diisopropylethylamine (82 μL, 468 μmol) and methylene chloride (0.5 mL) was stirred at ambient temperature for 18 h, concentrated under reduced pressure and purified by flash column chromatography (3% methanol/chloroform) to provide 8.6 mg (8%) of 2-(4-{2-[3-(2,4-difluoro-phenyl)-1-heptyl-ureido]-ethyl}-phenylamino)-2-methyl-propionic acid as a white foam.

MS (APCI): 476 (M+H)$^+$.

$^1$H NMR (400 MHz, CDCl$_3$) δ7.99 (m, 1H), 7.10 (d, 2H), 6.86 (m, 2H), 6.46 (m, 2H), 6.27 (s, 1H), 3.50 (t, 2H), 3.26 (t, 2H), 2.85 (t, 2H), 2.00–1.25 (m, 18H), 0.90 (t, 3H).

What is claimed is:

1. A compound of the Formula I:

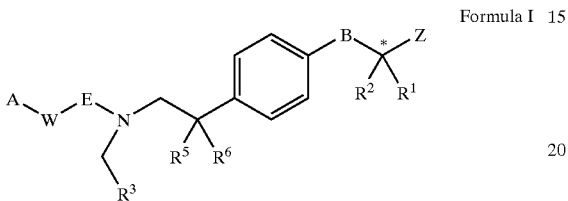

Formula I a prodrug thereof, or a pharmaceutically acceptable salt of said compound or of said prodrug;
wherein E is carbonyl or sulfonyl;

B is methylene;

Z is carboxyl, carboxaldehyde, hydroxymethyl, $(C_1-C_4)$ alkoxycarbonyl, cyano, hydroxyaminocarbonyl, tetrazolyl, tetrazolylaminocarbonyl, 4,5-dihydro-5-oxo-1,2,4-oxadiazol-3-yl, 3-oxoisoxazolidin-4-yl-aminocarbonyl, or —C(O)N(H)SO$_2$R$^4$;
  where R$^4$ is $(C_1-C_6)$alkyl, amino or mono-N— or di-N,N—$(C_1-C_6)$alkylamino, said $(C_1-C_6)$alkyl substituents are optionally substituted independently with from one to nine fluorines;

W is a bond, —N(H)—, —N(($C_1-C_4$)alkyl)-($C_1-C_4$alkylamino, or ($C_1-C_8$)alkylene;
  wherein said $(C_1-C_8)$alkylene may optionally be mono- or di-substituted independently with oxo, halo, $(C_1-C_6)$alkoxycarbonyl, $(C_1-C_6)$alkyl, $(C_2-C_6)$alkenyl, $(C_3-C_7)$cycloalkyl, hydroxy, $(C_1-C_6)$alkoxy, $(C_1-C_4)$alkylthio, amino, cyano, nitro, or mono-N— or di-N,N—$(C_1-C_6)$alkylamino or
  wherein W is CR$^7$R$^8$ wherein R$^7$ and R$^8$ are linked together to form a three to six membered fully saturated carbocyclic ring;

R$^1$ is H, $(C_1-C_6)$alkyl or $(C_3-C_6)$cycloalkyl;

R$^2$ is, a $(C_3-C_6)$cycloalkyl or a fully saturated, partially unsaturated or fully unsaturated one to four membered straight or branched carbon chain wherein one or two carbon(s) are replaced with oxygen or sulfur and wherein said carbon(s) is optionally mono-, di- or tri-substituted independently with halo, said carbon(s) is optionally mono-substituted with hydroxy, said carbon(s) is optionally mono-substituted with oxo, said sulfur is optionally mono- or di-substituted with oxo, and said chain is optionally mono-substituted with Y;
  wherein Y is a partially saturated, fully saturated or fully unsaturated three to eight membered ring optionally having one to four heteroatoms selected independently from oxygen, sulfur and nitrogen or a bicyclic ring consisting of two fused partially saturated, fully saturated or fully unsaturated three to six membered rings, taken independently, said bicyclic ring optionally having one to four heteroatoms selected independently from oxygen, sulfur and nitrogen;
  wherein said Y ring is optionally mono-, di- or tri-substituted independently with halo, $(C_2-C_6)$ alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; or R$^1$ and R$^2$ are linked together to form a three to six membered fully saturated carbocyclic ring optionally having one heteroatom selected from oxygen, sulfur and nitrogen;

R$^3$ is $(C_1-C_{10})$alkyl, $(C_2-C_{10})$alkenyl or $(C_2-C_{10})$alkynyl, said $(C_1-C_{10})$alkyl, $(C_2-C_{10})$alkenyl or $(C_2-C_{10})$ alkynyl substituents are optionally mono-, di- or tri-substituted independently with halo, hydroxy, $(C_1-C_6)$ alkoxy, $(C_1-C_4)$alkylthio, amino, nitro, cyano, oxo, carboxy, $(C_1-C_6)$alkyloxycarbonyl, or mono-N— or di-N,N—$(C_1-C_6)$alkylamino or optionally
  said $(C_1-C_{10})$alkyl, $(C_2-C_{10})$alkenyl or $(C_2-C_{10})$ alkynyl substituents are mono-substituted with a partially saturated, fully saturated or fully unsaturated five to six membered ring optionally having one to two heteroatoms selected from nitrogen, oxygen and sulfur, or a bicyclic ring consisting of two fused partially saturated, fully saturated or fully unsaturated three to six membered rings, taken independently, said bicyclic ring optionally having one to four heteroatoms selected independently from oxygen, sulfur and nitrogen;
  said ring optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$ alkyloxycarbonyl, mono-N— or di-N,N—$(C_1-C_6)$ alkylamino wherein said $(C_1-C_6)$alkyl substituent is optionally mono-, di- or tri-substituted independently with halo, hydroxy, $(C_1-C_6)$alkoxy, $(C_1-C_4)$ alkylthio, amino, nitro, cyano, oxo, carboxy, $(C_1-C_6)$ alkyloxycarbonyl, mono-N— or di-N,N—$(C_1-C_6)$ alkylamino, said $(C_1-C_6)$alkyl substituent is also optionally substituted with from one to nine fluorines;

R$^5$ and R$^6$ are linked together to form a three to six membered fully saturated carbocyclic ring or are each independently H, $(C_1-C_6)$alkyl, $(C_3-C_7)$cycloalkyl or $(C_3-C_7)$cycloalkyl$(C_1-C_6)$alkyl; and A is H, mono-N— or di-N,N—$(C_1-C_6)$alkylamino, $(C_2-C_6)$alkanoylamino, $(C_1-C_6)$alkoxy, or a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, said bicyclic ring optionally having one to four heteroatoms selected independently from oxygen, sulfur and nitrogen; and wherein said A ring is optionally mono-, di- or tri-substituted independently with oxo, carboxy, halo, $(C_1-C_6)$alkoxycarbonyl, $(C_1-C_6)$alkyl, $(C_2-C_6)$alkenyl, $(C_3-C_7)$cycloalkyl, $(C_3-C_7)$cycloalkyl $(C_1-C_6)$alkyl, hydroxy, $(C_1-C_6)$alkoxy, $(C_1-C_4)$ alkylthio, amino, cyano, nitro, or mono-N— or di-N,N—$(C_1-C_6)$alkylamino wherein said $(C_1-C_6)$alkyl or $(C_1-C_6)$alkoxy substituents are optionally mono-, di- or tri-substituted independently with halo, hydroxy, $(C_1-C_6)$alkoxy, amino, mono-N— or di-N, N—$(C_1-C_6)$alkylamino or from one to nine fluorines, or wherein said A ring is optionally mono-substituted with a partially saturated, fully saturated or fully unsaturated three to eight membered ring optionally having one to four heteroatoms selected independently from oxygen, sulfur and nitrogen.

2. A compound as recited in claim 1 wherein

E is C(O);

B is methylene;

Z is carboxy;

W is a bond, $(C_1-C_4)$alkylene, or —N(H)—;

$R^1$ is H or $(C_1-C_4$alkyl;

$R^2$ is $(C_1-C_4)$alkoxy;

$R^3$ is $(C_4-C_8)$alkyl;

$R^5$ and $R^6$ are each H; and

A is a five to six membered partially saturated, fully saturated or fully unsaturated ring optionally having one heteroatom selected from oxygen, sulfur and nitrogen, or a bicyclic ring consisting of two fused partially saturated, fully saturated or fully unsaturated five to six membered ring, taken independently, optionally having one to four heteroatoms selected independently from oxygen, sulfur and nitrogen;

wherein said A substituent is optionally mono-, di- or tri-substituted independently with halo, $(C_1-C_6)$ alkyl, hydroxy, $(C_1-C_6)$alkoxy, $(C_1-C_4)$alkylthio, amino, nitro, cyano or mono-N— or di-N,N—$(C_1-C_6)$alkylamino, said $(C_1-C_6)$alkyl or $(C_1-C_6)$ alkoxy substituents are optionally substituted independently with from one to nine fluorines or a pharmaceutically acceptable salt thereof.

3. A compound as recited in claim 2 wherein

A is phenyl, wherein said phenyl substituent is optionally mono-, di- or tri-substituted independently with halo, $(C_1-C_6)$ alkyl, hydroxy, $(C_1-C_6)$alkoxy, $(C_1-C_4)$ alkylthio, amino, nitro, cyano or mono-N— or di-N, N—$(C_1-C_6)$alkylamino, said $(C_1-C_6)$alkyl or $(C_1-C_6)$ alkoxy substituents are optionally substituted independently with from one to nine fluorines or a pharmaceutically acceptable salt thereof.

4. A compound as recited in claim 3 wherein

W is N(H)—;

said A phenyl substituent is optionally mono- or di-substituted independently with fluoro, trifluoromethyl, trifluoromethoxy, chloro, $(C_1-C_4)$ alkyl, hydroxy, cyano, $(C_1-C_2)$alkoxy, amino or mono-N— or di-N,N—$(C_1-C_2)$alkylamino; and $R^3$ is $(C_6-C_8)$alkyl or the pharmaceutically salts thereof.

5. A compound as recited in claim 1 wherein said compound is (R)-3-(4-{2-[3-(2,4-dimethoxy-phenyl)-1-heptyl-ureido]-ethyl}-phenyl)-2-ethoxy-propionic acid;

(S)-3-(4-{2-[3-(2,4-dimethoxy-phenyl)-1-heptyl-ureido]-ethyl}-phenyl)-2-ethoxy-propionic acid;

(R)-2-ethoxy-3-(4-{2-[1-heptyl-3-(4-isopropyl-phenyl)-ureido]-ethyl}-phenyl)-propionic acid;

(S)-2-ethoxy-3-(4-{2-[1-heptyl-3-(4-isopropyl-phenyl)-ureido]-ethyl}-phenyl)-propionic acid;

(R)-3-(4-{2-[3-(2,3-dichloro-phenyl)-1-heptyl-ureido]-ethyl}-phenyl)-2-ethoxy-propionic acid;

(S)-3-(4-{2-[3-(2,3-dichloro-phenyl)-1-heptyl-ureido]-ethyl}-phenyl)-2-ethoxy-propionic acid;

(R)-2-ethoxy-3-(4-{2-[1-heptyl-3-(4-trifluoromethoxy-phenyl)-ureido]-ethyl}-phenyl)-propionic acid;

(S)-2-ethoxy-3-(4-{2-[1-heptyl-3-(4-trifluoromethoxy-phenyl)-ureido]-ethyl}-phenyl)-propionic acid;

(R)-3-(4-{2-[3-(2,4-dimethyl-phenyl)-1-heptyl-ureido]-ethyl}-phenyl)-2-ethoxy-propionic acid;

(S)-3-(4-{2-[3-(2,4-dimethyl-phenyl)-1-heptyl-ureido]-ethyl}-phenyl)-2-ethoxy-propionic acid;

(R)-3-(4-{2-[3-(4-tert-butyl-phenyl)-1-heptyl-ureido]-ethyl}-phenyl)-2-ethoxy-propionic acid;

(S)-3-(4-{2-[3-(4-tert-butyl-phenyl)-1-heptyl-ureido]-ethyl}-phenyl)-2-ethoxy-propionic acid;

or the pharmaceutically acceptable salts of said compounds.

6. A compound as recited in claim 4 wherein said compound is a. $R^1$ is hydrogen;
   $R^2$ is ethoxy;
   $R^3$ is hexyl; and
   A is 2,4-dimethoxyphenyl; or b. $R^1$ is hydrogen;
   $R^2$ is ethoxy;
   $R^3$ is hexyl; and
   A is 4-isopropylphenyl; or c. $R^1$ is hydrogen;
   $R^2$ is ethoxy;
   $R^3$ is hexyl; and
   A is 2,3-dichlorophenyl; or d. $R^1$ is hydrogen;
   $R^2$ is ethoxy;
   $R^3$ is hexyl; and
   A is 4-trifluoromethoxyphenyl; or e. $R^1$ is hydrogen;
   $R^2$ is ethoxy;
   $R^3$ is hexyl; and
   A is 2,4-dimethylphenyl; or f. $R^1$ is hydrogen;
   $R^2$ is ethoxy;
   $R^3$ is hexyl; and
   A is 4-tertbutylphenyl or the pharmaceutically acceptable salts of said compounds.

7. A compound as recited in claim 3 wherein

W is methylene;

said A phenyl substituent is optionally mono- or di-substituted independently with fluoro, trifluoromethyl, trifluoromethoxy chloro, $(C_1-C_3)$ alkyl, hydroxy, $(C_1-C_2)$alkoxy, amino or mono-N— or di-N,N—$(C_1-C_2)$alkylamino; and $R^3$ is $(C_4-C_8)$alkyl or a pharmaceutically acceptable salt thereof.

8. A compound as recited in claim 1 wherein said compound is (R)-3-[4-(2-{[(2,4-difluoro-phenyl)-acetyl]-heptyl-amino}-ethyl)phenyl]-2-ethoxy-propionic acid;

(S)-3-[4-(2-{[(2,4-difluoro-phenyl)-acetyl]-heptyl-amino}-ethyl)-phenyl]-2-ethoxy-propionic acid;

(R)-2-ethoxy-3-{4-[2-(heptyl-p-tolylacetyl-amino)-ethyl]-phenyl}-propionic acid;

(S)-2-ethoxy-3-{4-[2-(heptyl-p-tolylacetyl-amino)-ethyl]-phenyl}-propionic acid;

or the pharmaceutically acceptable salts of said compounds.

9. A compound as recited in claim 7 wherein
   a. $R^1$ is hydrogen;
      $R^2$ is ethoxy;
      $R^3$ is hexyl; and
      A is 2,4-difluorophenyl; or
   b. $R^1$ is hydrogen;
      $R^2$ is ethoxy;
      $R^3$ is hexyl; and
      A is 4-methylphenyl
or the pharmaceutically acceptable salts of said compounds.

10. A compound as recited in claim 1 wherein
    E is C(O);
    Z is carboxy;
    W is a bond, $(C_1-C_4)$alkylene or —N(H)—;
    $R^1$ is H, $(C_1-C_4)$alkyl or $(C_3-C_6)$cycloalkyl;
    $R^2$ is $(C_1-C_4)$alkoxy, $(C_1-C_4)$alkylthio, phenoxy, benzyloxy, phenylthio, benzylthio, or $(C_3-C_6)$cycloalkyl, said phenyl moieties optionally mono- or di-substituted independently with cyano, fluoro, trifluoromethyl, trifluoromethoxy, chloro, $(C_1-C_3)$alkyl, hydroxy, $(C_1-C_2)$alkoxy, amino or mono-N— or di-N,N—$(C_1-C_2)$alkylamino;
    $R^3$ is $(C_4-C_8)$alkyl;
    $R^5$ and $R^6$ are each H; and
    A is a five to six membered partially saturated, fully saturated or fully unsaturated ring optionally having one heteroatom selected from oxygen, sulfur and nitrogen, or a bicyclic ring consisting of two fused partially saturated, fully saturated or fully unsaturated five to six membered rings, taken independently, optionally having one to four heteroatoms selected independently from oxygen, sulfur and nitrogen;
    wherein said A substituent is optionally mono-, di- or tri-substituted independently with halo, $(C_1-C_6)$ alkyl, hydroxy, $(C_1-C_6)$alkoxy, $(C_1-C_4)$alkylthio, amino, nitro, cyano, or mono-N— or di-N,N—$(C_1-C_6)$alkylamino, said $(C_1-C_6)$alkyl or $(C_1-C_6)$ alkoxy substituents are optionally substituted independently with from one to nine fluorines or a pharmaceutically acceptable salt thereof.

11. A compound as recited in claim 10 wherein
    W is N(H)—;
    $R^2$ is $(C_1-C_4,$ alkoxy, phenoxy, benzyloxy, or $(C_3-C_6)$ cycloalkyl, said phenyl moieties optionally mono- or di-substituted independently with cyano, fluoro, trifluoromethyl, trifluoromethoxy, chloro, $(C_1-C_3)$alkyl, hydroxy, $(C_1-C_2)$alkoxy, amino or mono-N— or di-N,N—$(C_1-C_2)$alkylamino;
    $R^3$ is $(C_6-C_8)$alkyl;
    A is phenyl, wherein said phenyl substituent is optionally mono-, di- or tri-substituted independently with halo, $(C_1-C_6)$ alkyl, hydroxy, $(C_1-C_6)$alkoxy, $(C_1-C_4)$ alkylthio, amino, nitro, cyano or mono-N— or di-N,N—$(C_1-C_6)$alkylamino, said $(C_1-C_6)$alkyl or $(C_1-C_6)$ alkoxy substituents are optionally substituted independently with from one to nine fluorines or a pharmaceutically acceptable salt thereof.

12. A compound as recited in claim 11 wherein
    $R^1$ is H;
    said A phenyl substituent is optionally mono- or di-substituted independently with fluoro, trifluoromethyl, trifluoromethoxy, chloro, $(C_1-C_3)$ alkyl, hydroxy, $(C_1-C_2)$alkoxy, amino or mono-N— or di-N,N—$(C_1-C_2)$alkylamino;
or a pharmaceutically acceptable salt thereof.

13. A compound as recited in claim 1 wherein said compound is
    (R)-2-benzyloxy-3-(4-{2-[1-heptyl-3-(4-isopropyl-phenyl)-ureido]-ethyl}-phenyl)-propionic acid;
    (S)-2-benzyloxy-3-(4-{2-[1-heptyl-3-(4-isopropyl-phenyl)-ureido]-ethyl}-phenyl)-propionic acid;
    (R)-3-(4-{2-[1-heptyl-3-(4-isopropyl-phenyl)-ureido]-ethyl}-phenyl)-2-phenoxy-propionic acid;
    (S)-3-(4-{2-[1-heptyl-3-(4-isopropyl-phenyl)-ureido]-ethyl}-phenyl)-2-phenoxy-propionic acid;
    (R)-2-benzyloxy-3-(4-{2-[3-(2,4-dimethoxy-phenyl)-1-heptyl-ureido]-ethyl}-phenyl)-propionic acid;
    (S)-2-benzyloxy-3-(4-{2-[3-(2,4-dimethoxy-phenyl)-1-heptyl-ureido]-ethyl}-phenyl)-propionic acid;
or the pharmaceutically acceptable salts of said compounds.

14. A compound as recited in claim 12 wherein
    a. $R^2$ is benzyloxy;
       $R^3$ is hexyl; and
       A is 4-isopropylphenyl; or
    b. $R^2$ is phenoxy;
       $R^3$ is hexyl; and
       A is 4-isopropylphenyl; or
    c. $R^2$ is benzyloxy;
       $R^3$ is hexyl; and
       A is 2,4-methoxyphenyl;
or the pharmaceutically acceptable salts of said compounds.

15. A compound as recited in claim 10 wherein
    W is N(H)—;
    $R^2$ is, $(C_1-C_4)$alkylthio, phenylthio or phenylmethylthio, said phenyl moieties optionally mono- or di-substituted independently with cyano, fluoro, trifluoromethyl, trifluoromethoxy, chloro, $(C_1-C_3)$alkyl, hydroxy, $(C_1-C_2)$alkoxy, amino or mono-N— or di-N,N—$(C_1-C_2)$alkylamino;
    $R^3$ is $(C_6-C_8)$alkyl;
    $R^5$ and $R^6$ are each H; and
    A is phenyl, wherein said phenyl substituent is optionally mono-, di- or tri-substituted independently with halo, $(C_1-C_6)$ alkyl, hydroxy, $(C_1-C_6)$alkoxy, $(C_1-C_4)$ alkylthio, amino, nitro, cyano or mono-N— or di-N,N—$(C_1-C_6)$alkylamino, said $(C_1-C_6)$alkyl or $(C_1-C_6)$ alkoxy substituents are optionally substituted independently with from one to nine fluorines or a pharmaceutically acceptable salt thereof.

16. A compound as recited in claim 15 wherein
    $R^1$ is H;
    said A phenyl substituent is optionally mono- or di-substituted independently with fluoro, trifluoromethyl, trifluoromethoxy, chloro, $(C_1-C_3)$ alkyl, hydroxy, $(C_1-C_2)$alkoxy, amino or mono-N— or di-N,N—$(C_1-C_2)$alkylamino;
or a pharmaceutically acceptable salt thereof.

17. A compound as recited in claim 1 wherein said compound is
    (R)-2-benzylsulfanyl-3-(4-{2-[1-heptyl-3-(4-isopropyl-phenyl)-ureido]-ethyl}-phenyl)-propionic acid;
    (S)-2-benzylsulfanyl-3-(4-{2-[1-heptyl-3-(4-isopropyl-phenyl)-ureido]-ethyl}-phenyl)-propionic acid;

(R)-2-ethylsulfanyl-3-(4-{2-[1-heptyl-3-(4-isopropyl-phenyl)-ureido]-ethyl}-phenyl)-propionic acid;

(S)-2-ethylsulfanyl-3-(4-{2-[1-heptyl-3-(4-isopropyl-phenyl)-ureido]-ethyl}-phenyl)-propionic acid;

(R)-3-(4-{2-[1-heptyl-3-(4-isopropyl-phenyl)-ureido]-ethyl}-phenyl)-2-phenylsulfanyl-propionic acid;

(S)-3-(4-{2-[1-heptyl-3-(4-isopropyl-phenyl)-ureido]-ethyl}-phenyl)-2-phenylsulfanyl-propionic acid;

or the pharmaceutically acceptable salts of said compounds.

18. A compound as recited in claim 16 wherein a. $R^2$ is isopropylthio;
   $R^3$ is hexyl; and
   A is 4-isopropylphenyl; or
b. $R^2$ is benzylthio;
   $R^3$ is hexyl; and
   A is 4-isopropylphenyl; or
c. $R^2$ is ethylthio;
   $R^3$ is hexyl; and
   A is 4-isopropylphenyl; or
d. $R^2$ is phenylthio;
   $R^3$ is hexyl; and
   A is 4-isopropylphenyl;

or the pharmaceutically acceptable salts of said compounds.

19. A compound as recited in claim 1 wherein

E is C(O);

Z is carboxy;

W is a bond or $(C_1-C_4)$alkylene;

$R^1$ is H, $(C_1-C_4)$alkyl, or $(C_3-C_6)$cycloalkyl;

$R^2$ is $(C_1-C_4)$alkoxy, $(C_1-C_4)$alkylthio, phenoxy, benzyloxy, phenylthio, benzylthio, or $(C_1-C_4)$ cycloalkyl, said phenyl moieties optionally mono- or di-substituted independently with cyano, fluoro, trifluoromethyl, trifluoromethoxy, chloro, $(C_1-C_3)$ alkyl, hydroxy, $(C_1-C_2)$alkoxy, amino or mono-N— or di-N,N—$(C_1-C_2)$alkylamino;

$R^3$ is $(C_4-C_8)$alkyl;

$R^5$ and $R^6$ are each H; and

A is a five to six membered partially saturated, fully saturated or fully unsaturated ring optionally having one heteroatom selected from oxygen, sulfur and nitrogen, or a bicyclic ring consisting of two fused partially saturated, fully saturated or fully unsaturated five to six membered rings, taken independently, optionally having one to four heteroatoms selected independently from oxygen, sulfur and nitrogen;
   wherein said A substituent is optionally mono-, di- or tri-substituted independently with halo, $(C_1-C_6)$ alkyl, hydroxy, $(C_1-C_6)$alkoxy, $(C_1-C_4)$alkylthio, amino, nitro, cyano, or mono-N— or di-N,N— $(C_1-C_6)$alkylamino said $(C_1-C_6)$alkyl or $(C_1-C_6)$ alkoxy substituents are optionally substituted independently with from one to nine fluorines or a pharmaceutically acceptable salt thereof.

20. A compound of the Formula I:

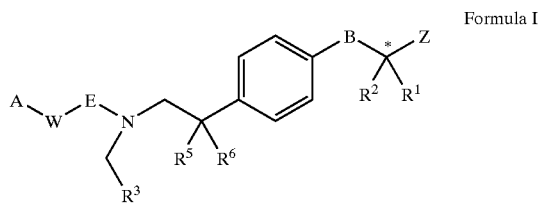

Formula I a prodrug thereof, or a pharmaceutically acceptable salt of said compound or of said prodrug;

wherein

E is carbonyl or sulfonyl;

B is —N(H)—;

Z is carboxyl, carboxaldehyde, hydroxymethyl, $(C_1-C_4)$ alkoxycarbonyl, cyano, hydroxyaminocarbonyl, tetrazolyl, tetrazolylaminocarbonyl, 4,5-dihydro-5-oxo-1,2,4-oxadiazol-3-yl, 3-oxoisoxazolidin-4-yl-aminocarbonyl, or —C(O)N(H)SO$_2$R$^4$;
   where $R^4$ is $(C_1-C_6)$alkyl, amino or mono-N— or di-N,N—$(C_1-C_6)$alkylamino, said $(C_1-C_6)$alkyl substituents are optionally substituted independently with from one to nine fluorines;

W is a bond, —N(H)—, —N(($C_1-C_4$)alkyl)-($C_1-C_4$) alkylamino, or $(C_1-C_8)$alkylene;
   wherein said $(C_1-C_8)$alkylene may optionally be mono- or di-substituted independently with oxo, halo, $(C_1-C_6)$alkoxycarbonyl, $(C_1-C_6)$alkyl, $(C_2-C_6)$alkenyl, $(C_3-C_7)$cycloalkyl, hydroxy, $(C_1-C_6)$alkoxy, $(C_1-C_4)$alkylthio, amino, cyano, nitro, or mono-N— or di-N,N—$(C_1-C_6)$alkylamino or
   wherein W is $CR^7R^8$ wherein $R^7$ and $R^8$ are linked together to form a three to six membered fully saturated carbocyclic ring;

$R^1$ is H, $(C_1-C_6)$alkyl or $(C_3-C_6)$cycloalkyl;

$R^2$ is H, a $(C_3-C_6)$cycloalkyl or a fully saturated, partially unsaturated or fully unsaturated one to four membered straight or branched carbon chain wherein the carbon(s) may optionally be replaced with one or two heteroatoms selected independently from oxygen and sulfur and wherein said carbon(s) is optionally mono-, di- or tri-substituted independently with halo, said carbon(s) is optionally mono-substituted with hydroxy, said carbon(s) is optionally mono-substituted with oxo, said sulfur is optionally mono- or di-substituted with oxo, and said chain is optionally mono-substituted with Y;
   wherein Y is a partially saturated, fully saturated or fully unsaturated three to eight membered ring optionally having one to four heteroatoms selected independently from oxygen, sulfur and nitrogen or a bicyclic ring consisting of two fused partially saturated, fully saturated or fully unsaturated three to six membered rings, taken independently, said bicyclic ring optionally having one to four heteroatoms selected independently from oxygen, sulfur and nitrogen;
   wherein said Y ring is optionally mono-, di- or tri-substituted independently with halo, $(C_2-C_6)$ alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N— $(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; or $R^1$ and $R^2$ are linked together to form a three to six membered fully saturated carbocyclic ring optionally having one heteroatom selected from oxygen, sulfur and nitrogen;

$R^3$ is $(C_1-C_{10})$alkyl, $(C_2-C_{10})$alkenyl or $(C_2-C_{10})$alkynyl, said $(C_1-C_{10})$alkyl, $(C_2-C_{10})$alkenyl or $(C_2-C_{10})$alkynyl substituents are optionally mono-, di- or tri-substituted independently with halo, hydroxy, $(C_1-C_6)$alkoxy, $(C_1-C_4$alkylthio, amino, nitro, cyano, oxo, carboxy, $(C_1-C_6)$alkyloxycarbonyl, or mono-N— or di-N,N— $(C_1-C_6)$alkylamino or optionally said $(C_1-C_{10})$alkyl, $(C_2-C_{10})$alkenyl or $(C_2-C_{10})$alkynyl substituents are mono-substituted with a partially saturated, fully saturated or fully unsaturated five to six membered ring optionally having one to two heteroatoms selected from nitrogen, oxygen and sulfur, or a bicyclic ring consisting of two fused partially saturated, fully saturated or fully unsaturated three to six membered rings, taken independently, said bicyclic ring optionally having one to four heteroatoms selected independently from oxygen, sulfur and nitrogen;

said ring optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R^5$ and $R^6$ are linked together to form a three to six membered fully saturated carbocyclic ring or are each independently H, $(C_1-C_6)$alkyl, $(C_3-C_7)$cycloalkyl or $(C_3-C_7)$cycloalkyl$(C_1-C_6)$alkyl; and A is H, mono-N— or di-N,N—$(C_1-C_6)$alkylamino, $(C_2-C_6)$alkanoylamino, $(C_1-C_6)$alkoxy, or a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, said bicyclic ring optionally having one to four heteroatoms selected independently from oxygen, sulfur and nitrogen; and wherein said A ring is optionally mono-, di- or tri-substituted independently with oxo, carboxy, halo, $(C_1-C_6)$alkoxycarbonyl, $(C_1-C_6)$alkyl, $(C_2-C_6)$alkenyl, $(C_3-C_7)$cycloalkyl, $(C_3-C_7)$cycloalkyl$(C_1-C_6)$alkyl, hydroxy, $(C_1-C_6)$alkoxy, $(C_1-C_4)$ alkylthio, amino, cyano, nitro, or mono-N— or di-N,N—$(C_1-C_6)$alkylamino wherein said $(C_1-C_6)$alkyl or $(C_1-C_6)$alkoxy substituents are optionally mono-, di- or tri-substituted independently with halo, hydroxy, $(C_1-C_6)$alkoxy, amino, mono-N— or di-N,N—$(C_1-C_6)$alkylamino or from one to nine fluorines, or wherein said A ring is optionally mono-substituted with a partially saturated, fully saturated or fully unsaturated three to eight membered ring optionally having one to four heteroatoms selected independently from oxygen, sulfur and nitrogen.

21. A method for treating obesity, hypertriglyceridemia, hyperlipidemia, hypoalphalipoproteinemia, hypercholesterolemia, dyslipidemia, Syndrome X, Type II diabetes mellitus and complications thereof selected from the group consisting of neuropathy, nephropathy, retinopathy and cataracts, hyperinsulinemia, impaired glucose tolerance, insulin resistance, atherosclerosis, hypertension, coronary heart disease, peripheral vascular disease or congestive heart failure in a mammal by administering to a mammal in need of such treatment a therapeutically effective amount of a compound of claim 1 or 20, a prodrug thereof, or a pharmaceutically acceptable salt of said compound or of said prodrug.

22. A method as recited in claim 21 wherein atherosclerosis is treated.

23. A method as recited in claim 21 wherein peripheral vascular disease is treated.

24. A method as recited in claim 21 wherein dyslipidemia is treated.

25. A method as recited in claim 21 wherein Type II diabetes mellitus is treated.

26. A method as recited in claim 21 wherein hypoalphalipoproteinemia is treated.

27. A method as recited in claim 21 wherein hypercholesterolemia is treated.

28. A method as recited in claim 21 wherein hypertriglyceridemia is treated.

29. A method as recited in claim 21 wherein obesity is treated.

30. A pharmaceutical composition which comprises a compound of claim 1 or 20, a prodrug thereof, or a pharmaceutically acceptable salt of said compound or of said prodrug and a pharmaceutically acceptable carrier, vehicle or diluent.

31. A pharmaceutical composition for the treatment of atherosclerosis in a mammal which comprises an atherosclerosis treating amount of a compound of claim 1 or 20, prodrug thereof, or a pharmaceutically acceptable salt of said compound or of said prodrug and a pharmaceutically acceptable carrier, vehicle or diluent.

* * * * *